US012116461B2

(12) United States Patent
Stupp et al.

(10) Patent No.: US 12,116,461 B2
(45) Date of Patent: Oct. 15, 2024

(54) HOST-GUEST INTERACTIONS FOR PA SUPERSTRUCTURE FORMATION

(71) Applicant: Northwestern University, Evanston, IL (US)

(72) Inventors: Samuel I. Stupp, Chicago, IL (US); Alexandra N. Kolberg, Chicago, IL (US); Tristan D. Clemons, Evanston, IL (US); Stacey M. Chin, Cambridge, MA (US)

(73) Assignee: Northwestern University, Evanston, IL (US)

( * ) Notice: Subject to any disclaimer, the term of this patent is extended or adjusted under 35 U.S.C. 154(b) by 278 days.

(21) Appl. No.: 17/409,450

(22) Filed: Aug. 23, 2021

(65) Prior Publication Data

US 2022/0056219 A1 Feb. 24, 2022

Related U.S. Application Data

(60) Provisional application No. 63/068,552, filed on Aug. 21, 2020.

(51) Int. Cl.
*C08L 101/00* (2006.01)
*B33Y 80/00* (2015.01)
(Continued)

(52) U.S. Cl.
CPC ............ *C08G 83/008* (2013.01); *B33Y 80/00* (2014.12); *C08J 3/075* (2013.01); *C08L 101/00* (2013.01);
(Continued)

(58) Field of Classification Search
CPC .. C08G 83/008; C08G 2210/00; B33Y 80/00; C08J 3/075; C08J 2300/204; C08L 101/00; C08L 5/16; C08L 101/14; C09D 5/02; C12N 5/00; C12N 5/0619; C12N 2501/13; C12N 2513/00; C12N 2533/40; C12N 2533/70
See application file for complete search history.

(56) References Cited

U.S. PATENT DOCUMENTS 7,030,167 B2   4/2006   Gunther
7,371,719 B2   5/2008   Stupp et al.
(Continued)

OTHER PUBLICATIONS

Mata et al ("Self-Assembling Hydrogels Based on a Complementary Host-Guest Peptide Amphiphile Pair", Biomacromolecules 2019, 20, 2276-2285). (Year: 2019).*
(Continued)

*Primary Examiner* — Robert S Jones, Jr.
*Assistant Examiner* — Jiangtian Xu
(74) *Attorney, Agent, or Firm* — Casimir Jones, S.C.; Rikki A. Hullinger

(57) ABSTRACT

The disclosure relates to compositions and superstructures comprising peptide amphiphiles. In some aspects, the disclosure relates to compositions and superstructures comprising host and guest peptide amphiphiles, wherein the host and guest moieties of the peptide amphiphiles interact via non-covalent interactions to form a supramolecular assembly, such a superstructure. In some aspects, the superstructure further comprises a bioactive moiety. Suitable bioactive moieties may be selected to promote cell growth, migration, and/or differentiation.

6 Claims, 65 Drawing Sheets

(51) Int. Cl.

| | |
|---|---|
| *C08G 83/00* | (2006.01) |
| *C08J 3/075* | (2006.01) |
| *C09D 5/02* | (2006.01) |
| *C12N 5/00* | (2006.01) |
| *C12N 5/0793* | (2010.01) |
| *C08L 5/16* | (2006.01) |
| *C08L 101/14* | (2006.01) |

(52) U.S. Cl.
CPC ............... *C09D 5/02* (2013.01); *C12N 5/00* (2013.01); *C12N 5/0619* (2013.01); *C08G 2210/00* (2013.01); *C08J 2300/204* (2013.01); *C08L 5/16* (2013.01); *C08L 101/14* (2013.01); *C12N 2501/13* (2013.01); *C12N 2513/00* (2013.01); *C12N 2533/40* (2013.01); *C12N 2533/70* (2013.01)

(56) References Cited

U.S. PATENT DOCUMENTS

| | | |
|---|---|---|
| 7,452,679 B2 | 11/2008 | Stupp et al. |
| 7,491,690 B2 | 2/2009 | Stupp et al. |
| 7,534,761 B1 | 5/2009 | Stupp et al. |
| 7,544,661 B2 | 6/2009 | Stupp et al. |
| 7,554,021 B2 | 6/2009 | Stupp et al. |
| 7,683,025 B2 | 3/2010 | Stupp et al. |
| 7,745,708 B2 | 6/2010 | Stupp et al. |
| 7,838,491 B2 | 11/2010 | Stupp et al. |
| 7,851,445 B2 | 12/2010 | Stupp et al. |
| 8,063,014 B2 | 11/2011 | Stupp et al. |
| 8,076,295 B2 | 12/2011 | Hulvat et al. |
| 8,080,262 B2 | 12/2011 | Lee et al. |
| 8,114,834 B2 | 2/2012 | Hsu et al. |
| 8,114,835 B2 | 2/2012 | Mata et al. |
| 8,124,583 B2 | 2/2012 | Stupp et al. |
| 8,138,140 B2 | 3/2012 | Stupp et al. |
| 8,236,800 B2 | 8/2012 | Degrado et al. |
| 8,450,271 B2 | 5/2013 | Shah et al. |
| 8,512,693 B2 | 8/2013 | Capito et al. |
| 8,546,338 B2 | 10/2013 | Donners et al. |
| 8,580,923 B2 | 11/2013 | Stupp et al. |
| 8,748,569 B2 | 6/2014 | Stupp et al. |
| 8,772,228 B2 | 7/2014 | Stupp et al. |
| 9,011,914 B2 | 4/2015 | Po et al. |
| 9,040,626 B2 | 5/2015 | Chien et al. |
| 9,044,514 B2 | 6/2015 | Xu et al. |

OTHER PUBLICATIONS

Mata et al ("Host-Guest-Mediated Epitope Presentation on Self-Assembled Peptide Amphiphile Hydrogels", ACS Biomater. Sci. Eng. 2020, 6, 4870-4880, herein referred to as "Mata 2020"). (Year: 2020).*
Freeman et al (Science 362, 808-813, 2018). (Year: 2018).*
Stupp et al ("Supramolecular Nanostructure Activates TrkB Receptor Signaling of Neuronal Cells by Mimicking Brain-Derived Neurotrophic Factor", Nano Lett. 2018, 18, 6237-6247). (Year: 2018).*
Albertazzi, L. et al., Probing exchange pathways in one-dimensional aggregates with super-resolution microscopy. Science. May 2, 2014;344(6183):491-5.
Álvarez, Z. et al., The effect of the composition of PLA films and lactate release on glial and neuronal maturation and the maintenance of the neuronal progenitor niche. Biomaterials. Mar. 2013;34(9):2221-33.
Berns, E. J. et al., A tenascin-C mimetic peptide amphiphile nanofiber gel promotes neurite outgrowth and cell migration of neurosphere-derived cells. Acta Biomater. Jun. 2016;37:50-8.
Boekhoven, J. et al., Dynamic display of bioactivity through host-guest chemistry. Angew Chem Int Ed Engl. Nov. 11, 2013;52(46):12077-80.
Bolte, S. et al., A guided tour into subcellular colocalization analysis in light microscopy. JMicrosc. Dec. 2006;224(Pt 3):213-32.
Brewer, G. J. Serum-free B27/neurobasal medium supports differentiated growth of neurons from the striatum, substantia nigra, septum, cerebral cortex, cerebellum, and dentate gyrus. J Neurosci Res. Dec. 1995;42(5):674-83.
Budday, S et al., Rheological characterization of human brain tissue. Acta Biomater. Sep. 15, 2017;60:315-329.
Chin, S. M. et al., Covalent-supramolecular hybrid polymers as muscle-inspired anisotropic actuators. Nat Commun. Jun. 19, 2018;9(1):2395.
Clemons, T. D. et al., Manipulating Cellular Interactions of Poly(glycidyl methacrylate) Nanoparticles Using Mixed Polymer Brushes. ACS Macro Lett. 2016, 5, 10, 1132-1136.
Cromwell, W. C. et al., Cyclodextrin-adamantanecarboxylate inclusion complexes: studies of the variation in cavity size. J Phys Chem-Us 1985, 89, 326-32.
Cui, H. G. et al., Amino acid sequence in constitutionally isomeric tetrapeptide amphiphiles dictates architecture of one-dimensional nanostructures. J Am Chem Soc. Sep. 3, 2014;136(35):12461-8.
Da Silva, R. M. P. et al., Super-resolution microscopy reveals structural diversity in molecular exchange among peptide amphiphile nanofibres. Nat Commun. May 19, 2016;7:11561.
Datta, S., et al., Hierarchical Assemblies of Supramolecular Coordination Complexes. Acc Chem Res. Sep. 18, 2018;51(9):2047-2063.
Dunn, K. W. et al., A practical guide to evaluating colocalization in biological microscopy. Am J Physiol Cell Physiol. Apr. 2011;300(4):C723-42.
Edelbrock, A. N. et al., Supramolecular Nanostructure Activates TrkB Receptor Signaling of Neuronal Cells by Mimicking Brain-Derived Neurotrophic Factor. Nano Lett. Oct. 10, 2018;18(10):6237-6247.
Freeman, R. et al., Reversible self-assembly of superstructured networks. Science. Nov. 16, 2018;362(6416):808-813.
Gardel, M. L. et al. Elastic behavior of cross-linked and bundled actin networks. Science. May 28, 2004;304(5675):1301-5.
Goldberger, J. E. et al., Electrostatic control of bioactivity. Angew Chem Int Ed Engl. Jul. 4, 2011;50(28):6292-5.
Greenfield, N. Using circular dichroism spectra to estimate protein secondary structure. Nat Protoc. 2006;1(6):2876-90.
Gurkan, U. A. et al., Simple precision creation of digitally specified, spatially heterogeneous, engineered tissue architectures. Adv Mater. Feb. 25, 2013;25(8):1192-8.
Hamsici, S. et al., Bioactive peptide functionalized aligned cyclodextrin nanofibers for neurite outgrowth. J Mater Chem B. Jan. 21, 2017;5(3):517-524.
Harrison, J. C. et al., Cyclodextrin-adamantanecarboxylate inclusion complexes: A model system for the hydrophobic effect. Biopolymers 1982, 21, 1153.
Israelachvili, J. N. Intermolecular and surface forces; 2nd ed .; Academic: London San Diego, 1992. Table of Contents.
Karsenti, E. Self-organization in cell biology: a brief history. Nat Rev Mol Cell Biol. Mar. 2008;9(3):255-62.
Kirschner, D. A. et al., X-ray diffraction from intraneuronal paired helical filaments and extraneuronal amyloid fibers in Alzheimer disease indicates cross-beta conformation. Proc Natl Acad Sci U S A. Jan. 1986;83(2):503-7.
Klein, M. K. et al., Development of Optimized Tissue-Factor-Targeted Peptide Amphiphile Nanofibers to Slow Noncompressible Torso Hemorrhage. ACS Nano. Jun. 23, 2020;14(6):6649-6662.
Lanjakornsiripan, D. et al., Layer-specific morphological and molecular differences in neocortical astrocytes and their dependence on neuronal layers. Nat Commun. Apr. 24, 2018;9(1):1623.
Lee, S. S. et al., Sulfated glycopeptide nanostructures for multipotent protein activation. Nat Nanotechnol. Aug. 2017;12(8):821-829.
Loebel, C. et al., Shear-thinning and self-healing hydrogels as injectable therapeutics and for 3D-printing. Nat Protoc. Aug. 2017;12(8):1521-1541.
Ma, C. X. et al., Supramolecular Lego assembly towards three-dimensional multi-responsive hydrogels. Adv Mater. Aug. 27, 2014;26(32):5665-9.

(56) References Cited

OTHER PUBLICATIONS

Manders, E. M. M. et al., Dynamics of three-dimensional replication patterns during the S-phase, analysed by double labelling of DNA and confocal microscopy. J Cell Sci. Nov. 1992;103 ( Pt 3):857-62.

Manning, M. C. et al., Circular dichroism studies of distorted alpha-helices, twisted beta-sheets, and beta turns. Biophys Chem. Aug. 1988;31(1-2):77-86.

Marquardt, L. M. et al., Designer, injectable gels to prevent transplanted Schwann cell loss during spinal cord injury therapy. Sci Adv. Apr. 1, 2020;6(14):eaaz1039.

Mayo, K.H. et al. A recipe for designing water-soluble, beta-sheet-forming peptides. Protein Sci. Jul. 1996;5(7):1301-15.

Micsonai, A. Accurate secondary structure prediction and fold recognition for circular dichroism spectroscopy. Proc Natl Acad Sci U S A. Jun. 16, 2015;112(24):E3095-103.

Moyer, T. J. et al., Tuning nanostructure dimensions with supramolecular twisting. J Phys Chem B 2013, 117, 4604. J Phys Chem B. Apr. 25, 2013;117(16):4604-10.

Murphy, S. V. et al., Opportunities and challenges of translational 3D bioprinting. Nat Biomed Eng. Apr. 2020;4(4):370-380.

Nakahata, M. et al., Redox-responsive self-healing materials formed from host-guest polymers. Nat Commun. Oct. 25, 2011;2:511.

Nakamura, T. et al., A metal-ion-responsive adhesive material via switching of molecular recognition properties. Nat Commun. Aug. 7, 2014;5:4622.

Needleman, D. et al., Active matter at the interface between materials science and cell biology. Nat Rev Mater 2017, 2(9), 17048.

Nguyen, J. T. et al. X-ray diffraction of scrapie prion rods and PrP peptides. J Mol Biol. Sep. 29, 1995;252(4):412-22.

Ortega, J.A. et al., BDNF/MAPK/ERK-induced BMP7 expression in the developing cerebral cortex induces premature radial glia differentiation and impairs neuronal migration. Cereb Cortex. Sep. 2010;20(9):2132-44.

Pashuck, E. T. et al., Tuning supramolecular rigidity of peptide fibers through molecular structure. J Am Chem Soc. May 5, 2010;132(17):6041-6.

Quan, C. Y. et al., Core-shell nanosized assemblies mediated by the alpha-beta cyclodextrin dimer with a tumor-triggered targeting property. ACS Nano. Jul. 27, 2010;4(7):4211-9.

Redondo-Gomez, C. et al., Self-Assembling Hydrogels Based on a Complementary Host-Guest Peptide Amphiphile Pair. Biomacromolecules. Jun. 10, 2019;20(6):2276-2285.

Rest, C. et al., Correction: Strategies to create hierarchical self-assembled structures via cooperative non-covalent interactions. Chem Soc Rev. Apr. 21, 2015;44(8):2573.

Rodell, C. B. et al., Rational design of network properties in guest-host assembled and shear-thinning hyaluronic acid hydrogels. Biomacromolecules. Nov. 11, 2013;14(11):4125-34.

Schindelin, J. et al., Fiji: an open-source platform for biological-image analysis. Nat Methods. Jun. 28, 2012;9(7):676-82.

Silva, G. A. et al., Selective differentiation of neural progenitor cells by high-epitope density nanofibers. Science. Feb. 27, 2004;303(5662):1352-5.

Sleep, E. et al., Injectable biomimetic liquid crystalline scaffolds enhance muscle stem cell transplantation. Proc Natl Acad Sci U S A. Sep. 19, 2017;114(38):E7919-E7928.

Song, K. H. et al., Photopolymerized Triazole-Based Glassy Polymer Networks with Superior Tensile Toughness. Adv Funct Mater. May 30, 2018;28(22):1801095.

Spencer, K. C. et al., Characterization of Mechanically Matched Hydrogel Coatings to Improve the Biocompatibility of Neural Implants. Sci Rep. May 16, 2017;7(1):1952.

Stupp, S.I., et al., Supramolecular and Hybrid Bonding Polymers. Isr J Chem. Jan. 2020;60(1-2):132-139.

Takashima, Y. et al., Expansion-contraction of photoresponsive artificial muscle regulated by host-guest interactions. Nat Commun. 2012;3:1270.

Tantakitti, F. et al., Energy landscapes and functions of supramolecular systems. Nat Mater. Apr. 2016;15(4):469-76.

Van Den Ameele, J et al., Thinking out of the dish: what to learn about cortical development using pluripotent stem cells.Trends Neurosci. Jun. 2014;37(6):334-42.

Webber, M. J. et al., Supramolecular nanostructures that mimic VEGF as a strategy for ischemic tissue repair. Proc Natl Acad Sci U S A. Aug. 16, 2011;108(33):13438-43.

Wester, J. R. et al., Supramolecular Exchange among Assemblies of Opposite Charge Leads to Hierarchical Structures. J Am Chem Soc. Jul. 15, 2020;142(28):12216-12225.

Whitesides, G.M. et al. Self-assembly at all scales. Science. Mar. 29, 2002;295(5564):2418-21.

Yan, Q. et al., ATP-triggered biomimetic deformations of bioinspired receptor-containing polymer assemblies. Chem Sci. Jul. 1, 2015;6(7):4343-4349.

Yan, Q., et al., CO2-Switchable Supramolecular Block Glycopolypeptide Assemblies. ACS Macro Lett. 2014, 3, 5, 472-476.

Yang, H.Y. et al., Obtaining information about protein secondary structures in aqueous solution using Fourier transform IR spectroscopy. Nat Protoc. Mar. 2015;10(3):382-96.

Zhang, M. et al., Properties and biocompatibility of chitosan films modified by blending with PEG. Biomaterials. Jul. 2002;23(13):2641-8.

* cited by examiner

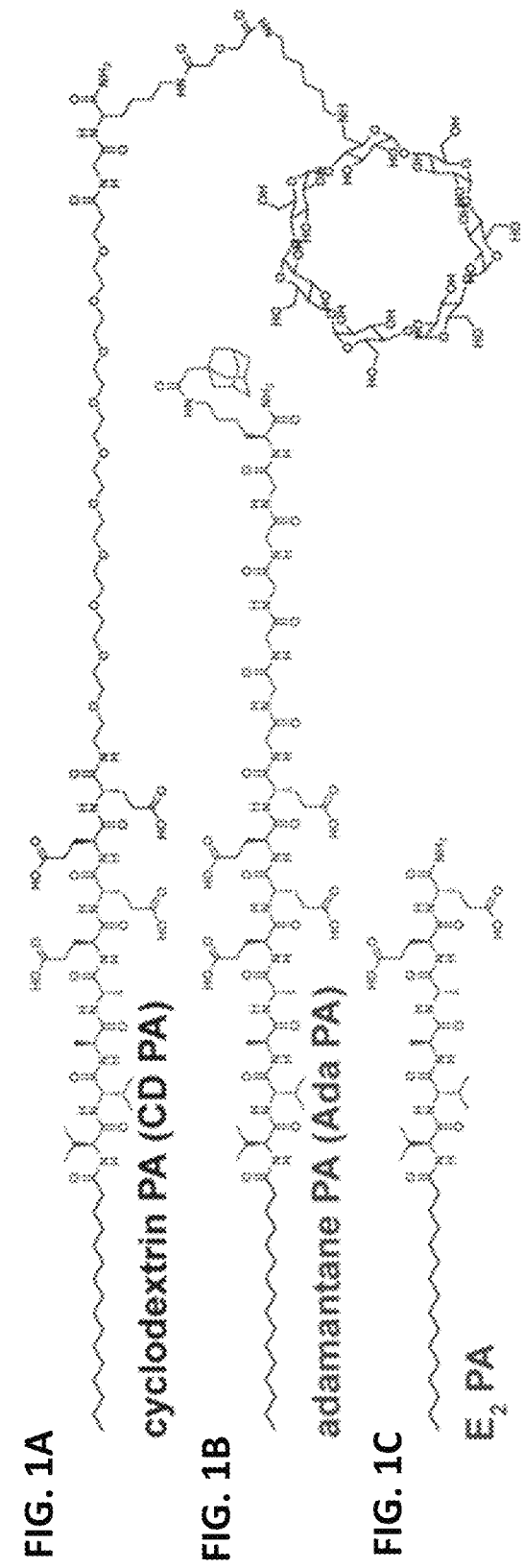
FIG. 1A cyclodextrin PA (CD PA)
FIG. 1B adamantane PA (Ada PA)
FIG. 1C $E_2$ PA

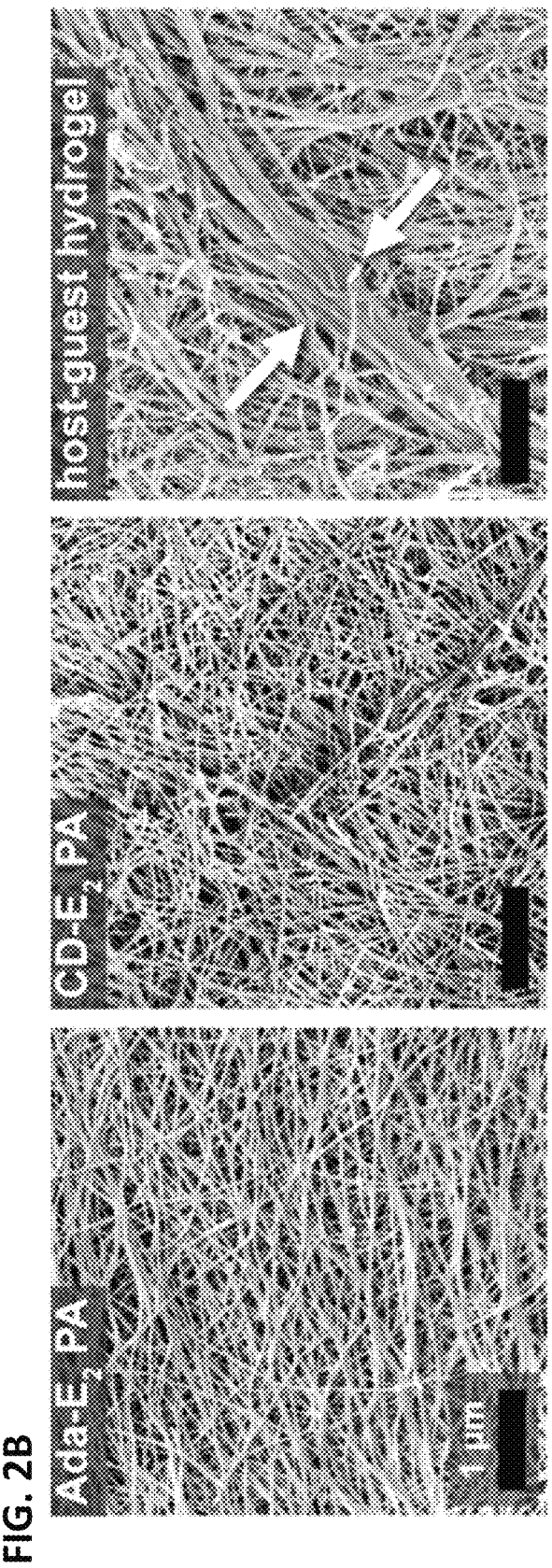

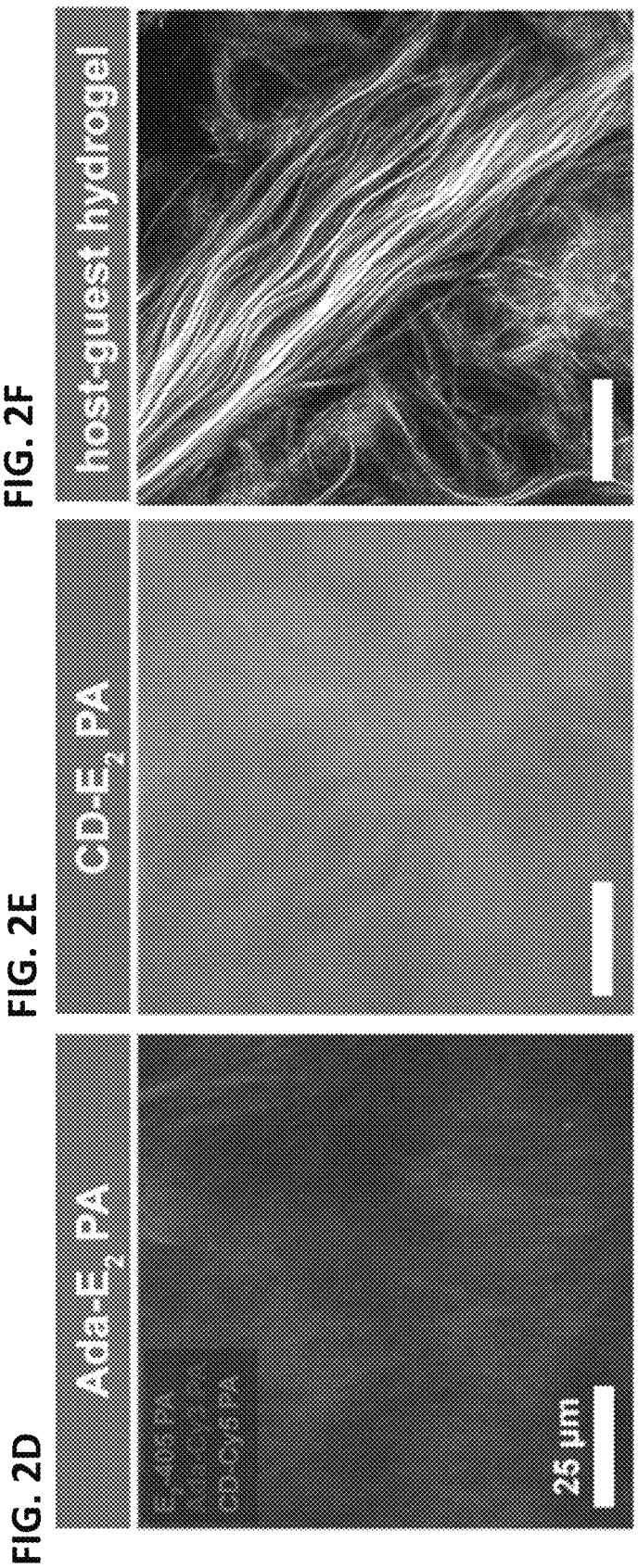

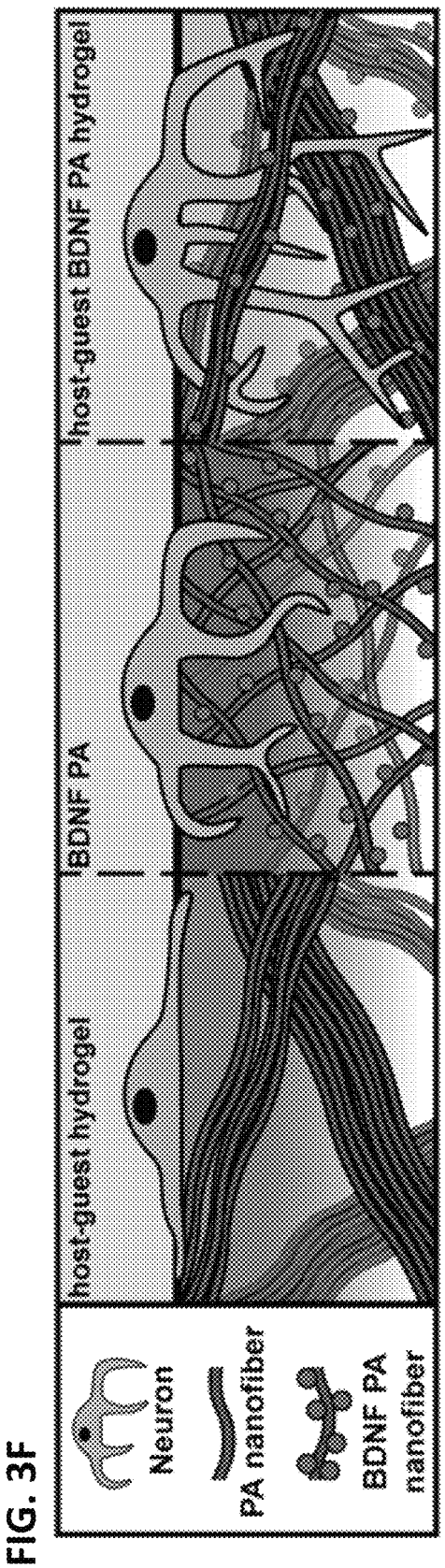

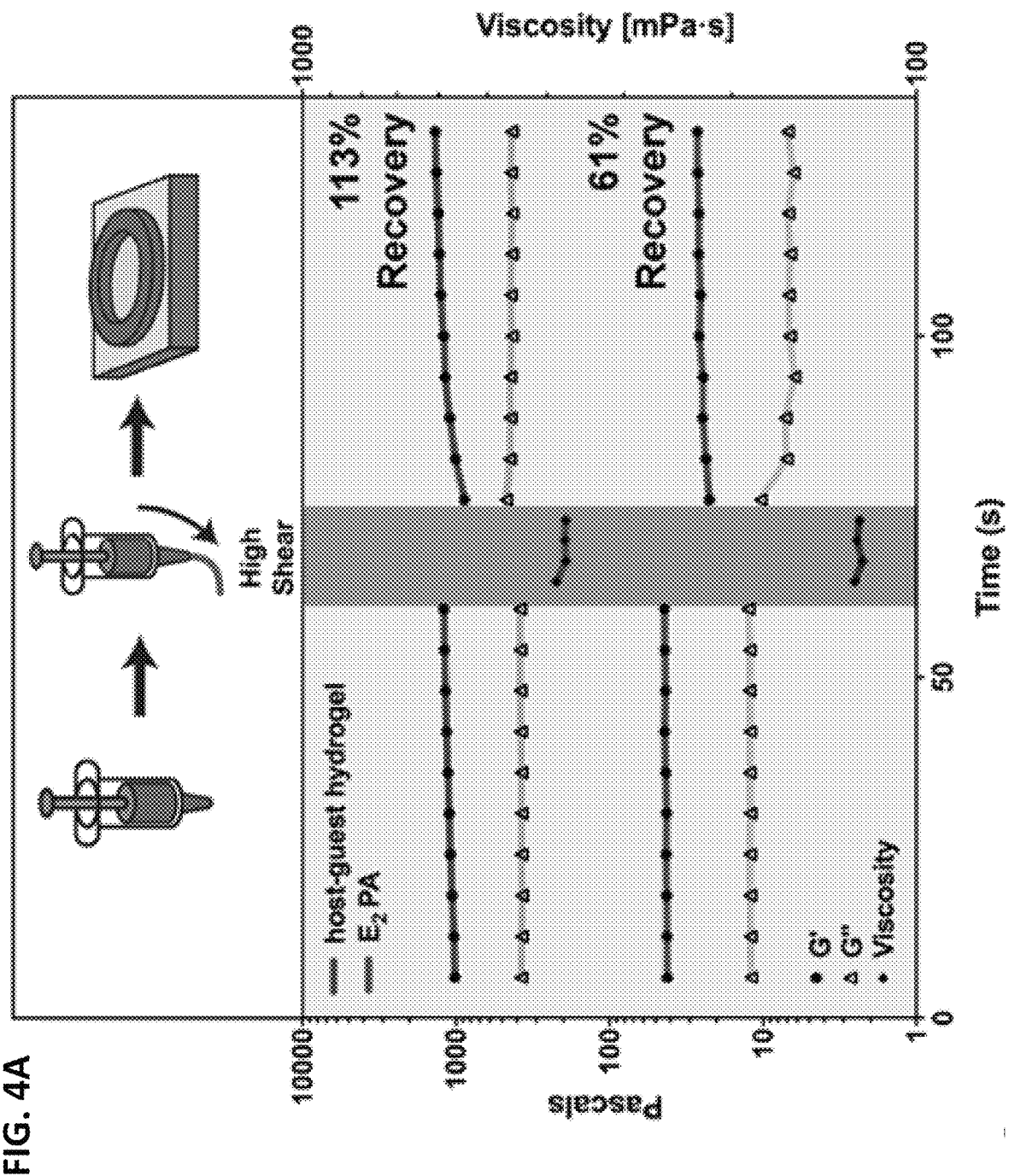

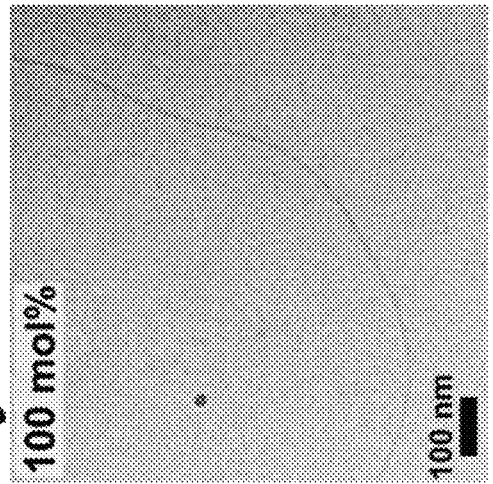
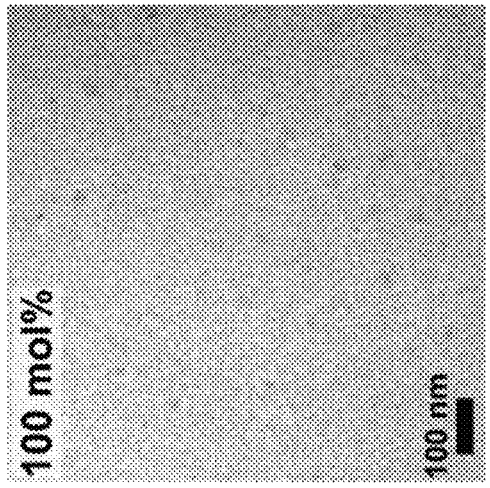
FIG. 5A
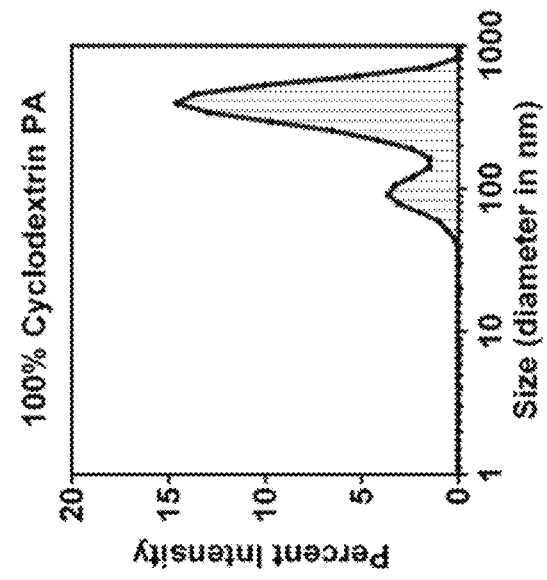
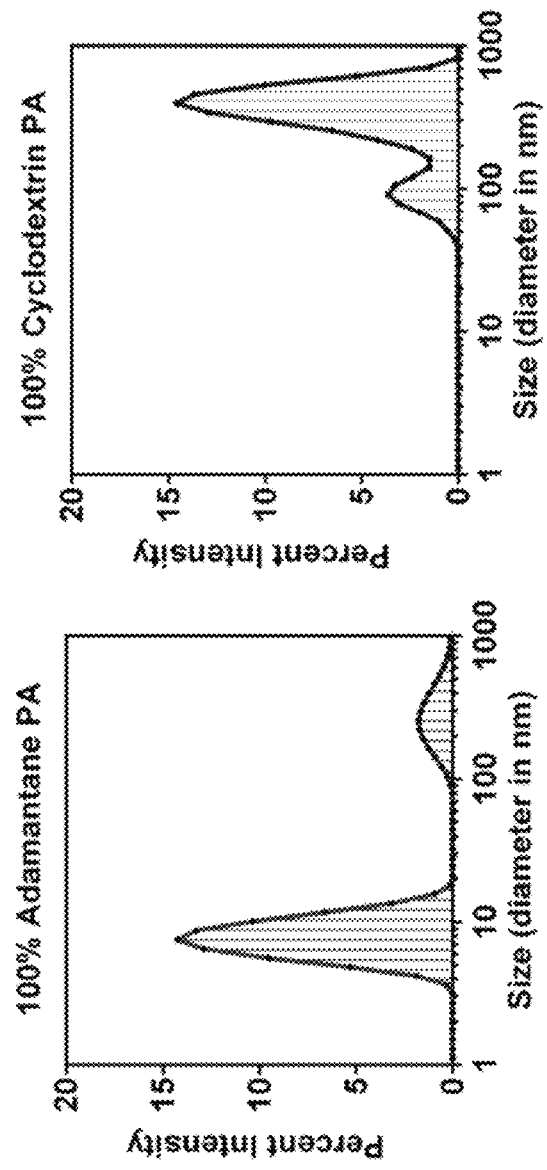
FIG. 5B

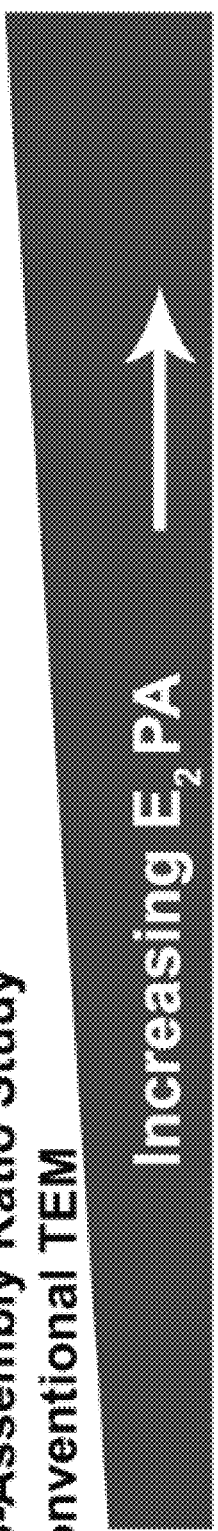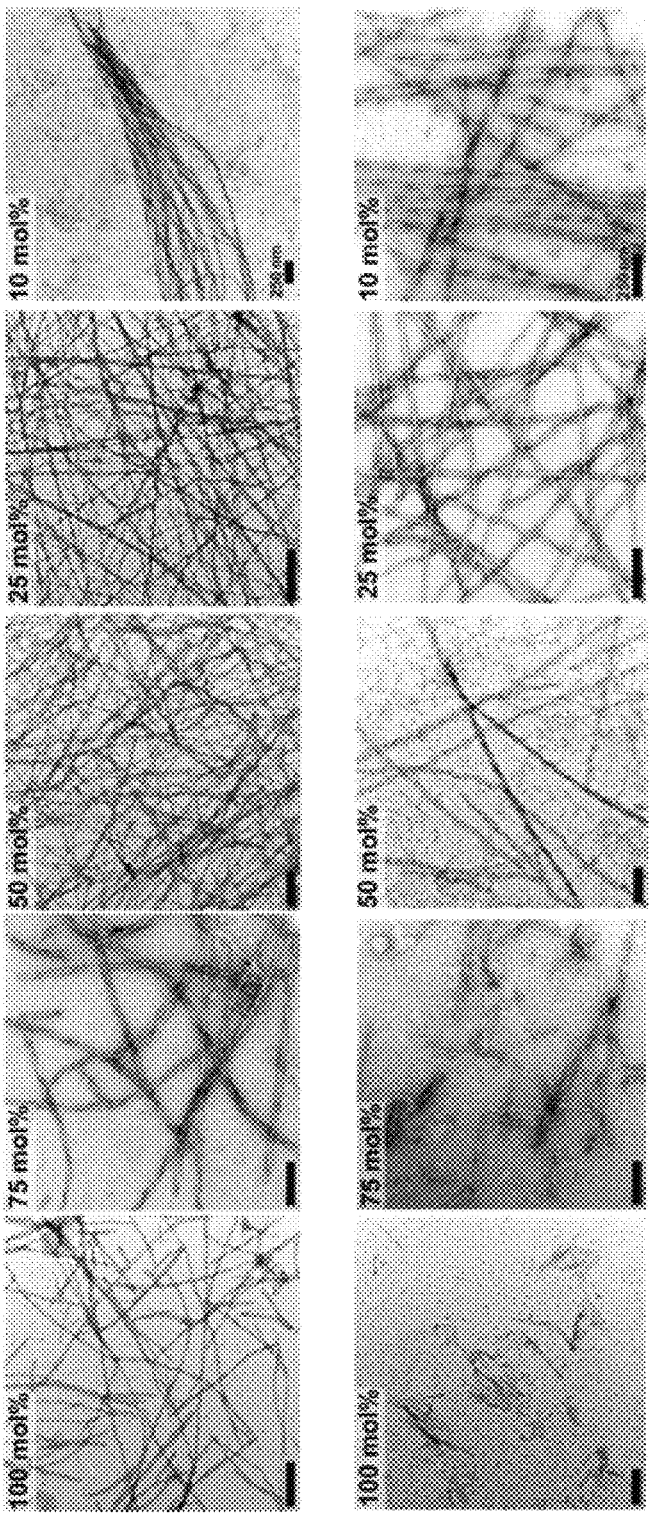
FIG. 7A  Ada-E$_2$ PA
FIG. 7B  CD-E$_2$ PA
Co-Assembly Ratio Study
Conventional TEM
Increasing E$_2$ PA

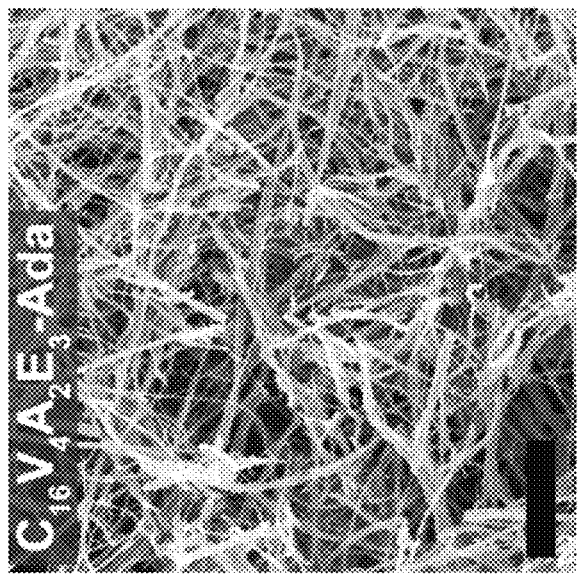
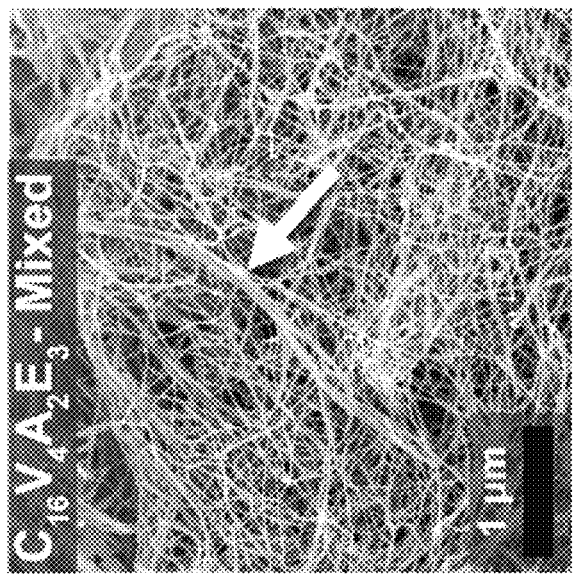
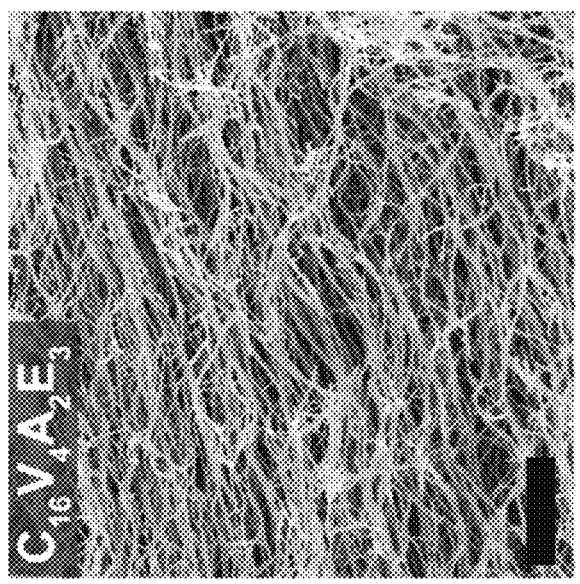
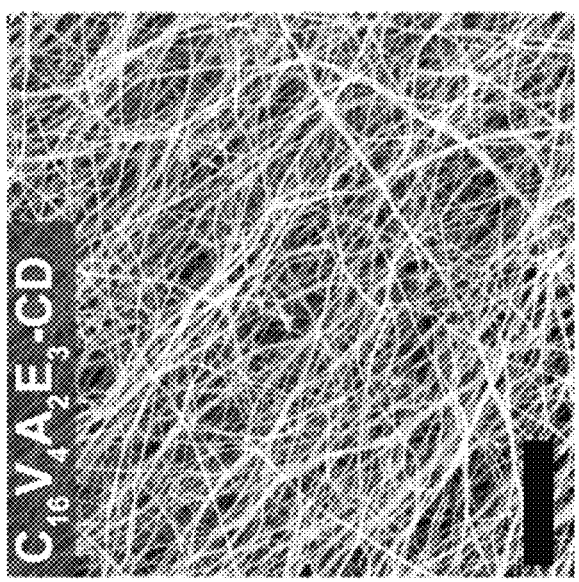
FIG. 17A

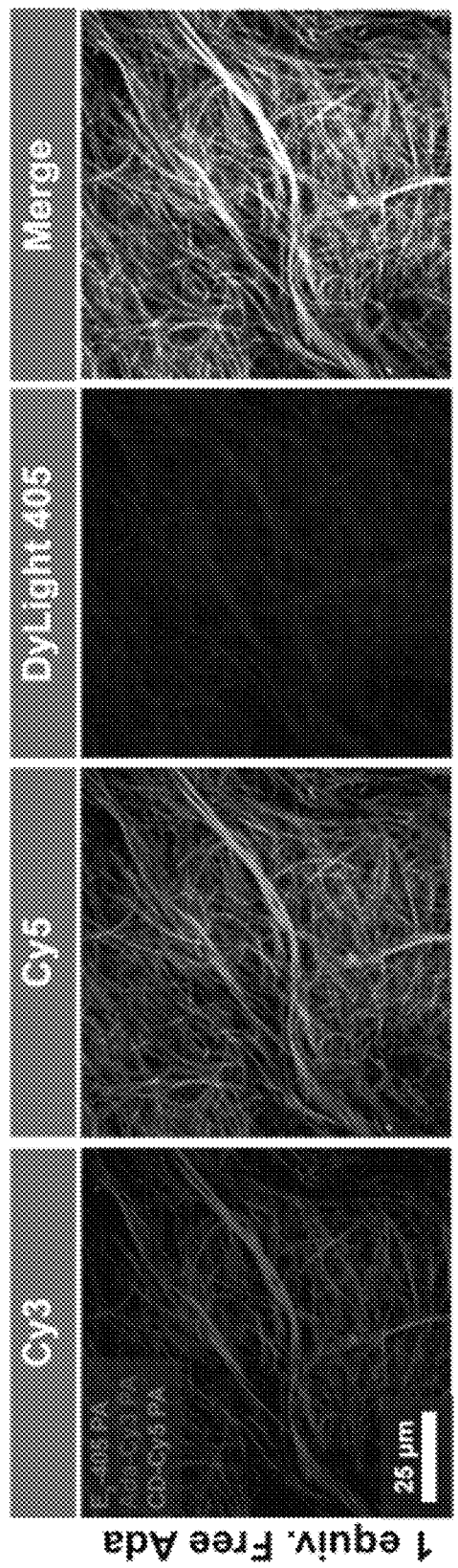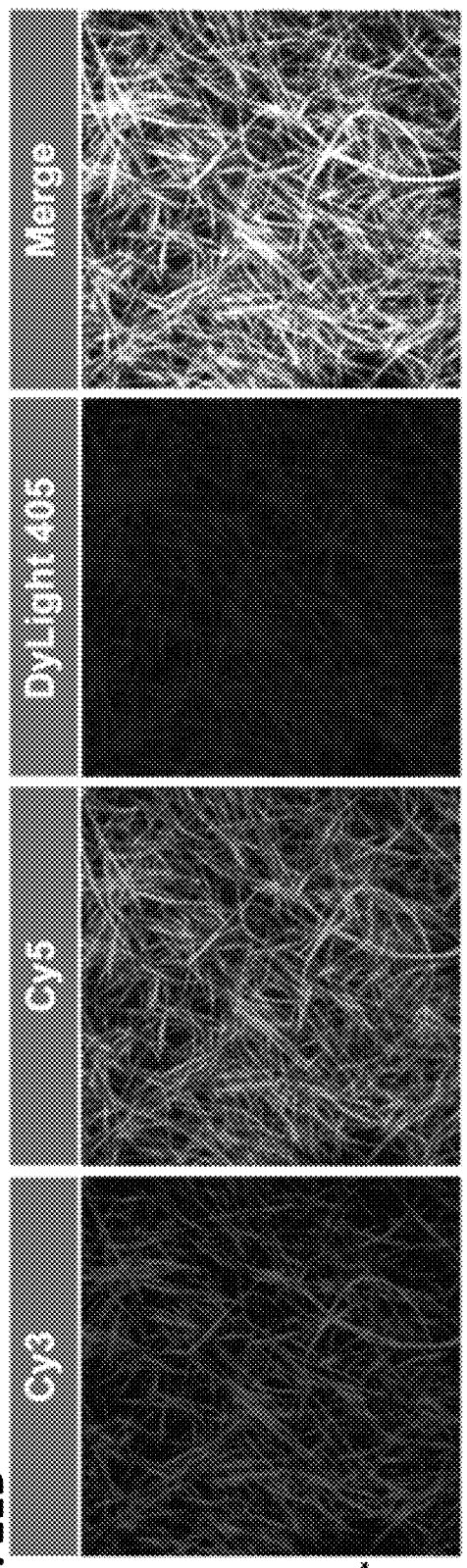
FIG. 21A  
FIG. 21B

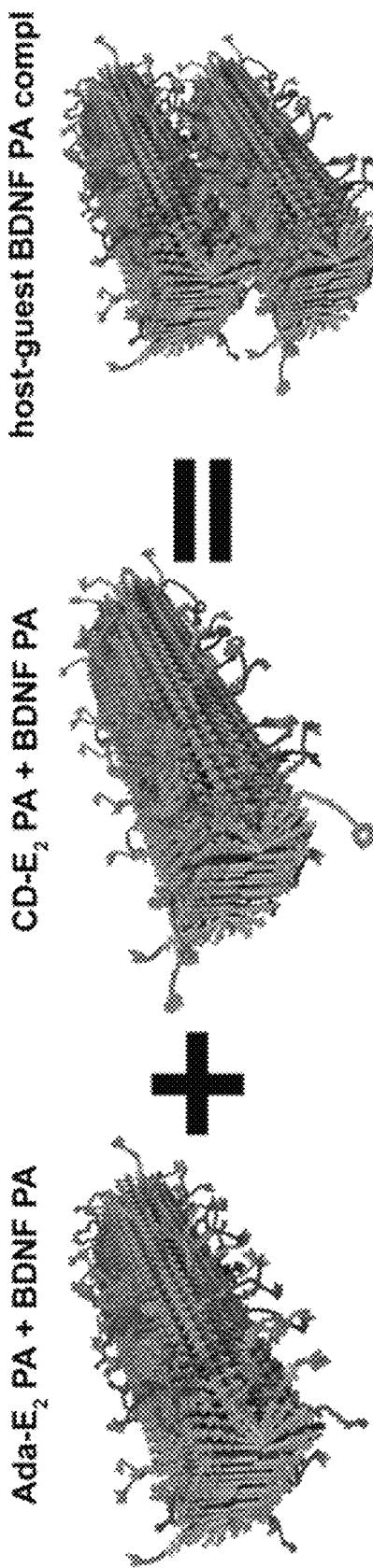
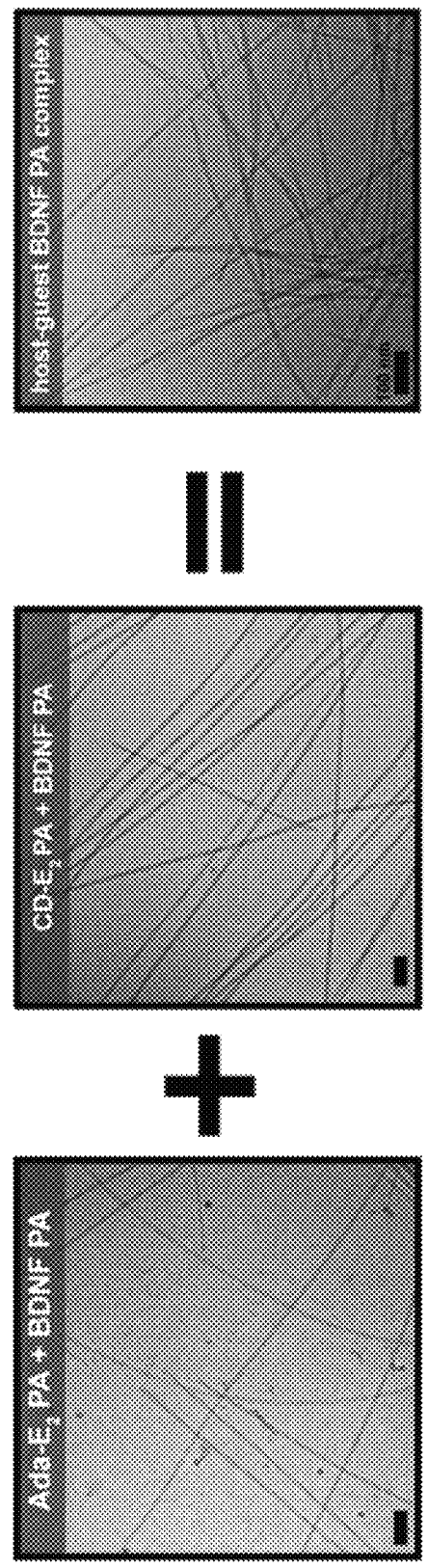
FIG. 22A
FIG. 22B

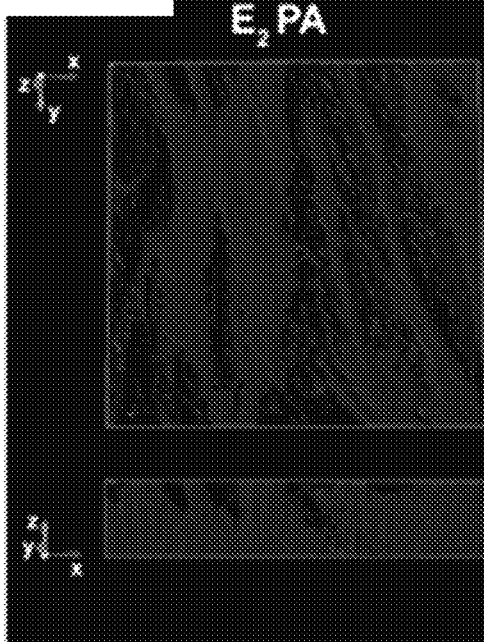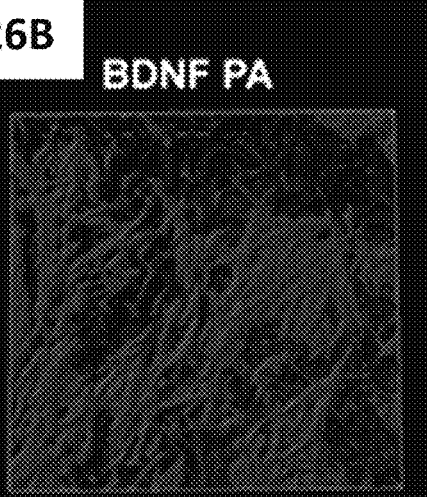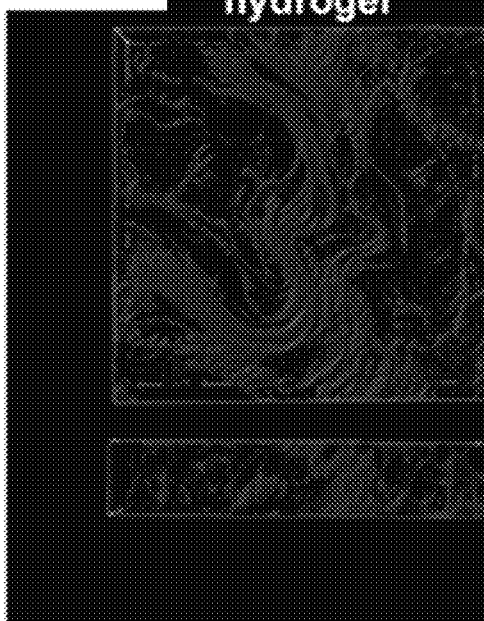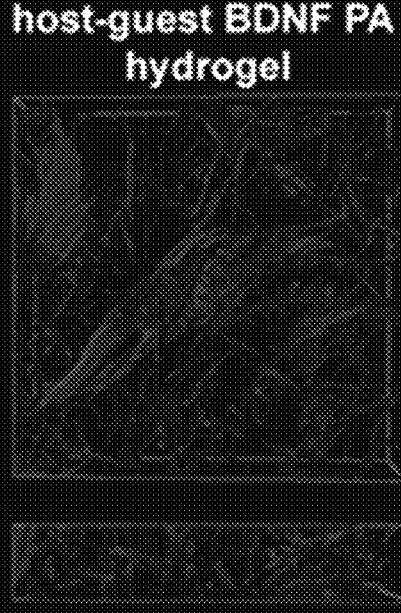
FIG. 26A E₂ PA
FIG. 26B BDNF PA
FIG. 26C host-guest hydrogel
FIG. 26D host-guest BDNF PA hydrogel

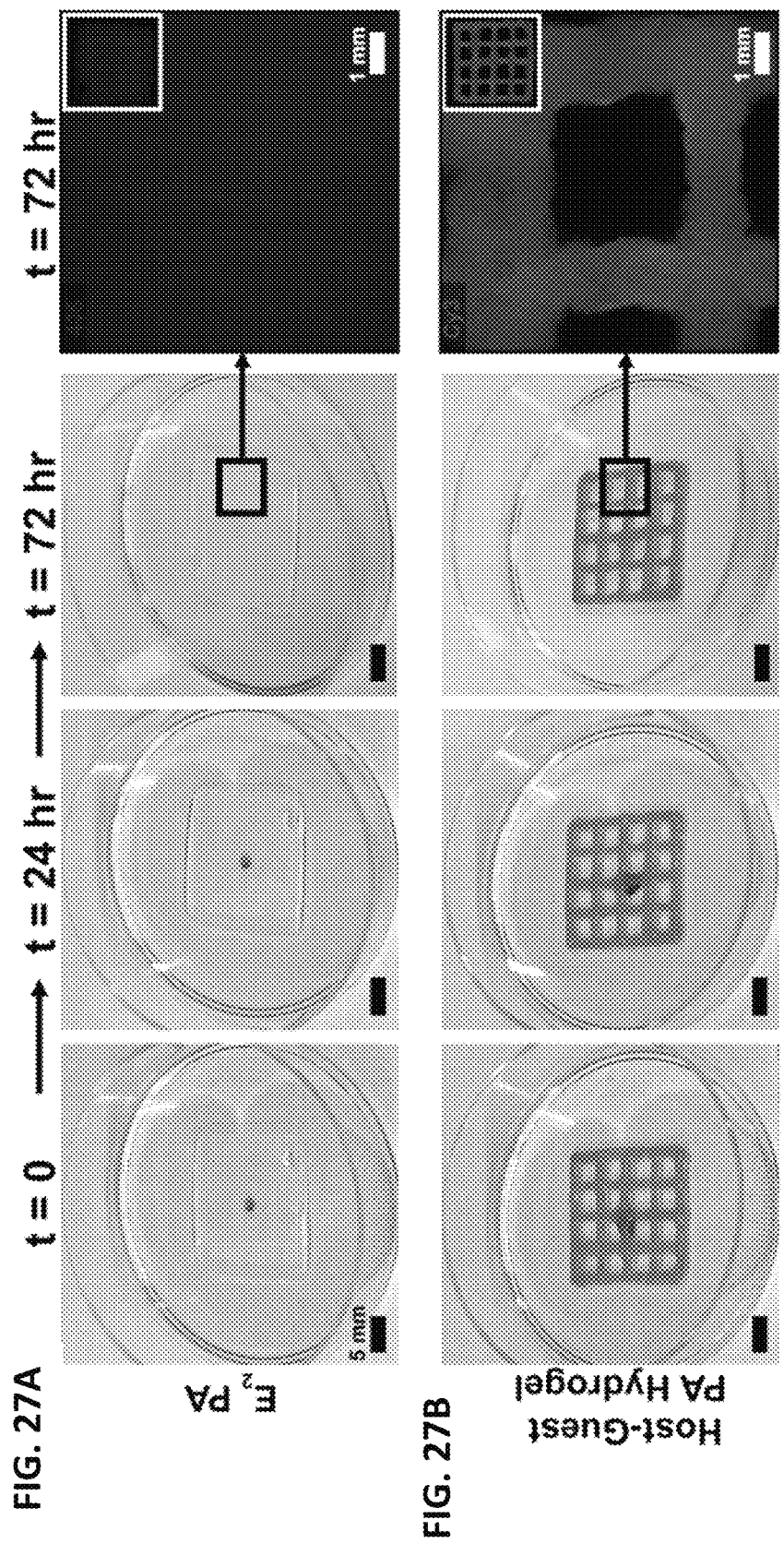
FIG. 27A  E₂ PA
FIG. 27B  Host-Guest PA Hydrogel

HOST-GUEST INTERACTIONS FOR PA SUPERSTRUCTURE FORMATION

STATEMENT OF RELATED APPLICATIONS

This application claims priority to U.S. Provisional Patent Application No. 63/068,552, filed Aug. 21, 2020, the entire contents of which are incorporated herein by reference.

BACKGROUND

Reversible hierarchical self-assembly of molecules, through multiple orthogonal interactions have been harnessed by living systems to control the formation of structures such as protein assemblies, cellular membranes, and cytoskeletal filaments and countless other examples.[1-4] These highly organized but dynamic structures, held together by non-covalent interactions, play critical roles in the regulation of life processes.[5, 6] The non-covalent bonds enable transient complexation among molecules of interest, thus allowing reversible and dynamic functionality in the hierarchical structures of living matter.[7] The ability to emulate this dynamic hierarchical self-assembly in synthetic systems has proven to be challenging, especially to trigger the reversible assembly of molecules. Accordingly, what is needed are reversible, dynamic hierarchical structures and suitable methods for production of the same.

SUMMARY

In some aspects, provided herein are compositions. In some embodiments, provided herein is a composition comprising one or more host peptide amphiphiles. The one or more host peptide amphiphiles comprise a hydrophobic segment, a structural peptide segment, a charged peptide segment, and a host moiety. In some embodiments, the composition further comprises one or more guest peptide amphiphiles. The one or more guest peptide amphiphiles comprise a hydrophobic segment, a structural peptide segment, a charged peptide segment, and a guest moiety. In some embodiments, the composition further comprises one or more diluent peptide amphiphiles. In some embodiments, each of the one or more diluent peptide amphiphiles comprises a hydrophobic segment, a structural peptide segment, and a charged peptide segment, and does not comprise a host moiety or a guest moiety. In some embodiments, the host moiety and the guest moiety interact non-covalently to form a host-guest complex within the composition. In some embodiments, the host moiety is β-cyclodextrin and the guest moiety is adamantane.

In some embodiments, hydrophobic segment comprises an 8-24 carbon alkyl chain ($C_{8-24}$), the structural peptide segment has propensity to form β-sheet-like structures with adjacent structural peptide segments, and the charged peptide segment comprises an acidic, basic, or zwitterionic peptide segment. For example, in some embodiments the structural peptide segment comprises $V_2A_2$, $V_3A_3$, $V_2A_3$, or $V_3A_2$ and the charged peptide segment comprises $E_{2-4}$.

In some embodiments, the host moiety and/or the guest moiety may be conjugated to the PA backbone by a suitable linker. In some embodiments, the β-cyclodextrin is conjugated to the charged peptide segment by a linker comprising 5-15 repeating polyethylene glycol (PEG) units. In some embodiments, the adamantane is conjugated to the charged peptide segment by a linker comprising 4-6 glycine residues.

In some embodiments, the host peptide amphiphile comprises the sequence $C_{8-24}V_2A_2E_4PEG_{10}$-β-cyclodextrin. In some embodiments, the guest peptide amphiphile comprises the sequence $C_{8-24}V_2A_2E_4G_6$-adamanatane. In some embodiments, the diluent peptide amphiphile comprises the sequence $C_{8-24}V_2A_2E_2$.

In some embodiments, the composition further comprises one or more bioactive peptide amphiphiles. The bioactive peptide amphiphiles comprises a hydrophobic segment, a structural peptide segment, a charged peptide segment, and a bioactive moiety. In some embodiments, the bioactive moiety is a growth factor or a growth factor mimetic. For example, in some embodiments the bioactive moiety is a BDNF mimetic peptide. In some embodiments, the bioactive peptide amphiphile comprises a $C_{8-24}$ $V_2A_2E_{2-4}$ backbone sequence linked to the BDNF mimetic peptide.

The composition may be a hydrogel. In some embodiments, provided herein is a hydrogel comprising one or more superstructures. In some embodiments, each superstructure comprises one or more host peptide amphiphiles and one or more guest peptide amphiphiles. In some embodiments, at least one superstructure further comprises one or more bioactive peptide amphiphiles. In some embodiments, each host peptide amphiphile comprises a hydrophobic segment, a structural peptide segment, a charged peptide segment, and a host moiety. In some embodiments, each guest peptide amphiphiles comprises a hydrophobic segment, a structural peptide segment, a charged peptide segment, and a guest moiety. In some embodiments, each bioactive peptide amphiphile comprises a hydrophobic segment, a structural peptide segment, a charged peptide segment, and a bioactive moiety. In some embodiments, each superstructure in the hydrogel is a bundle of supramolecular polymers formed at least in part by non-covalent interactions between the host moiety and the guest moiety. In some embodiments, the host moiety is β-cyclodextrin and the guest moiety is adamantane.

In some embodiments, the hydrogel further comprises one or more diluent peptide amphiphiles. In some embodiments, each diluent peptide amphiphile comprises a hydrophobic segment, a structural peptide segment, and a charged peptide segment, and does not comprise a host moiety, a guest moiety, or a bioactive moiety.

In some embodiments, the hydrophobic segment comprises an 8-24 carbon alkyl chain ($C_{8-24}$), the structural peptide segment has propensity to form β-sheet-like structures with adjacent structural peptide segments, and the charged peptide segment comprises an acidic, basic, or zwitterionic peptide segment. For example, in some embodiments the structural peptide segment comprises $V_2A_2$, $V_3A_3$, $V_2A_3$, or $V_3A_2$ and the charged peptide segment comprises $E_{2-4}$. In some embodiments, the β-cyclodextrin is conjugated to the charged peptide segment by a linker comprising 5-15 repeating polyethylene glycol (PEG) units and wherein the adamantane is conjugated to the charged peptide segment by a linker comprising 4-6 glycine residues.

In some embodiments, the host peptide amphiphile comprises the sequence $C_{8-24}V_2A_2E_4PEG_{10}$-β-cyclodextrin, the guest peptide amphiphile comprises the sequence $C_{8-24}V_2A_2E_4G_6$-adamanatane, and/or the diluent peptide amphiphile comprises the sequence $C_{8-24}V_2A_2E_2$. In some embodiments, the bioactive moiety is a BDNF mimetic peptide. In some embodiments, the bioactive peptide amphiphile comprises a $C_{8-24}$ $V_2A_2E_{2-4}$ backbone sequence linked to the BDNF mimetic peptide.

In some embodiments, the hydrogel further comprises one or more cells. For example, such a hydrogel comprising one or more cells may be used to promote differentiation and/or migration of the one or more cells. Accordingly, hydrogels herein find use in cell culture methods, tissue regeneration methods, cell modeling methods, and the like. In some embodiments, the hydrogel is generated by 3-D printing.

BRIEF DESCRIPTION OF THE DRAWINGS

FIG. 1A-H. Design and characterization of host-guest modified peptide amphiphiles (PAS). (FIG. 1A-C) Chemical structures of (FIG. 1A) the cyclodextrin PA (CD PA), (FIG. 1B) the adamantane PA (Ada PA) and (FIG. 1C) $E_2$ PA. (FIG. 1D) Schematic representation of the supramolecular polymer formed by the Ada-$E_2$ PA, the CD-$E_2$ PA, and their mixture forming host-guest complexes. (FIG. 1E) Cryogenic transmission electron micrographs of CD-$E_2$ PA, Ada-$E_2$ PA, and their mixture. (FIG. 1F) Small angle x-ray scattering patterns, (FIG. 1G) wide angle x-ray scattering patterns, and (FIG. 1H) circular dichroism spectra corresponding to the mixture of CD-$E_2$ PA and Ada-$E_2$ PA (purple), CD-$E_2$ PA (blue), Ada-$E_2$ PA (red), and $E_2$ PA (green). The CD PA and Ada PA were each co-assembled at 10 mol % with the $E_2$ PA separately to form the CD-$E_2$ PA and Ada-$E_2$ PA, respectively. These materials were then mixed 1:1 by volume to make the host-guest PA complex for all experiments.

FIG. 2A-K. Characterization of host-guest superstructure formation. (FIG. 2A) Photographs of solutions in inverted vials of Ada-$E_2$ PA and CD-$E_2$ PA, and of the self-supporting hydrogel formed by their mixture (host-guest hydrogel). (FIG. 2B) Scanning electron micrographs showing nanoribbons in gelled Ada-$E_2$ PA, CD-$E_2$ PA, and the characteristic superstructures (between white arrows) formed in the host-guest hydrogel. (FIG. 2C) Storage (G') and loss (G") moduli of (left-right) the $E_2$ PA, Ada-$E_2$ PA, CD-$E_2$ PA, and the host-guest hydrogel. Confocal optical micrographs of Ada-$E_2$ PA labeled with Cy3 dye (red) (FIG. 2D), the CD-$E_2$ PA labeled with Cy5 dye (green) (FIG. 2E), and their mixture to form the host-guest hydrogel (FIG. 2F) (all samples were co-assembled with the $E_2$ PA labeled with DyLight™ 405 dye (blue)). (FIG. 2G) Pearson's correlation coefficient analysis quantifying colocalization of the blue and red channels (left), blue and green channels (middle) and the red and green channels (right) from micrographs of the host-guest hydrogel. (FIG. 2H) Storage (G') and loss (G") moduli of (left-right) the host-guest hydrogel of Ada-$E_2$ PA and CD-$E_2$ PA, the host-guest hydrogel plus 0.5 equivalents (equiv.) of free adamantane (Free Ada), and the host-guest hydrogel plus 1 equiv. Free Ada. (FIG. 2I) Small angle x-ray scattering curves of the host-guest hydrogel and the host-guest hydrogel plus 0.5 equiv. of Free Ada. (FIG. 2J) Confocal micrograph using dye labels described in (FIG. 2D) after the addition of 1 equivalent of Free Ada to the host-guest hydrogel. (FIG. 2K) Schematic representation of superstructure formation resulting from molecular exchange of the host and guest functionalized peptide amphiphiles. Upon mixing of the Ada-$E_2$ PA (red) and CD-$E_2$ PA (green), redistribution of host and guest functionalized molecules through molecular exchange results in the localized enrichment of these functionalized molecules to form hierarchical superstructures. $P<0.01$, *$P<0.001$, and ****$P<0.0001$ LSD test (FIG. 2C) (n=3), (FIG. 2G) (n=10), (FIG. 2H) (n=2).

FIG. 3A-F. Effect of BDNF mimetic superstructured scaffolds on primary neuronal cultures. (FIG. 3A) Western blot of phosphorylated TrkB (p-TrkB), TrkB, and actin in neuronal cells treated in vitro with starvation media (Strv), BDNF PA, superstructured host-guest hydrogel containing BDNF mimetic signal (host-guest BDNF PA hydrogel), and BDNF protein (BDNF). (FIG. 3B) Cell survival of neurons seeded on two-dimensional (2D) poly-D-lysine coated coverslips, host-guest hydrogel, the BDNF PA, and the host-guest BDNF PA hydrogel after 7 days in vitro (values normalized to total number of cells). (FIG. 3C) Imaris shadow projection of a neuron (MAP-2, green) growing through superstructure bundles (blue). (FIG. 3D) Depth-coded z-stack reconstructions showing cell infiltration on the host-guest hydrogel, the BDNF PA, and the host-guest BDNF PA hydrogel after 7 days in vitro. (FIG. 3E) Pixel depth analysis and normalized average intensity of MAP-2 under conditions described in (FIG. 3D); the area under the curve (AUC) is given with a standard deviation in arbitrary units (A.U.) for each hydrogel type. (FIG. 3F) Schematic representation of cell infiltration in the various hydrogels (*$P<0.05$, and **$P<0.01$, LSD test (FIG. 3B) (n=4), (FIG. 3E) (n=3)). The BDNF PA was co-assembled with the CD-E2 PA at 10 mol % (10 mol % BDNF PA, 10 mol % cyclodextrin PA, and 80 mol % E2 PA) and separately with the Ada-E2 PA (10 mol % BDNF PA, 10 mol % adamantane PA, 80% E2 PA). The two PAs were mixed in a 1:1 ratio to form a superstructure that incorporates the BDNF PA.

FIG. 4A-F. 3D printed cortical brain-like layered structures using superstructured inks. (FIG. 4A) Storage modulus (G'), loss modulus (G") and viscosity for the host-guest hydrogel and $E_2$ PA before and after high shear deformation. (FIG. 4B) Schematic representation of cortical lamina in the brain and a 3D printed version fabricated using cell-laden host-guest hydrogel inks (top), and method of fabrication (bottom). (FIG. 4C) Optical micrograph of a 3D printed pattern using the superstructured host-guest hydrogel and (FIG. 4D) the $E_2$ PA hydrogel labeled with different fluorophores in the following sequence from the outermost layer to the core: Cy3, Cy3+Cy5, Cy5, DAPI, and Cy3. (FIG. 4D) Optical micrograph of a 3D printed structure using the $E_2$ PA hydrogel with concentric layers labeled with TAMRA-$E_2$ PA (red), Alexa 488-$E_2$ PA (green), and DAPI+$E_2$ PA (blue). (FIG. 4E) 3D printed pattern using the host-guest superstructured hydrogel (layers 1, 2 and 4) or its bioactive form with BDNF PA (layer 2) with Vybrant™ DiO labeled neurons (green), and Yellow Celltrace™ labeled astrocytes (red) or mixtures of both cells: 1) astrocytes, 2) neurons 3) astrocytes and neurons, and 4) neurons. (FIG. 4F) Quantification of cell survival in a co-culture of neurons and astrocytes on a two-dimensional poly-D-lysine coated coverslip and within a 3D printed hydrogel scaffold containing the host-guest superstructured hydrogel (3 days in vitro, values normalized to total number of cells).

FIG. 5A-B. Adamantane and Cyclodextrin PA 100 mol % Analysis. (FIG. 5A) Cryo-TEM images of 100 mol % of the Adamantane PA (Ada PA, left) and the Cyclodextrin PA (CD PA, right). (FIG. 5B) Dynamic light scattering (DLS) spectra of 100 mol % Ada PA (left) and CD PA (right).

FIG. 7A-B. Fiber formation at differing PA co-assembly ratios by conventional TEM. TEM images of 100, 75, 50, 25 and 10 mol % of (FIG. 7A) Ada-PA with $E_2$ PA and (FIG. 7B) CD-PA with $E_2$ PA.

(FIG. 9A) Small angle x-ray scattering (SAXS)/mid angle x-ray scattering (MAXS) and (FIG. 9B) Wide angle x-ray scattering (WAXS) pattern of 100 mol % cyclodextrin PA (CD PA, Blue), 100 mol % adamantane PA (Ada PA, Red) and 100 mol % $E_2$ PA (Green).

(FIG. 11A) Representative 1H-NMR spectra for the titration between CD-$E_2$ PA and 1-adamantaneacetic acid, with the concentration of 1-adamantaneacetic acid increasing from the bottom to the top of the plot. The inset denotes the region of the spectrum used to calculate the binding constant. (FIG. 11B) Chemical structures of CD PA and 1-adamantaneacetic acid. The proton on 1-adamantaneacetic acid that was used to calculate the binding constant is labeled in red. (FIG. 11C) The binding isotherm for the titration experiment fit to a standard 1:1 host-guest binding model showing an association constant ($K_a$) of 434 $M^{-1}$.

(FIG. 12A) Representative 1H-NMR spectra for the titration between Ada-$E_2$ PA and β-cyclodextrin, with the concentration of β-cyclodextrin increasing from the bottom to the top of the plot. The inset denotes the region of the spectrum used to calculate the binding constant. (FIG. 12B) Chemical structures of Ada PA and β-cyclodextrin. The proton on β-cyclodextrin that was used to calculate the binding constant is labeled in red. (FIG. 12C) The binding isotherm for the titration experiment fit to a standard 1:1 host-guest binding model showing an association constant ($K_a$) of 3378 $M^{-1}$.

(FIG. 13A) Representative 1H-NMR spectra for the titration between β-cyclodextrin and 1-adamantaneacetic acid, with the concentration of 1-adamantaneacetic acid increasing from the bottom to the top of the plot. The inset denotes the region of the spectrum used to calculate the binding constant. (FIG. 13B) Chemical structures of β-cyclodextrin and 1-adamantaneacetic acid. The proton on 1-adamantaneacetic acid that was used to calculate the binding constant is labeled in red. (FIG. 13C) The binding isotherm for the titration experiment fit to a standard 1:1 host-guest binding model showing an association constant ($K_a$) of 395 $M^{-1}$.

(FIG. 14B) Comparison of different stoichiometric ratios of the Ada-PA relative to the CD-PA in the host-guest hydrogels at 1 wt % (n=1).

(FIG. 16A) Cryo-TEM of $C_{16}V_4A_2E_3$, $C_{16}V_4A_2E_3$-Ada, $C_{16}V_4A_2E_3$-CD, and $C_{16}V_4A_2E_3$-Mixed. (FIG. 16B) Circular dichroism spectra of samples in part (FIG. 16A).

FIG. 17A-C. Macroscopic characterization of $V_4$-modified host-guest PAs. (FIG. 17A) SEM micrographs of $C_{16}V_4A_2E_3$, $C_{16}V_4A_2E_3$-Ada, $C_{16}V_4A_2E_3$-CD, and $C_{16}V_4A_2E_3$-Mixed. (FIG. 17B) Storage (G') and loss (G") moduli of the samples described in part (FIG. 17A). (FIG. 17C) Thixotropy study showing storage modulus (G'), loss modulus (G") and viscosity for the $C_{16}V_4A_2E_3$ and $C_{16}V_4A_2E_3$-Mixed PAs under three consecutive intervals of steady state, high shear, and a resting state. *P<0.1, LSD test (FIG. 17B) (n=3).

FIG. 21A-B. Fluorescent images of the superstructured host-guest hydrogel+1 equivalent free adamantane and 2 equivalents free adamantane. Confocal micrograph z-stacks split into individual channels (Left to right): Cy3 functionalized adamantane PA (Red), Cy5 functionalized cyclodextrin PA (Green), and DyLight 405 functionalized $E_2$ PA (Blue) of the (FIG. 21A) superstructured host-guest hydrogel+1 equiv free adamantane (Free Ada) and (FIG. 21B) superstructured host-guest hydrogel+2 equiv free adamantane.

FIG. 22A-G. Characterization of the host-guest PA system with the incorporation of the BDNF PA. (FIG. 22A) Schematic representation of the inclusion of the BDNF mimetic PA into the adamantane-cyclodextrin superstructure forming system. (FIG. 22B) Cryo-TEM, (FIG. 22C) SAXS, (FIG. 22D) WAXS and (FIG. 22E) circular dichroism spectroscopy characterization of the Ada-$E_2$ PA+BDNF PA, CD-$E_2$ PA+BDNF PA and the BDNF superstructured mixture. (FIG. 22F) Rheology assessment of the host-guest BDNF PA hydrogel compared to the host-guest hydrogel without BDNF PA. (FIG. 22G) SEM micrograph of the BDNF PA mixture. (FIG. 22F) (n=2).

(FIG. 23A) Replicate of western blot of phosphorylated TrkB (p-TrkB), TrkB, and actin in neuronal cells exposed to starvation conditions (Strv), BDNF PA, host-guest BDNF PA superstructured material (host-guest BDNF), and BDNF protein (BDNF) in vitro. (FIG. 23B) Densitometry analysis of the western blot shown in (FIG. 23A). *P<0.05, and **P<0.01, LSD test (FIG. 23B) (n=3).

(FIG. 24A) Confocal micrographs of cells cultured on 3D gels of the $E_2$-PA, Ada-$E_2$ PA, CD-$E_2$ PA, host-guest hydrogel, BDNF PA, and host-guest BDNF PA hydrogel stained with calcein (Green) and propidium iodide (Red) for 7 days in vitro. (FIG. 24B) Percent cell survival quantification of images in (FIG. 24A) (values normalized to total number of cells). **P<0.01, LSD test (FIG. 24B) (n=4).

(FIG. 25A) G' and G" for Ada-E$_2$ PA, CD-E$_2$ PA, host-guest hydrogel, BDNF PA, and host-guest BDNF PA hydrogel using in vitro conditions of 1 wt % material and 25 mM Ca$^{2+}$. (FIG. 25B) Normalized average intensity of MAP-2 and pixel depth analysis of cell infiltration of cortical neurons on gels of the CD-E$_2$ PA, and the Ada-E$_2$ PA after 7 days in vitro. Area under the curve (AUC) displayed with the standard deviation, in arbitrary units (A.U.), for each gel type. (FIG. 25C) Depth-coded z-stack reconstructions showing cell infiltration on the CD-E$_2$ PA and Ada-E$_2$ PA gels after 7 days in vitro. (FIG. 25A) (n=3), (FIG. 25B) (n=3).

FIG. 26A-E. Shadow projection volume analysis of PA scaffolds. Shadow projections of PA scaffolds with E$_2$-405 dye labeled PA material to visualize material volume of the (FIG. 26A) E$_2$ PA (FIG. 26B) BDNF PA, (FIG. 26C) host-guest hydrogel and (FIG. 26D) host-guest BDNF PA hydrogel. (FIG. 26E) Quantification of the ratio of material volume to total scaffold volume for the three conditions. ****P<0.0001, LSD test (FIG. 26E) (n=3).

FIG. 27A-B. Host-guest hydrogel macroporous scaffold. Each material was extruded into a grid design to form a 20×20 mm macroporous scaffold. Images were taken directly after extrusion, at 24, and 72 hours (including fluorescence imaging) following extrusion to study if the materials were able to hold their shape. (FIG. 27A) The E$_2$ PA (E$_2$ PA+E$_2$-405 PA, prepared at 3 wt % and annealed) lost the definition of the structure during extrusion while (FIG. 27B) the host-guest PA hydrogel (CD-E$_2$ PA and Ada-E$_2$ PA+Ada-E$_2$-Cy3 PA, 3 wt % and annealed separately before being mixed 1:1 to create the host-guest PA hydrogel) exhibited a self-standing macroporous structure at t=0, t=24, and t=72 hrs.

(FIG. 28A) Ti2 Widefield micrograph and 3D reconstruction of the 3D printed host-guest hydrogel pictured in FIG. 4c. Labeled with fluorophores listed from outside in; Cy3, Cy3+Cy5, Cy5, DAPI, Cy3 and (FIG. 28B) photograph of the 3D printed host-guest hydrogel (FIG. 28C) Photograph of E$_2$ PA liquid ink printed in concentric circles taken immediately after printing.

(FIG. 32A) LCMS trace of adamantane PA [adamantane PA]=1 mg/mL, loading solvent; H$_2$O with 0.1% NH+OH (v/v), eluent; H$_2$O—CH$_3$CN gradient containing 0.1% HCOOH (v/v), column; Phenomenex Gemini 5 μm C18 110 Å LC column 150×1 mm. (FIG. 32B) ESI-mass spectra of adamantane PA. Elution volume 0.73-0.75 mL.

(FIG. 33A) LCMS trace of cyclodextrin PA [cyclodextrin PA]=1 mg/mL, loading solvent; H$_2$O with 0.1% NH+OH (v/v), eluent; H$_2$O—CH$_3$CN gradient containing 0.1% HCOOH (v/v), column; Phenomenex Gemini 5 μm C18 110 Å LC column 150×1 mm. (FIG. 33B) ESI-mass spectra of Cyclodextrin PA. Elution volume 0.595-0.605 mL.

(FIG. 34A) LCMS trace of BDNF PA [BDNF PA]=1 mg/mL, loading solvent; H$_2$O with 0.1% NH$_4$OH (v/v), eluent; H$_2$O—CH$_3$CN gradient containing 0.1% HCOOH (v/v), column; Phenomenex Gemini 5 μm C18 110 Å LC column 150×1 mm. (FIG. 34B) ESI-mass spectra of BDNF PA. Elution volume 0.9731-1.0127 mL.

DETAILED DESCRIPTION

1. Definitions

Figure 1D:
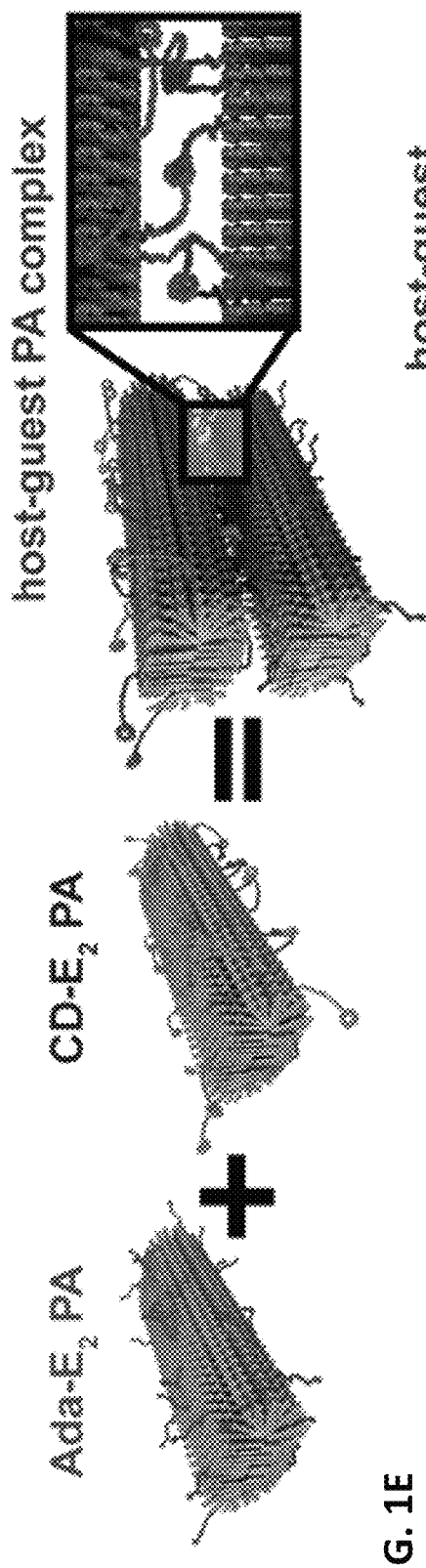

Although any methods and materials similar or equivalent to those described herein can be used in the practice or testing of embodiments described herein, some preferred methods, compositions, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the terms "comprise", "include", and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "artificial" refers to compositions and systems that are designed or prepared by man and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semiconservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the terms "peptide amphiphile" or "PA" are used interchangeably to refer to a molecule that, at a minimum, includes a hydrophobic segment, a structural peptide segment (e.g., β-sheet forming), and a charged peptide segment. The peptide amphiphile may express a net charge at physiological pH, either a net positive or negative net charge, or may be zwitterionic (i.e., carrying both positive and negative charges). The combination of hydrophobic segment, structural peptide segment, and charged peptide segment is also referred to herein as a "backbone".

The term "peptide amphiphile" is inclusive of a variety of types of PA described herein. For example, the term "peptide amphiphile" is inclusive of a "host peptide amphiphile" or a "host PA". A "host PA" is a peptide amphiphile that includes the minimum components above (e.g. a hydrophobic segment, a structural peptide segment, and a charged peptide segment), and additionally includes a host moiety. The host moiety may be any suitable moiety capable of participating in the formation of a complex with a "guest", which complex is referred to herein as a "host-guest complex" or a "guest-host complex". The term "peptide amphiphile" is also inclusive of a "guest peptide amphiphile" or a "guest PA", which refers to a PA that includes the hydrophobic segment, a structural peptide segment (e.g., β-sheet forming), and a charged peptide segment, and additionally includes a "guest" moiety. The guest moiety may be any suitable moiety that forms a complex with the host (e.g. forms a host-guest complex). The term "peptide amphiphile" is also inclusive of a "bioactive PA", which refers to a PA that includes a PA backbone (e.g. a hydrophobic segment, a structural peptide segment, and a charged peptide segment) conjugated to a bioactive moiety. As yet another example, the term "peptide amphiphile" includes a "filler" or a "diluent" PA, which are used interchangeably herein to refer to a PA that includes a hydrophobic segment, a structural peptide segment (e.g., β-sheet forming), and a charged peptide segment without an additional "host", "guest" or "bioactive" moiety.

As used herein and in the appended claims, the term "lipophilic moiety" or "hydrophobic moiety" refers to the moiety (e.g., an acyl, alkyl, ether, sulfonamide, or phosphodiester moiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in some embodiments, the hydrophobic component comprises a single, linear alkyl chain of the formula $C_8$-24. In other embodiments, the hydrophobic component comprises a single, linear acyl chain of the formula: $C_{n-1}H_{2n-1}C(O)$—where n=2-25. In some embodiments, a linear acyl chain is the lipophilic group (saturated or unsaturated carbons), palmitic acid. However, other lipophilic groups may be used such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD). In some embodiments, the structural peptide comprises $V_2A_2$. In other embodiments, the structural peptide comprises $V_3A_3$.

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues). In some embodiments, the charged peptide segment comprises $E_{2-4}$.

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, the term "nanofiber" refers to an elongated or threadlike filament (e.g., having a significantly greater length dimension that width or diameter) with a diameter typically less than 100 nanometers.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4. An exception is in the acidic environment in the vagina, which has a pH between 4.0 and 4.5.

As used herein, the term "supramolecular" (e.g., "supramolecular complex," "supramolecular interactions," "supramolecular fiber," "supramolecular system", "supramolecular polymer," etc.) refers to the non-covalent interactions between molecules (e.g., polymers, macromolecules, etc.) and the multicomponent assemblies, complexes, systems, and/or fibers that form as a result.

As used herein, the term "superstructure" refers to a bundle of supramolecular polymers. In some embodiments, a superstructure is formed as a result of a dynamic process referred to herein as "dynamic molecular exchange". The term "dynamic molecular exchange" which refers to a process involving spatial relocation of monomers (or monomer clusters) containing either "host" or "guest" moieties. Such a relocation optimizes the number of highly favorable host-guest contacts. This dynamic molecular exchange process and the resulting formation of a superstructure may be reversible. For instance, addition of oligonucleotide displacement strands, pH changes that diminish electrostatic interactions, etc. may disrupt the superstructure.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components As used herein, the terms "prevent," "prevention," and preventing" refer to reducing the likelihood of a particular condition or disease state (e.g., stress urinary incontinence, erectile dysfunction) from occurring in a subject not presently experiencing or afflicted with the condition or disease state. The terms do not necessarily indicate complete or absolute prevention. For example "preventing stress urinary incontinence" refers to reducing the likelihood of SUI occurring in a subject not presently experiencing or diagnosed with SUI. In order to "prevent stress urinary incontinence" a composition or method need only reduce the likelihood of *SUI*, not completely block any possibility thereof. "Prevention," encompasses any administration or application of a therapeutic or technique to reduce the likelihood of a disease developing (e.g., in a mammal, including a human). Such a likelihood may be assessed for a population or for an individual.

As used herein, the terms "treat," "treatment," and "treating" refer to reducing the amount or severity of a particular condition, disease state, or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the term "administration" refers to any suitable method of providing a composition described herein to a subject. Administration may be by any suitable method. For example, administration may occur by directly applying the composition to a tissue of the subject. For example, the composition may be placed directly on top of the tissue of the subject. Suitable routes of administrating the composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration. In some embodiments, the PA compositions are administered parenterally. In some embodiments, parenteral administration is by intrathecal administration, intracerebroventricular administration, or intraparenchymal administration. The PA compositions herein can be administered as the sole active agent or in combination with other pharmaceutical agents such as other agents used in the treatment of erectile dysfunction and/or stress urinary incontinence in a subject.

As used herein, the terms "co-administration" and "co-administering" refer to the administration of at least two agent(s) or therapies to a subject (e.g., a composition disclosed herein and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the terms "subject" and "patient" refer to any animal, such as a dog, cat, bird, livestock, and particularly a mammal, preferably a human. In some embodiments, the subject is a male. In other embodiments, the subject is a female.

2. Compositions and Superstructures

In some aspects, provided herein are compositions. The compositions comprise one or more peptide amphiphiles. The one or more peptide amphiphiles may interact with each other to form a supramolecular system. Accordingly, in some aspects, provided herein are supramolecular systems. In some embodiments, the supramolecular system is a superstructure. The "superstructures" described herein may also be referred to as "hierarchical superstructures". In some embodiments, provided herein are superstructures comprising a bioactive moiety. Superstructures that comprise a bioactive moiety are referred to herein as "bioactive superstructures" or "bioactive hierarchical superstructures".

In some embodiments, provided herein are bioactive hierarchical superstructures that form as a result of dynamic molecular exchange. This dynamic molecular exchange allows for the formation of bioactive hierarchical superstructures based on PA molecules designed to engage host-guest interactions. In some embodiments, the superstructures are designed to engage host-guest interactions between β-cyclodextrin and adamantane is a strong, reversible non-covalent interaction. This host-guest interaction may be useful for a wide range of biomedical applications including stimuli-responsive hydrogels, biosensing, drug release, 3D printing, and scaffold functionalization. Accordingly, this and other host-guest interactions may represent a viable tool to enhance mechanical properties of PA hydrogels, effectively functioning as crosslinks between fibers.

In one aspect, described herein is a bioactive PA system designed to exhibit dynamic exchange of monomers and also functionalized with β-cyclodextrin and adamantane moieties as a strategy to create reversible hierarchical superstructures. To introduce bioactivity in this system, the BDNF mimetic signal may be used. This combination of dynamic crosslinking and potential bioactivity could provide a 3D printing platform for spatially defined templates for populations of cells that can simulate the complexity of neural tissue for in vitro assays. Furthermore, this objective can be achieved without the need for additive molecules which may alter bioactivity of the materials used. Extruding neuronal cells is particularly challenging since the bio-ink carrier must be of appropriate softness to avoid shearing them while subsequently maintaining an appropriate stiffness so the construct maintains its shape. Described herein is a system that can combine bioactive chemical signaling and dynamic hierarchical superstructure formation to construct 3D printed self-supporting cell laden hydrogels.

In some embodiments, provided herein are superstructures comprising one or more peptide amphiphiles.

In some embodiments, the compositions and/or supramolecular systems (e.g. superstructures) described herein comprise one or more host peptide amphiphiles and one or more guest peptide amphiphiles. In some embodiments, the composition and/or superstructure further comprises one or more diluent peptide amphiphiles. In some embodiments, the host PA comprises a hydrophobic segment, a structural peptide segment, a charged peptide segment, and a host moiety. The host moiety may be any suitable moiety capable of forming a complex with a "guest". The complex between the host and the guest is referred to herein as a "host-guest complex" or a "guest-host complex". In some embodiments, the host is β-cyclodextrin.

In some embodiments, the guest PA comprises a hydrophobic segment, a structural peptide segment, a charged peptide segment, and a guest moiety. The guest moiety may be any suitable moiety capable of forming a complex with the host. In some embodiments, the host and the guest interact via non-covalent interactions to form the host-guest complex. In some embodiments, the guest moiety is adamantane. In some embodiments, the host moiety is β-cyclodextrin and the guest moiety is adamantane.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus). Accordingly, some embodiments described herein encompass peptide amphiphiles having a C-terminal moiety that may be selected from the group consisting of —H, —OH, —COOH, —CONH2, and —NH2.

In some embodiments, peptide amphiphiles comprise a hydrophobic segment (i.e. a hydrophobic tail) linked to a peptide. In some embodiments, the peptide comprises a structural peptide segment. In some embodiments, the structural peptide segment is a hydrogen-bond-forming segment, or beta-sheet-forming segment. In some embodiments, the peptide comprises a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules self-assemble (e.g., into cylindrical micelles (a.k.a., nanofibers)) to bury the lipophilic segment in their core and display the bioactive peptide on the surface. In some embodiments, the structural peptide undergoes intermolecular hydrogen bonding to form beta sheets that orient parallel to the long axis of the micelle. In some embodiments, the structural peptide displays weak intermolecular hydrogen bonding, resulting in a less rigid beta-sheet conformation within the nanofibers.

In some embodiments, compositions and superstructures described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises $E_{2-4}$. For example, in some embodiments an acidic peptide segment comprises EE. In some embodiments, an acidic peptide segment comprises EEE. In other embodiments, an acidic peptide segment comprises EEEE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural peptide segment. In some embodiments, the structural peptide segment is a beta-sheet-forming segment. In some embodiments, the structural peptide segment is rich in one or more of H, I, L, F, V, G, and A residues. In some embodiments, the structural peptide segment comprises an alanine- and valine-rich peptide segment (e.g., VVAA, VVVAAA, AAVV, AAAVVV, or other combinations of V and A residues, etc.). In some embodiments, the structural peptide segment comprises 4 or more consecutive A and/or V residues, or conservative or semi-conservative substitutions thereto. In some embodiments, the structural peptide segment comprises $V_2A_2$. In some embodiments, the structural peptide segment comprises an alanine and glycine-rich peptide segment (e.g. AAGG, AAAGGG, or other combinations of A and G residues, etc.). In some embodiments, the structural peptide segment comprises $A_2G_2$.

In some embodiments, the structural peptide segment comprises 4 or more consecutive non-polar aliphatic residues (e.g., alanine (A), valine (V), leucine (L), isoleucine (I), methionine (M)). In some embodiments, the structural peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and $C=O$ groups (e.g., $CH_2(O(CH_2)_2)_2NH$, $CH_2(O(CH_2)_2)_2NHCO(CH_2)_2CCH$, etc.). In some embodiments, a spacer or linker further comprises additional bioactive groups, substituents, branches, etc. In some embodiments, the linker segment is a single glycine (G) residue. In some embodiments, the linker segment is multiple glycine residues (e.g. 2, 3, 4, 5, 6, 7, 8, or more than 8 glycine residues. In some embodiments, the linker segment is 6 glycine residues.

In some embodiments, the linker segment comprises 1-20 repeating polyethylene glycol (PEG) units. In some embodiments, the linker segment comprises 1, 2, 3, 4, 5, 6, 7, 8, 9, 10, 11, 12, 13, 14, 15, 16, 17, 18, 19, or 20 repeating PEG units. In some embodiments, the linker segment comprises 5-15 PEG units. In some embodiments, the linker segment comprises 10 PEG units. In some embodiments, the linker segment comprises a combination of glycine residues and PEG units.

In some embodiments, the linker segment conjugates the guest moiety, the host moiety, or the bioactive moiety to the PA backbone. In some embodiments, the linker segment conjugates the guest moiety, the host moiety, or the bioactive moiety to the charged peptide segment of the PA backbone. For example, in some embodiments the linker segment comprises 1-20 repeating PEG units and conjugates the host moiety (e.g. β-cyclodextrin) to the PA backbone (e.g. to the charged peptide segment of the PA backbone). In some embodiments, the host peptide amphiphile comprises the sequence $C_8\text{-}24V_2A_2E_4PEG_{10}$-β-cyclodextrin.

In some embodiments, the linker segment comprises one or more glycine residues and conjugates the guest moiety to the PA backbone. For example, in some embodiments the linker segment comprises 1, 2, 3, 4, 5, 6, 7, 8, 9, or 10 glycine residues and conjugates the guest moiety to the PA backbone. In some embodiments, the linker segment comprises 4-6 glycine residues and conjugates the guest moiety (e.g. adamantane) to the charged peptide segment of the PA backbone. In some embodiments, the guest peptide amphiphile comprises the sequence $C_{8\text{-}24}V_2A_2E_4G_6$-adamanatane.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural peptide segment, bioactive segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural peptide segment (e.g., comprising VVAA, AAGG, or VEVA); and (c) a charged segment (e.g., comprising EE, EEE, EEEE, etc.). In some embodiments, any PAs within the scope described herein, comprising the components described herein, or within the skill of one in the field, may find use herein.

In some embodiments, peptide amphiphiles comprise a bioactive moiety. In some embodiments, the bioactive moiety is the most C-terminal or N-terminal segment of the PA. In some embodiments, the bioactive moiety is attached to the end of the charged segment. In some embodiments, the bioactive moiety is conjugated to the end of the charged segment by a suitable linker, as described above. In some embodiments, the bioactive moiety is exposed on the surface of an assembled PA structure (e.g., nanofiber). A bioactive moiety is typically a peptide, but is not limited thereto.

In some embodiments, the bioactive moiety is a growth factor or a growth factor mimetic. The term "mimetic' as used herein refers to an entity that mimics the activity of the bioactive moiety (e.g. the growth factor). In some embodiments, the mimic may comprise a peptide sequence that mimics the receptor binding epitope of the bioactive moiety (e.g. the growth factor).

Non-limiting examples of suitable growth factor proteins include adrenomedullin, angiopoetin, autocrine motility factor, bone morphogenic proteins (e.g. BMP-2, BMP4), ciliary neurotrophic factors (e.g., ciliary neutotrophic factor, leukemia inhibitory factor, interleukin-6), colony-stimulating factors (e.g. macrophage colony-stimulating factor, granulocyte colony-stimulating factor, granulocyte macrophage colony-stimulating factor), epidermal growth factor, ephrins (e.g., ephrin $A_1$, ephrin $A_2$, ephrin $A_3$, ephrin $A_4$, ephrin $A_5$, ephrin B1, ephrin B2, ephrin B3), erythropoietin, fibroblast growth factors, fetal bovine somatotrophin, glial cell line derived neurotrophic factor, neurturin, persephin, artemin, growth differentiation factors (e.g., GDF9), hepatocyte growth factor, hepatoma-derived growth factor, insulin, insulin-like growth factors (e.g., IGF-1, IGF-2), interleukins (e.g., IL-1, IL-2, IL-3, IL-4, IL-5, IL-6, IL-7), keratinocyte growth factor, migration-stimulating factor, macrophage-stimulating protein, myostatin, neuregulins (e.g., NRG1, NRG2, NRG3, NRG4), neurotrophins (e.g., brain-derived neurotrophic factor (BDNF), nerve growth factor, NT-3, NT-4), placental growth factor, platelet-derived growth factor, renalase, T-cell growth factor, thrombopoetin, transforming growth factors (e.g., TGF-α, TGF-β), tumor necrosis factors (e.g., TNF-α), vascular endothelial growth factor (VEGF), sonic hedgehog protein, or Wnt signaling pathway proteins. Selection of the appropriate growth factor may depend on the desired use of the composition or nanostructure comprising the bioactive moiety.

In some embodiments, the bioactive moiety is a neurotrophin or a neurotrophin mimetic. The term "neurotrophin" is used herein to refer to a class of growth factor that play a role in cell survival, differentiation, and/or growth. In some embodiments, bioactive moiety is a neurotrophic factor or a mimetic thereof. The term "neurotrophic factor" refers to a secreted protein that promotes survival of neurons. In some embodiments, the bioactive moiety is nerve growth factor or a mimetic thereof, brain-derived neurotrophic factor or a mimetic thereof, neurotrophin-3 or a mimetic thereof, or neurotrophin-4 or mimetic thereof. In some embodiments, the bioactive moiety is a steroid or a mimetic thereof, such as dehydroepiandrosterone (DHEA) or DHEA sulfate, or a mimetic thereof.

In some embodiments, the bioactive moiety is brain derived neurotrophic factor (BDNF) or a BDNF mimetic peptide. In some embodiments, the bioactive moiety is the BDNF mimetic peptide with the following structure:

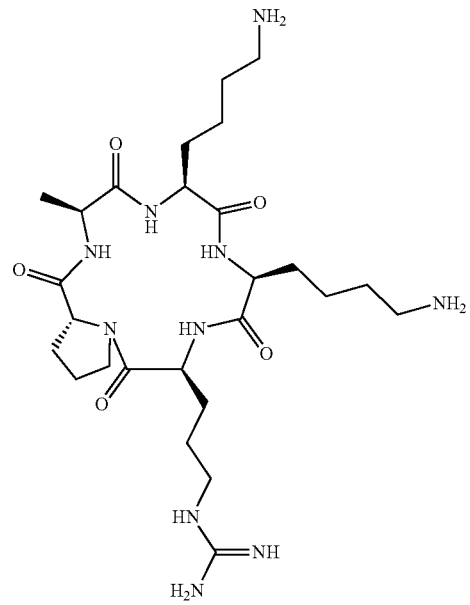 [SMILES: C[C@@H]1NC(=O)[C@H]2CCCN2C(=O)[C@H](CCCNC(=N)N)NC(=O)[C@H](CCCCN)NC(=O)[C@H](CCCCN)NC1=O]

In some embodiments, bioactive peptide amphiphile comprises the PA backbone sequence $C_8$-$24V_2A_2E2$-4. In some embodiments, the PA backbone sequence is linked to the BDNF or BDNF mimetic peptide by a linker comprising 1-10 repeating PEG units (e.g. 6 PEG units). In some embodiments, the linker additionally comprises one or more glycine residues. In some embodiments, the linker comprises 6 PEG units and a glycine residues. In some embodiments, the bioactive PA comprises the sequence $C_8$-$24V_2A_2E_4PEG_6$-BDNF mimetic peptide.

In some embodiments, a peptide amphiphile comprises (e.g., from C-terminus to N-terminus or from N-terminus to C-terminus): bioactive peptide (e.g., BDNF mimetic peptide)-charged segment (e.g., comprising $E_{2-4}$, etc.)—structural peptide segment (e.g., comprising $V_2A_2$, $A_2G_2$, $VEVA_2$, etc.)-hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., BDNF mimetic peptide)-flexible linker (e.g. comprising glycine residues, PEG units, or a combination thereof etc.)-charged segment (e.g., comprising $E_{2-4}$, etc.)—structural peptide segment (e.g., comprising $V_2A_2$, $A_2G_2$, $VEVA_2$, etc.)-hydrophobic tail (e.g., comprising an alkyl chain of 8-24 carbons).

In some embodiments, a PA further comprises an attachment segment or residue (e.g., K) for attachment of the hydrophobic tail to the peptide portion of the PA. In some embodiments, the hydrophobic tail is attached to a lysine side chain.

In some embodiments, provided herein are supramolecular assemblies assembled from the peptide amphiphiles described herein. In some embodiments, the supramolecular assembly is a superstructure. In some embodiments, the properties of the peptide amphiphiles lead to formation of a soft gel, referred to herein as a hydrogel. Accordingly, in some embodiments provided herein is a hydrogel comprising a superstructure as described herein. For example, in some embodiments provided herein is a hydrogel comprising a superstructure, wherein the superstructure comprises a host PA and a guest PA as described herein. The superstructure may further comprise one or more diluent PAs. The superstructure may further comprise one or more bioactive PAs. The superstructure is a bundle of supramolecular polymers formed at least in part by non-covalent interactions between the host moiety and the guest moiety of the host and guest PA, respectively. The superstructure may also be formed as a result of dynamic molecular exchange. The superstructure formation may be reversible, such as by addition of one or more disrupting peptides, changing pH, etc.

In some embodiments, the superstructure comprises one or more bioactive PAs. The bioactive moiety may be displayed on the surface of the superstructure.

In some embodiments, the amounts of host PA, guest PA, diluent PA, and/or bioactive PA may determine the characteristics of the supramolecular assemblies containing the same. In some embodiments, compositions and/or superstructures comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) diluent PAS. In some embodiments, compositions and/or superstructures comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) acidic diluent PAs. In some embodiments, compositions and/or superstructures comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) basic diluent PAs. In some embodiments, the ratio of diluent PA to host, guest, and/or bioactive PAs in a composition or supramolecular assembly determines the mechanical characteristics (e.g., liquid or gel) of the assembly and under what conditions the composition will adopt various characteristics (e.g., gelling upon exposure to physiologic conditions, liquifying upon exposure to physiologic conditions, etc.).

Peptide amphiphile (PA) nanofiber solutions may comprise any suitable combination of PAs. In some embodiments, at least 0.05 mg/mL (e.g., 0.10 mg/ml, 0.15 mg/ml, 0.20 mg/ml, 0.25 mg/ml, 0.30 mg/ml, 0.35 mg/ml, 0.40 mg/ml, 0.45 mg/ml, 0.50 mg/ml, 0.60 mg/ml, 0.70 mg/ml, 0.80 mg/ml, 0.90 mg/ml, 1.0 mg/ml, or more, or ranges therebetween), of the solution is a diluent PA. In some embodiments, at least 0.25 mg/mL of the solution is a diluent PA. In some embodiments, a diluent PA is a non-bioactive PA molecule having highly charged glutamic acid residues on the terminal end of the molecule (e.g., surface-displayed end). These negatively charged PAs allow for the gelation to take place between nanofibers via ionic cross-links. In some embodiments, a diluent PA is a non-bioactive PA molecule having highly charged lysine residues on the terminal end of the molecule (e.g., surface-displayed end). These positively charged PAS allow for the gelation to take place under basic conditions. The diluent PAs provide the ability to incorporate other bio-active PAs molecules into the nanofiber matrix while still ensuring the ability of the nanofibers solution to gel. In some embodiments, the solutions are annealed for increased viscosity and stronger gel mechanics. These diluent PAs have sequences are described in, for example, U.S. Pat. No. 8,772,228 (e.g., $C_{16}$-VVVAAAEEE), which is herein incorporated by reference in its entirety. In some embodiments, the diluent PA comprises the sequence $C_{8-24}V_2A_2E_2$.

In some embodiments, compositions and/or superstructures comprise 1-20% bioactive PA. In some embodiments, the compositions and/or superstructures comprise 1-20% host PA. In some embodiments, the compositions and/or superstructures comprise 1-20% guest PA. In some embodiments, the compositions comprise 80% diluent PA.

In some embodiments, a superstructure is formed by making a first composition comprising a host PA and a bioactive PA. The host PA and the bioactive PA interact to form a supramolecular assembly. A second composition may be made comprising a guest PA and a bioactive PA. The guest PA and the bioactive PA interact to form a supramolecular assembly. The first composition and the second composition may be combined, thereby forming a superstructure at least in part via interactions between the host moiety and the guest moiety. This is shown, for example, in FIG. 22A. The first composition may comprise 10% bioactive PA, 10% host PA, and 80% diluent PA. The second composition may comprise 10% bioactive PA, 10% guest PA, and 80% diluent PA. Accordingly, the superstructure formed as a result of combining the two compositions may comprise 10% bioactive PA, 5% host PA, 5% guest PA, and 80% diluent PA.

In some embodiments, provided herein is a hydrogel comprising a supramolecular assembly (e.g. superstructure) as described herein. In some embodiments, the hydrogel may be 3-D printed. In some embodiments, the hydrogel may be 3-D printed onto a suitable surface, without the need for additive molecules which may otherwise alter bioactivity of the materials used. For example, in some embodiments, the hydrogel may be 3-D printed onto a suitable surface without adding a layer of divalent cations to the printing surface. In some embodiments, the hydrogel may be 3-D printed in multiple layers (e.g. concentric layers). In some embodiments, each layer may comprise a supramolecular assembly containing the same bioactive PA. In some embodiments, each layer may comprise a supramolecular assembly containing a different bioactive PA. For example, different bioactive moieties may be selected to promote cell migration, differentiation, etc. Such embodiments may be useful, for instance, for modeling the multiple layers of a given tissue. For example, the methods described herein may be used to facilitate hydrogels modeling the multiple layers of the brain cortex.

In some embodiments, the hydrogel may further comprise one or more cells. For example, the hydrogel may comprise BDNF or a BDNF mimetic peptide as the bioactive moiety, which may therefore be useful for hydrogels containing neuronal cells and/or glial cells. For example, in some embodiments the hydrogel may additionally contain neuronal cells. As another example, the hydrogel may additionally contain glial cells. In some embodiments, the hydrogel may comprise a BDNF mimetic peptide as the bioactive moiety, which may facilitate infiltration of neuronal cells within the hydrogel.

In some aspects, provided herein is an injectable biomaterial, called a peptide amphiphile (PA), that has overcome a number of challenges which face other systems designed to mimic the extracellular matrix (ECM) for tissue regeneration applications. This work uses reversible host-guest noncovalent interactions of cyclodextrin and adamantane respectively to produce self-assembly driven porosity analogous to that of the natural ECM. The exchange dynamics observed in supramolecular PA nanofibers results in the enrichment of functionalized PA molecules and as a consequence the self-assembly of hierarchical superstructures in the system. These superstructures can be reversed through the addition of biocompatible chemical agents to block the host-guest interaction between PA fibers. These superstructures are shear thinning and have demonstrated to be highly amenable to 3D bio-printing of well-defined architectures, maintaining high cell viability throughout the process. Further to this, the incorporation of the superstructure system with a bioactive PA, suitable for neuronal tissue regeneration, resulted in enhanced neurite growth and maturation in the scaffold. The ability for this system to create self-assembly mediated porosity, combined with bioactive epitopes suitable for cell signaling and its applications in bioprinting make it a true ECM mimetic material, with vast applications in regenerative medicine and tissue engineering.

The invention described herein is highly amenable to a range of tissue regeneration applications as this material can be incorporated with cells, provide important chemical and mechanical cues to cells while forming a free standing 3D microenvironment without the addition of crosslinking agents or gelling solutions. The self-assembly driven porosity in this hydrogel scaffold resulting from molecular exchange dynamics of the supramolecular nanofibers is difficult to achieve through other methods, materials or techniques.

EXAMPLES

Example 1

Results & Discussion

Design and Characterization of Host-Guest Modified Peptide Amphiphile Supramolecular Polymers Two new PA molecules functionalized to display either a β-cyclodextrin host or an adamantane guest were synthesized. Considerations in the design of both PAs were to position the host and guest moieties away from the surface of the PA nanofibers, and to promote dynamic molecular exchange among nanofibers to spontaneously create hierarchical structures. A polyethylene glycol (PEG$_{10}$) spacer was chosen to link β-cyclodextrin to PA molecules based on its hydrophilicity and molecular flexibility (FIG. 1a).[8, 31-33] Since adamantane is much more hydrophobic, six glycine residues were used as a linker to minimize this moiety folding back and interacting with the hydrophobic core of PA nanofibers (FIG. 1b). Both the cyclodextrin PA (CD PA) and adamantane PA (Ada PA) had the same chemical sequence conjugated to the linker and host or guest moieties, namely a 16-carbon alkyl tail followed by the peptide sequence $V_2A_2E_4$. The E residues in the sequence ensured aqueous solubility for the 100 mol % Ada PA and CD PA molecules. Furthermore, it was hypothesized that the high charge of the PA molecules provided by the $E_4$ sequence would facilitate dynamic exchange due to repulsive forces and thus enable reorganization into hierarchical assemblies.[11] To prevent overcrowding among host and guest moieties and improve their display on nanofiber surfaces, the CD PA and Ada PA were co-assembled with a diluent PA with the sequence $C_{16}V_2A_2E_2$ PA ($E_2$ PA) (FIG. 1c). An $E_2$ PA molecule was chosen because it forms robust nanoribbons and can be co-assembled with many other PA sequences displaying bioactive epitopes.[35] The CD PA and Ada PA solutions were prepared separately with or without $E_2$ PA in 125 mM NaCl and 3 mM KCl, annealed at 80° C. for 30 min, and slowly cooled to drive them to the thermodynamically favored formation of long fibers. These two solutions were then mixed 1:1 by volume to allow the host-guest complex to form among nanofibers (FIG. 1d). The molecular schematic in FIG. 1d illustrates formation of the host-guest complex between the two supramolecular co-assemblies before any molecular exchange would enable the formation of superstructures.

Figure 1E:
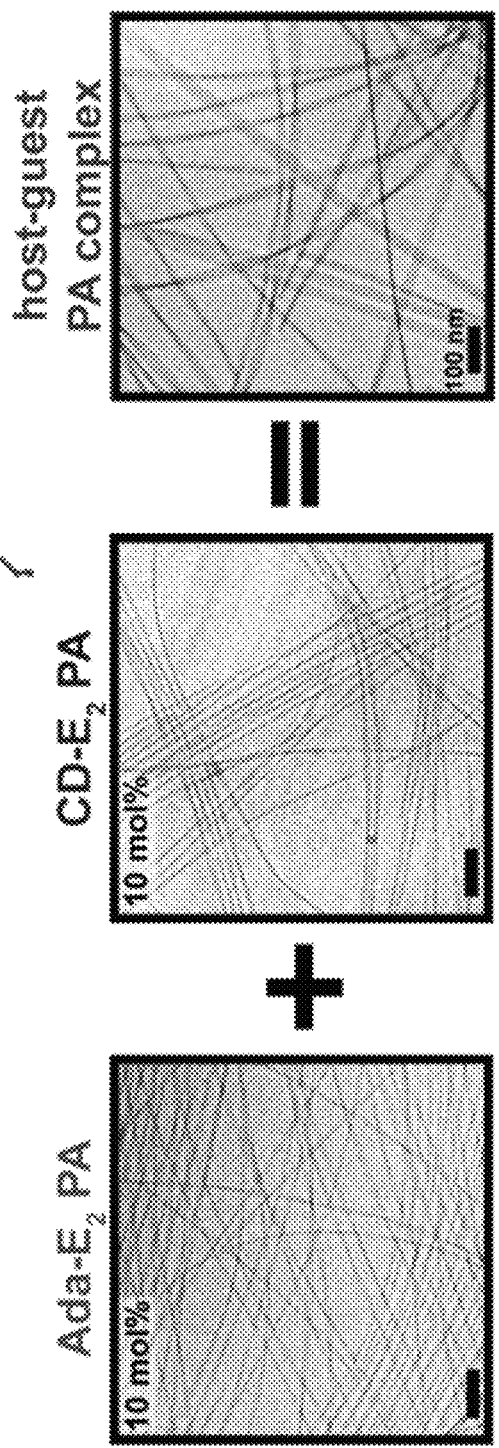
Figure 1F:
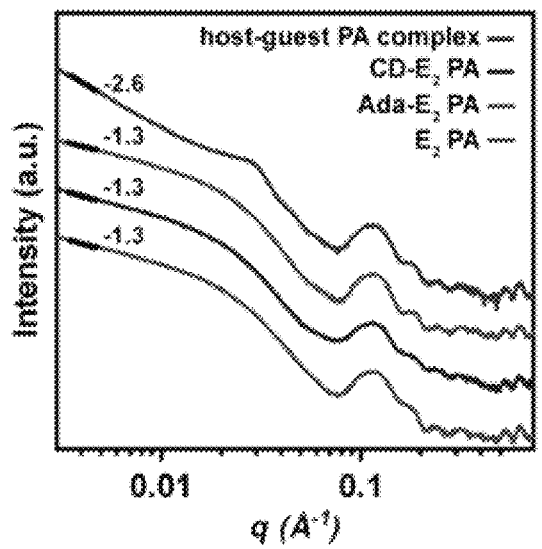
Figure 1G:
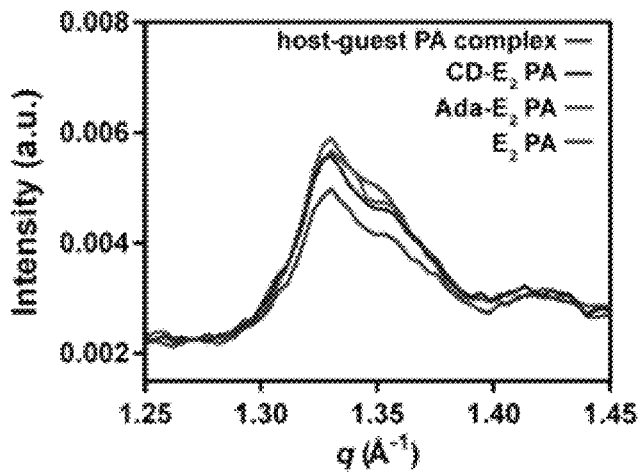
Figure 1H:
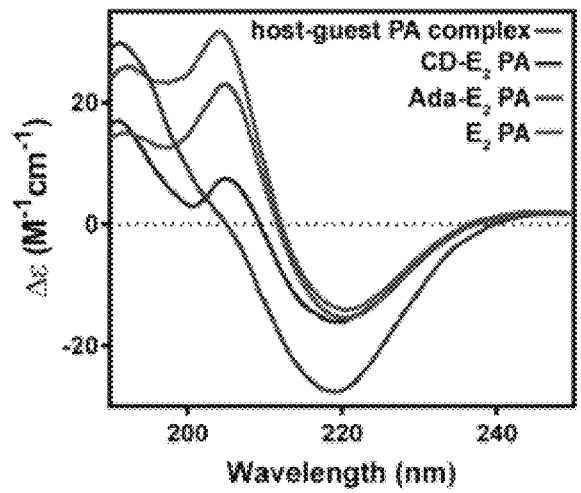
Figures 6A, 6B:
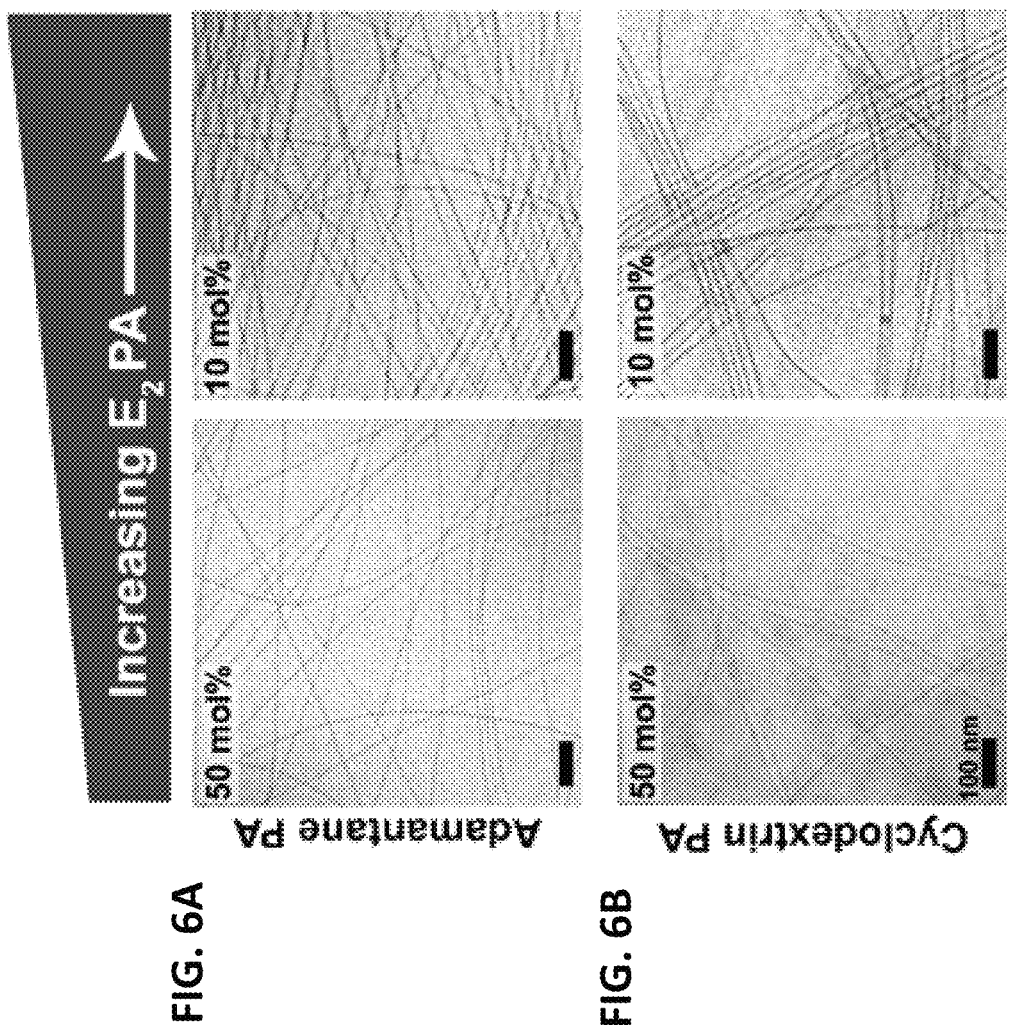
FIG. 6A-B. Fiber formation at differing PA co-assembly ratios by cryo-TEM. Cryo-TEM images of 50 mol % (left) and 10 mol % (right) of (FIG. 6A) the Adamantane PA (Ada PA) co-assembly and (FIG. 6B) the Cyclodextrin PA (CD PA) co-assembly with $E_2$ PA.
Figure 8:
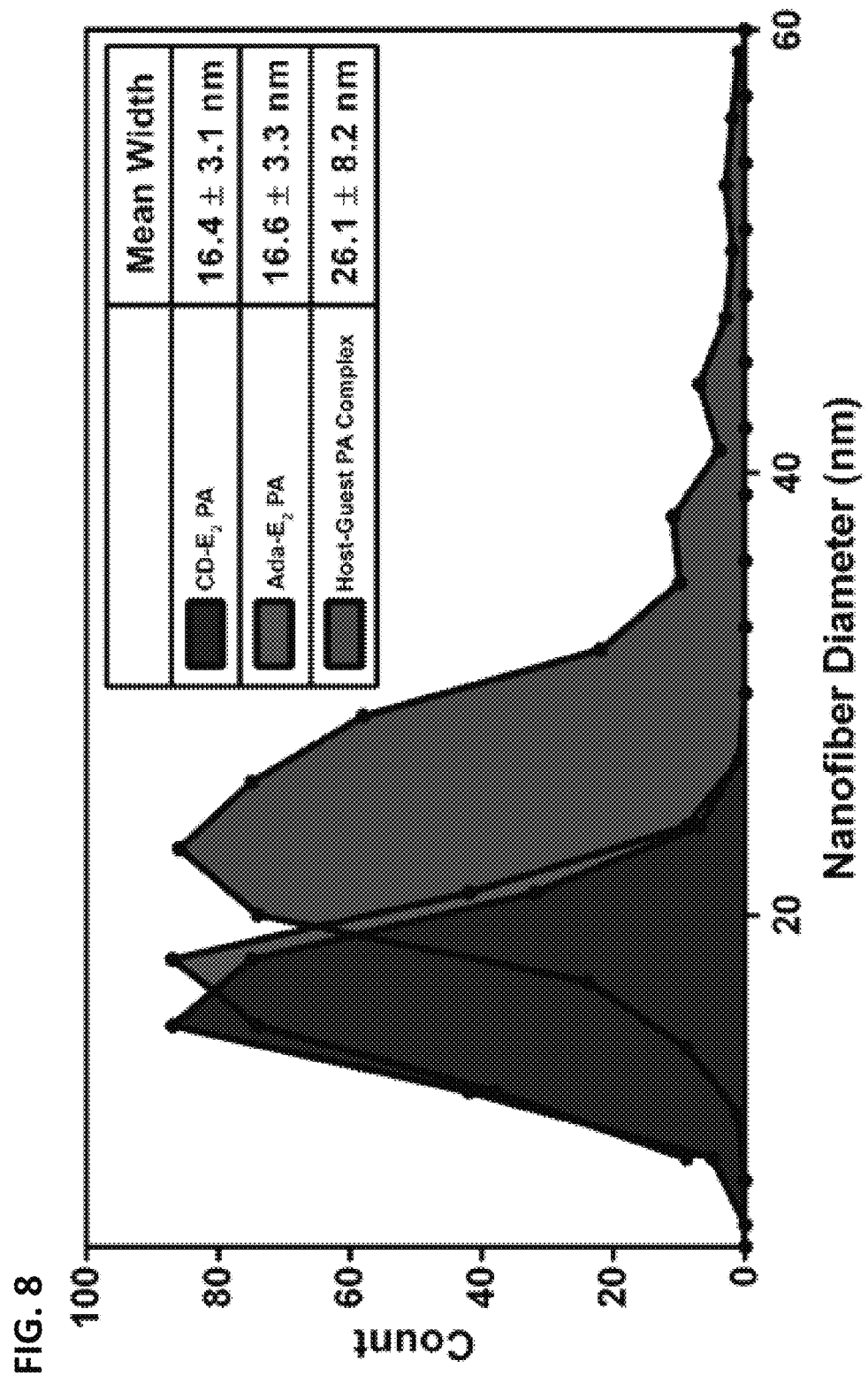
FIG. 8. Measurement of nanofiber diameters. Measurement of nanofiber diameter including the mean and standard deviation, in nm, of the CD-$E_2$ PA, Ada-$E_2$ PA, and Host-Guest PA Complex from representative Cryo-TEM images.
Figure 9A:
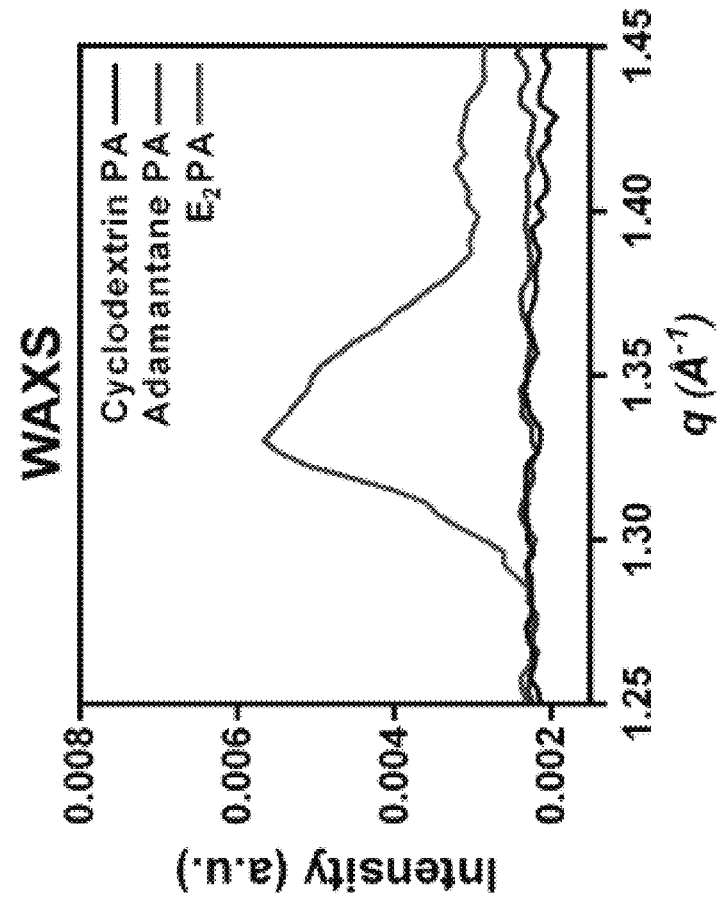
FIG. 9A-B. X-ray scattering of 100 mol % peptide amphiphiles.
Figure 9B:
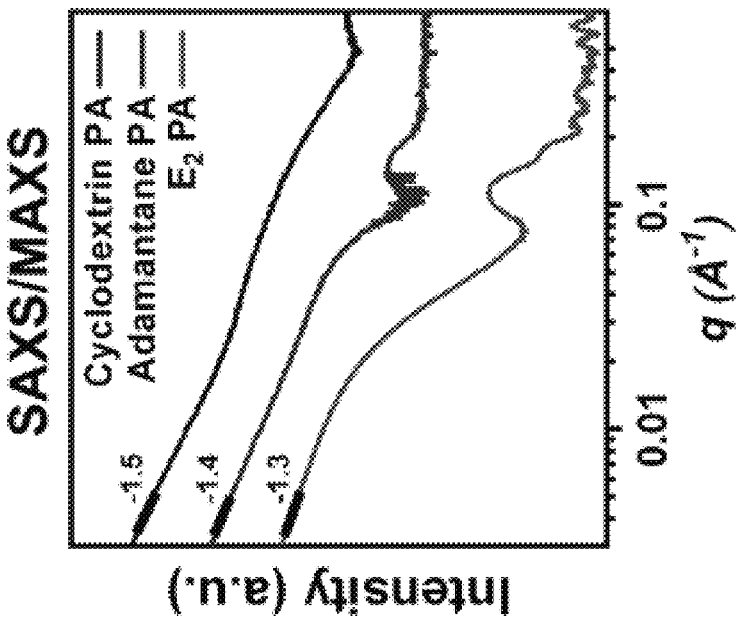
Figure 10:
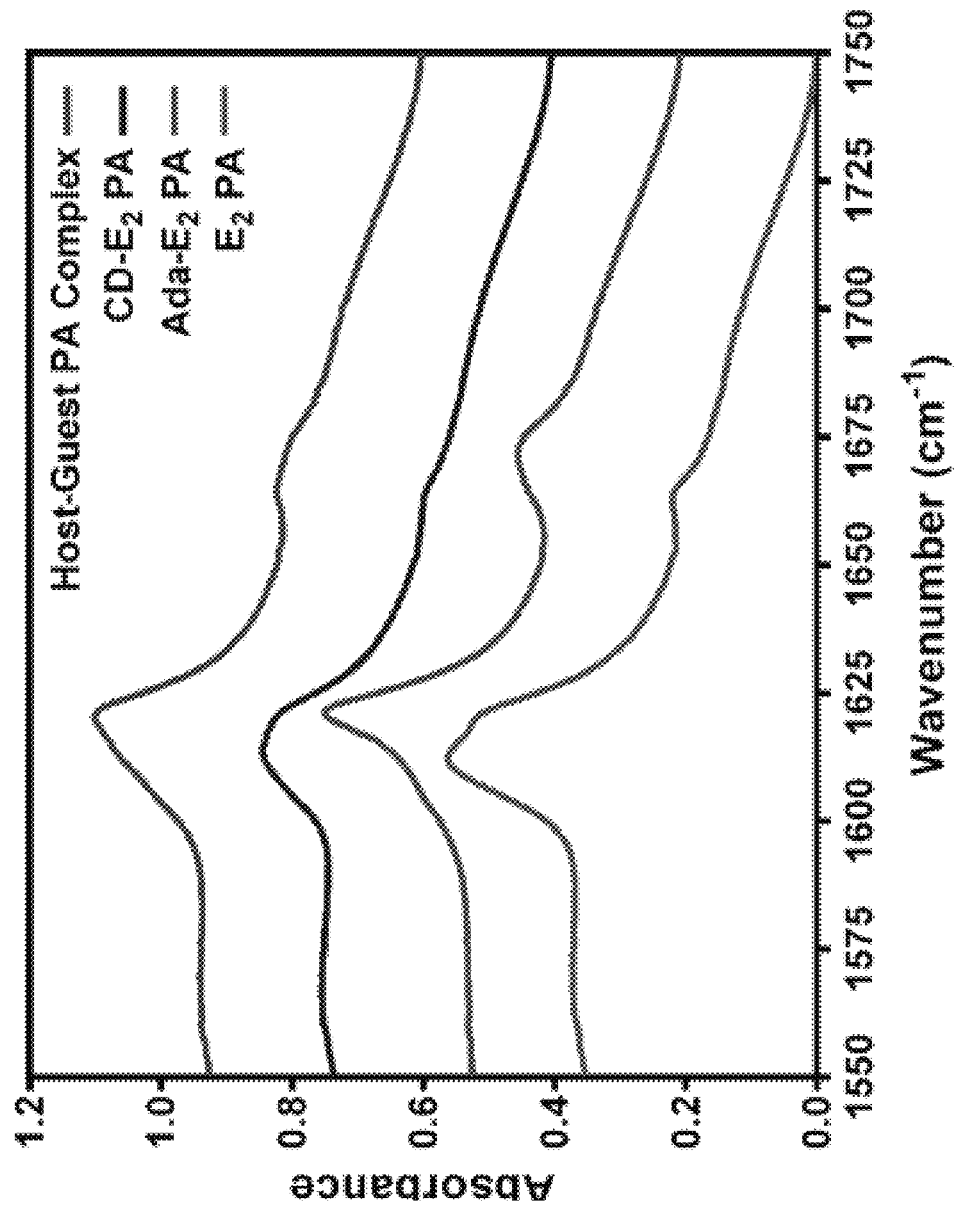
FIG. 10. Fourier-transform infrared (FTIR) spectroscopy of peptide amphiphiles. FTIR spectra of the $E_2$ PA, Ada-$E_2$ PA, CD-$E_2$ PA and the Host-Guest PA Complex.

Cryogenic transmission electron microscopy (Cryo-TEM) was used to visualize the host- and guest-modified supramolecular polymers co-assembled with $E_2$ at compositions varying from 0 to 100 mol %. Neither 100 mol % CD PA nor 100 mol % Ada PA exhibited formation of nanofibers through one-dimensional supramolecular polymerization (FIG. 5a). Dynamic light scattering (DLS) data indicated that the Ada PA formed micelle-like structures with a diameter distribution centered at 9 nm, with both PAs also forming structures greater than 300 nm in diameter suggesting the presence of some larger PA aggregates (FIG. 5b). When $E_2$ PA was added to the CD PA and Ada PA, the formation of long one-dimensional nanoribbons with monodisperse widths was observed using cryo-TEM in 10 mol % co-assemblies (10 mol % adamantane or cyclodextrin PA and 90 mol % $E_2$ PA) (FIG. 6). Furthermore, it was evident that co-assembly ratios above 75 mol % of the functionalized PA significantly disrupted fiber formation as observed by conventional TEM (FIG. 7). Therefore, a 10 mol % co-assembly ratio of the CD PA and Ada PA with $E_2$ PA was used for all subsequent experiments and these supramolecular polymers are referred to as CD-$E_2$ PA and Ada-$E_2$ PA, respectively. Cryo-TEM of CD-$E_2$ PA, Ada-$E_2$ PA, and the mixture of both supramolecular polymers revealed the formation of ribbon-like structures (FIG. 1e). The approximate average width of the CD-$E_2$ PA and Ada-$E_2$ PA assemblies was 16±3 nm and 17±3 nm, respectively, and the mixture of both was found to form wider ribbons measuring on average 26±8 nm in width (FIG. 8). It was hypothesized that the observed increase in fiber width could be due to host-guest interactions among the ribbon-shaped supramolecular polymers. This was further investigated using synchrotron small angle x-ray scattering (SAXS, FIG. 1f). The $E_2$ PA, CD-$E_2$ PA, and Ada-$E_2$ PA exhibited a slope of −1.3 in the Guinier region consistent with the presence of thin ribbon structures.[37] Consistent with cryo-TEM observations, the mixture of host and guest PAs had a slope of −2.6, indicative of wider ribbons which presumably form as a result of complex formation and bundling of the supramolecular polymers. Furthermore, there was a clear emergence of a Bragg peak at a q value of 0.0254 Å$^{-1}$ corresponding to a d-spacing of approximately 24.7 nm, similar to the average dimension observed in Cryo-TEM images, consistent with the formation of a uniform hierarchical assembly resulting from this interaction. Wide-angle synchrotron x-ray scattering (WAXS) measurements confirmed the presence of β-sheets in the interior of the assemblies with a peak at approximately 1.33 Å$^{-1}$ corresponding to a d-spacing of 4.72 Å in all cases except for the non-ribbon forming 100 mol % CD PA and Ada PA samples (FIG. 1g and FIG. 9). This d-spacing is considered typical of β-sheet secondary structures reported for many amyloid and peptide fibrillar assemblies.[38-40] Circular dichroism spectroscopy further confirmed the presence of β-sheet secondary structure in the $E_2$ PA, Ada-$E_2$ PA, CD-$E_2$ PA, and also within the host-guest PA complex sample (FIG. 1h). An apparent red shift in the spectra was observed relative to those in planar β-sheets with a maximum at 195 nm and a minimum at 218 nm.[41] This red shift has been previously attributed to an increase in the twist within anti-parallel β-sheets and we propose this is also occurring in our system.[42-44] Finally, Fourier-transform infrared spectroscopy (FTIR) also supported the presence of β-sheet secondary structure, revealing the expected absorbance peak at approximately 1625 cm$^{-1}$ for all structures corresponding to the characteristic amide I band (FIG. 10).[45] These observations establish the incorporation of the host-guest moieties in the PA supramolecular polymers investigated here does not disrupt supramolecular assembly.

Figure 11A:
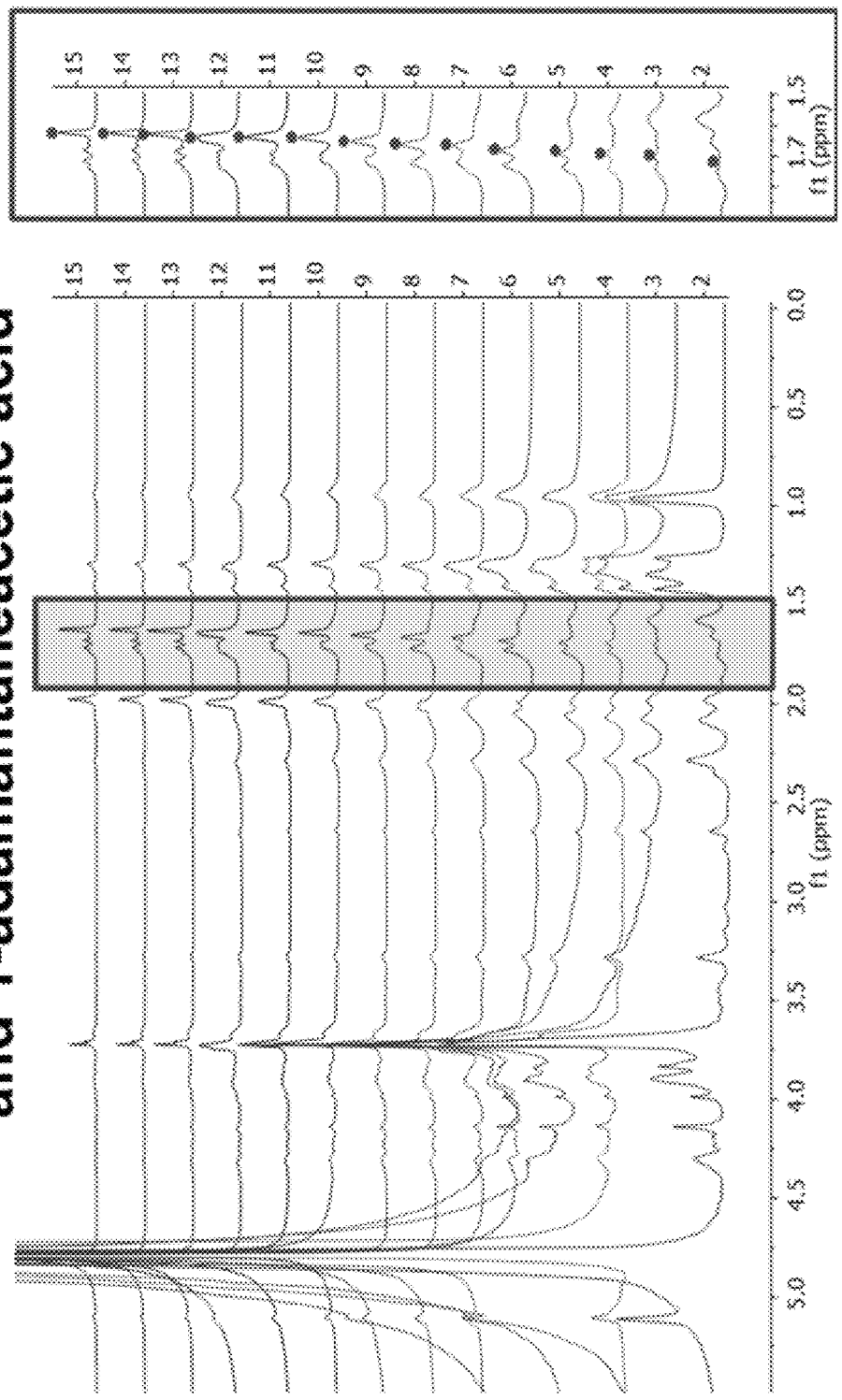
FIG. 11A-C. Determination of CD-$E_2$ PA and 1-adamantaneacetic acid binding constant.
Figure 11B:
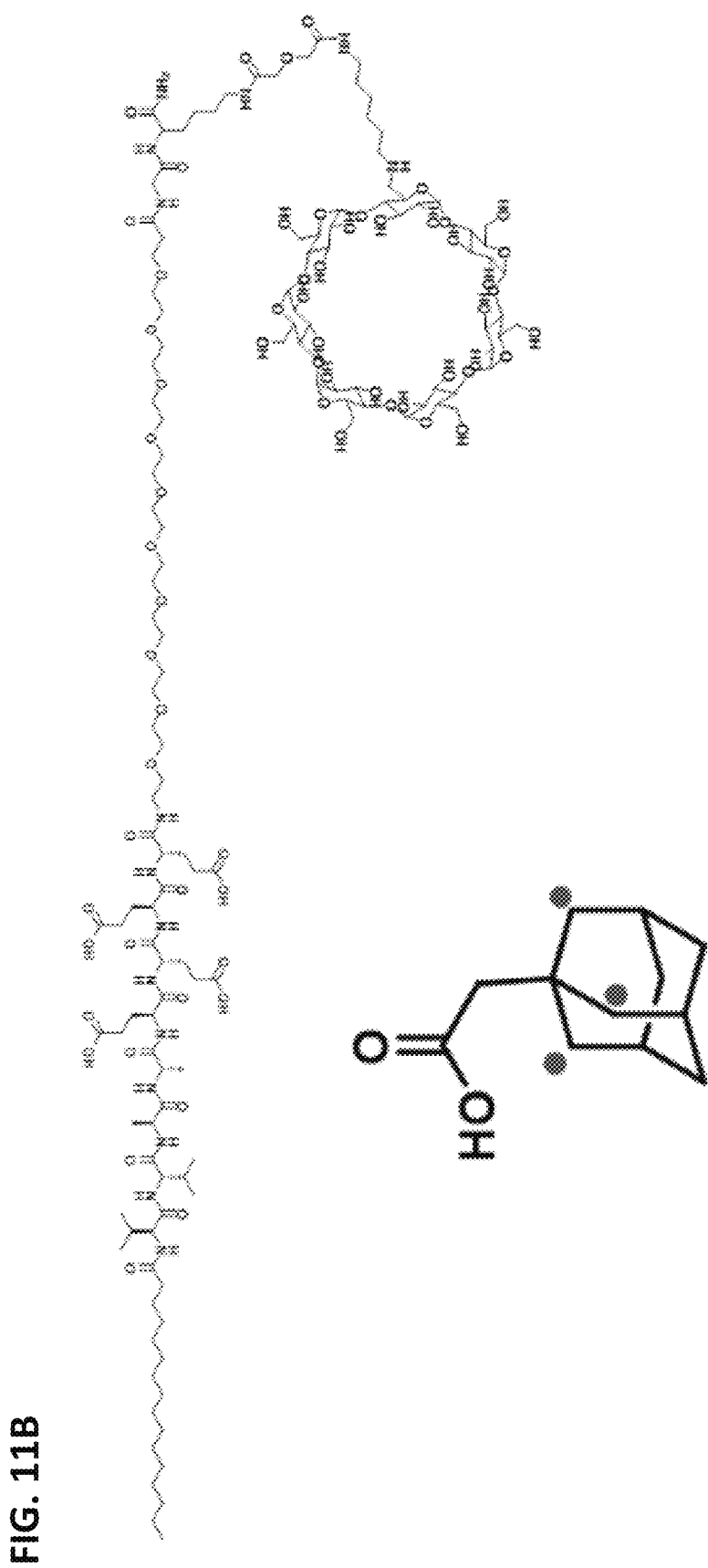
Figure 11C:
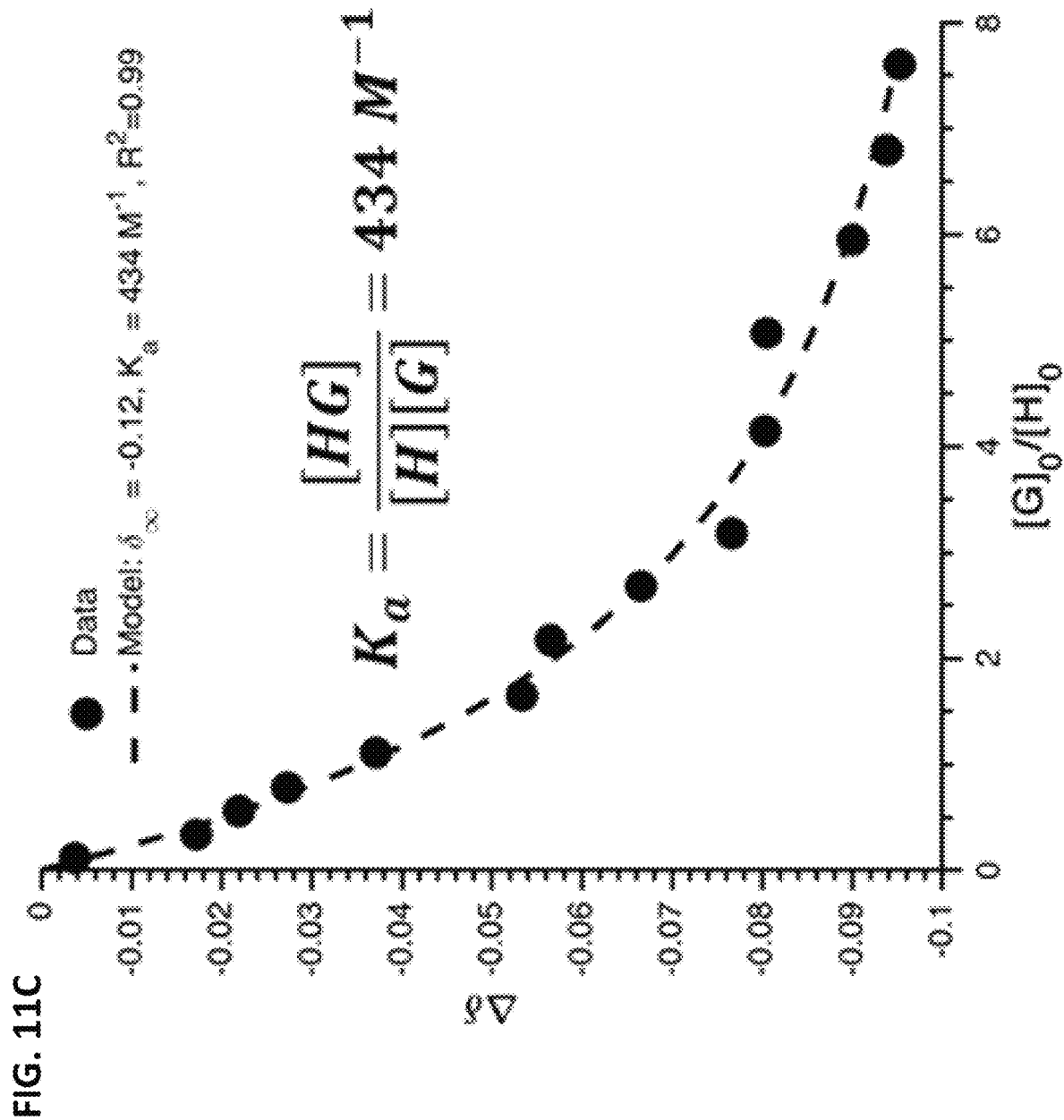
Figure 12A:
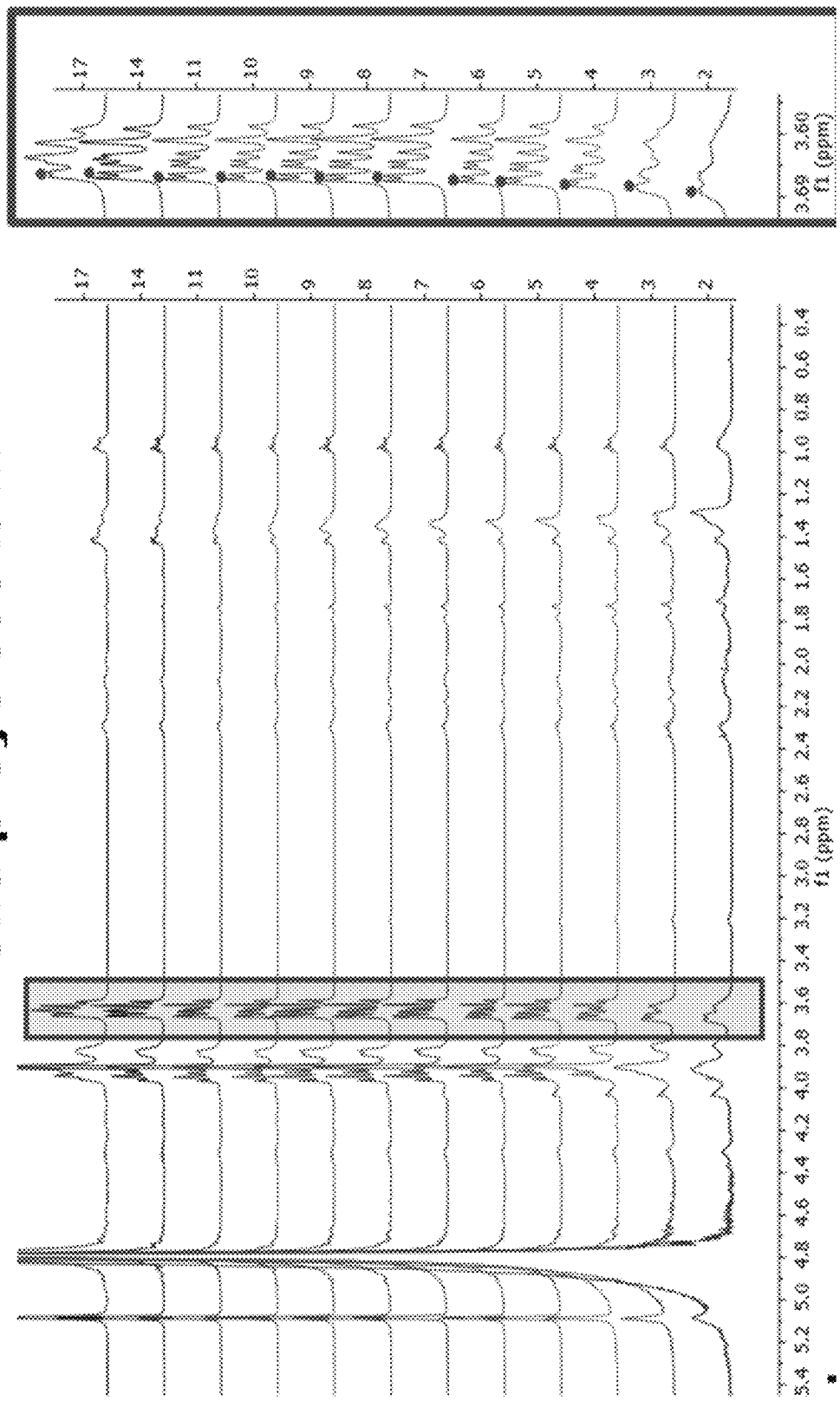
FIG. 12A-C. Determination of Ada-$E_2$ PA and β-cyclodextrin binding constant.
Figure 12B:
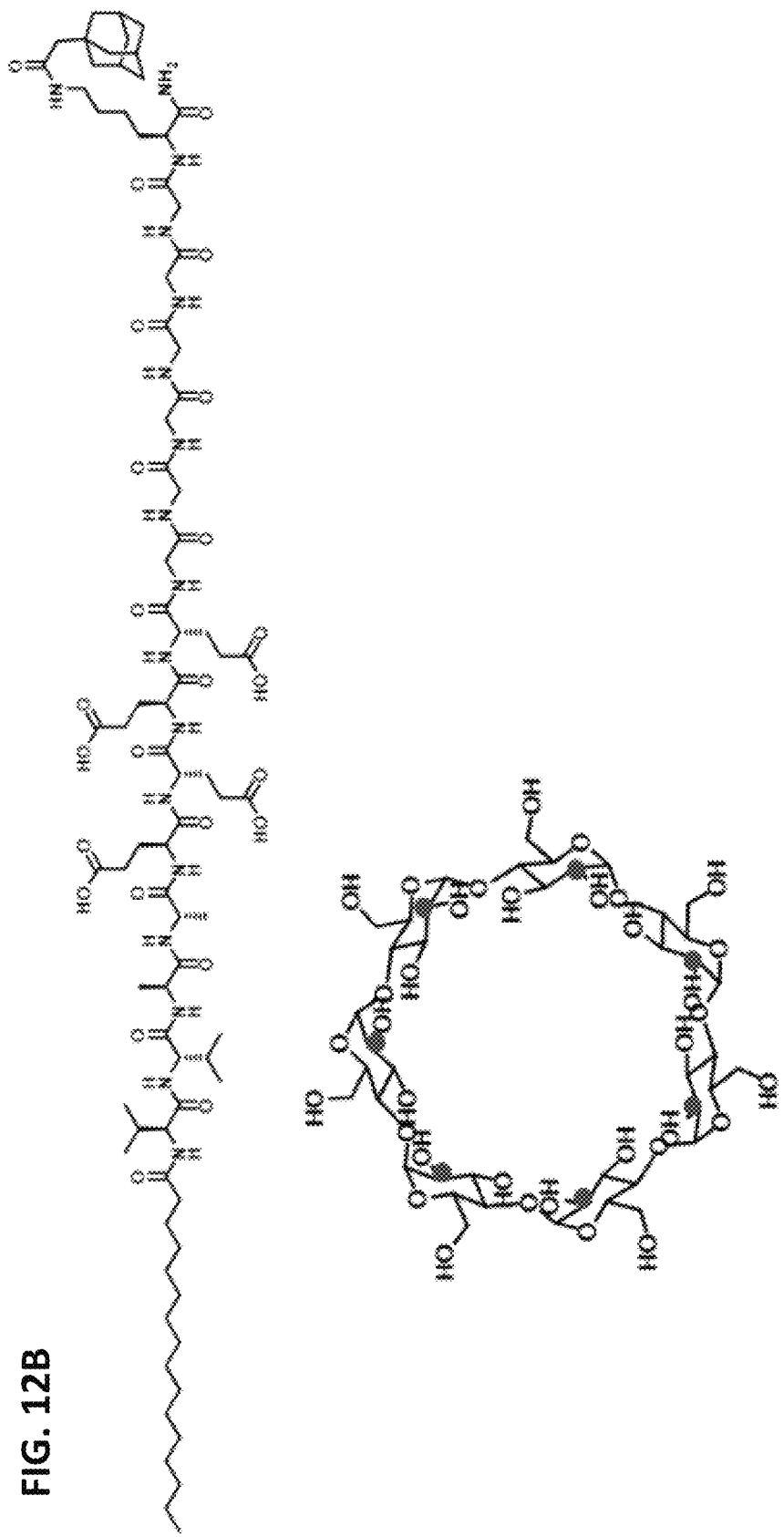
Figure 12C:
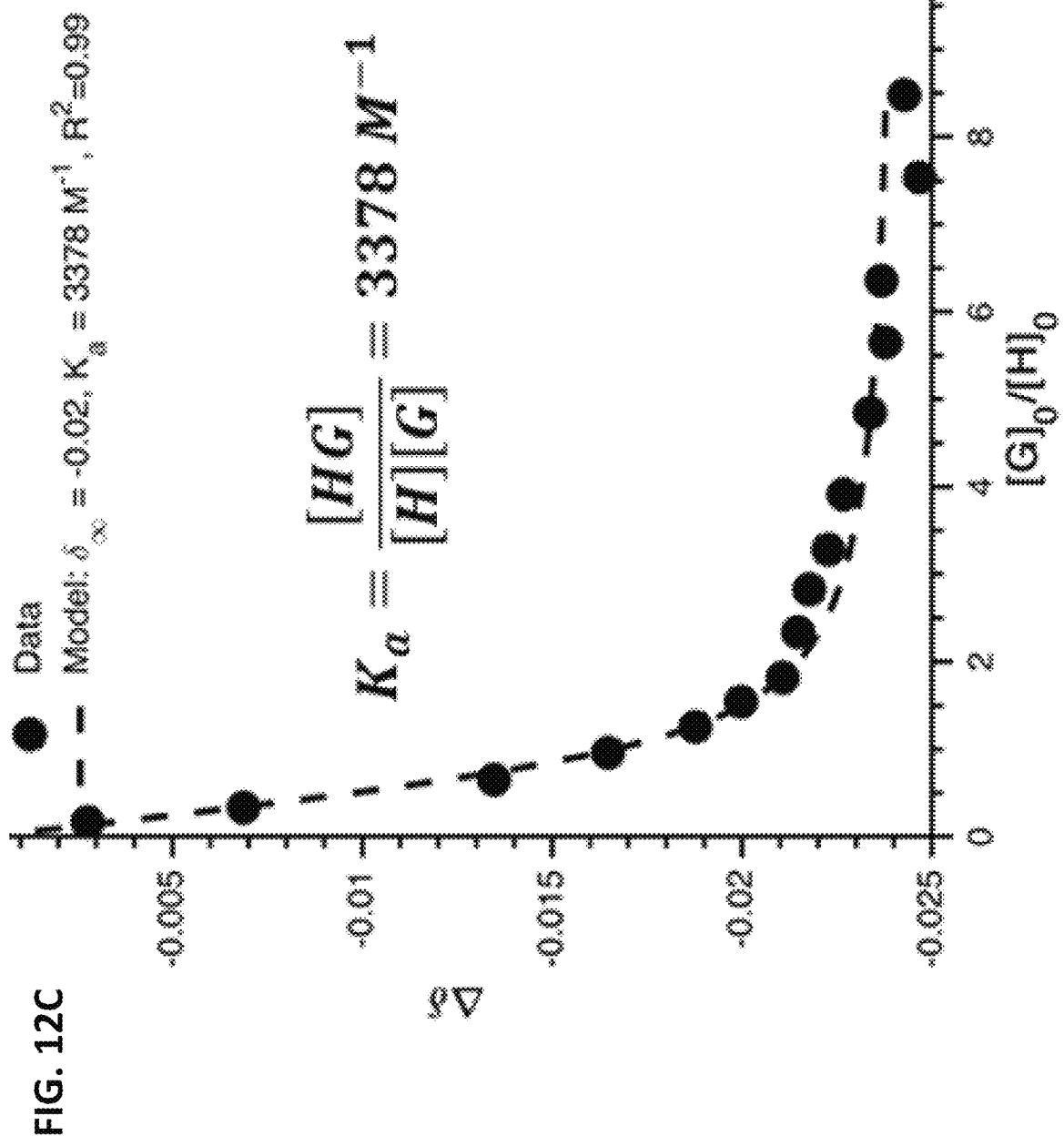
Figure 13A:
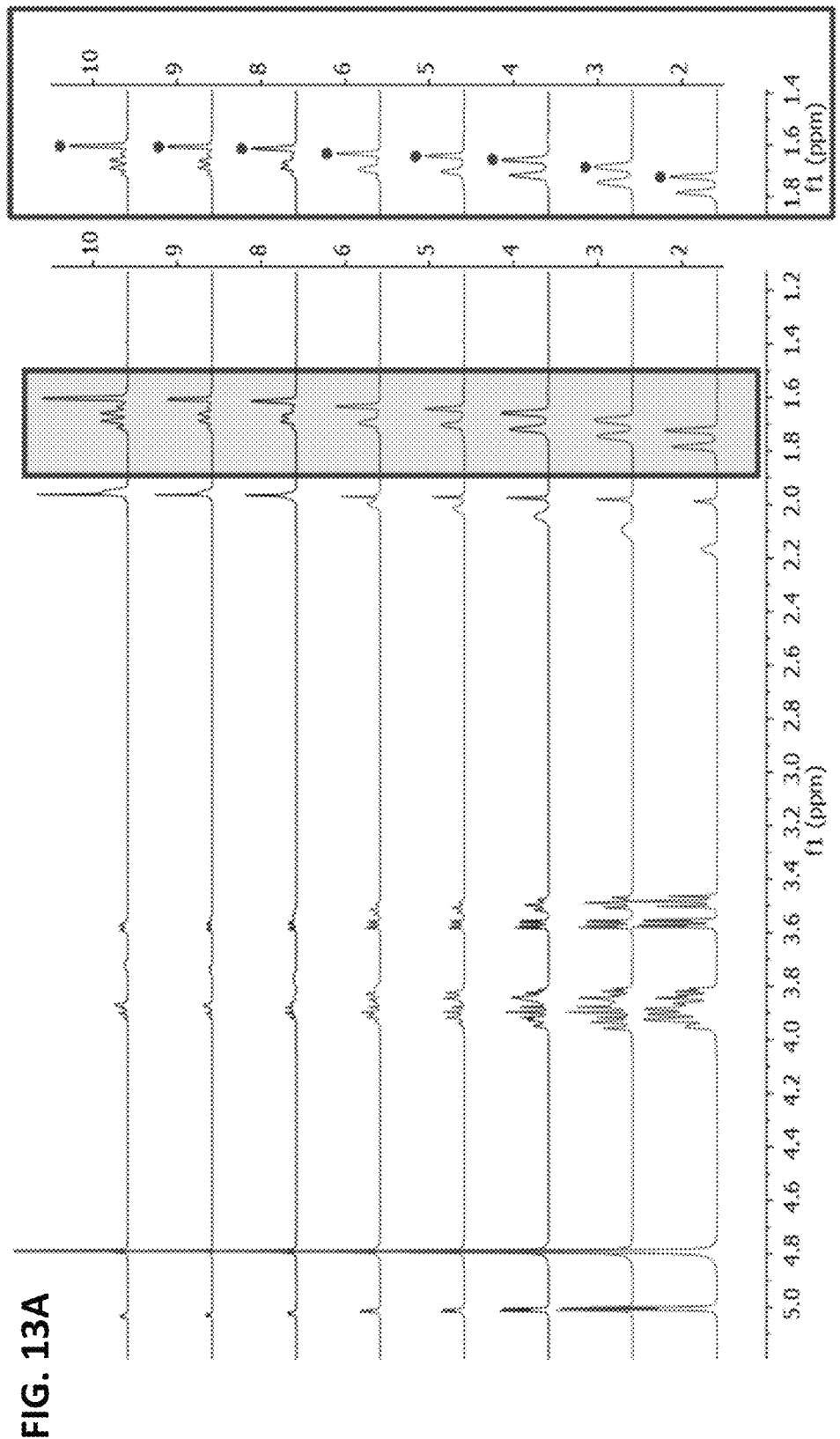
FIG. 13A-C. Determination of β-cyclodextrin and 1-adamantaneacetic acid binding constant.
Figure 13B:
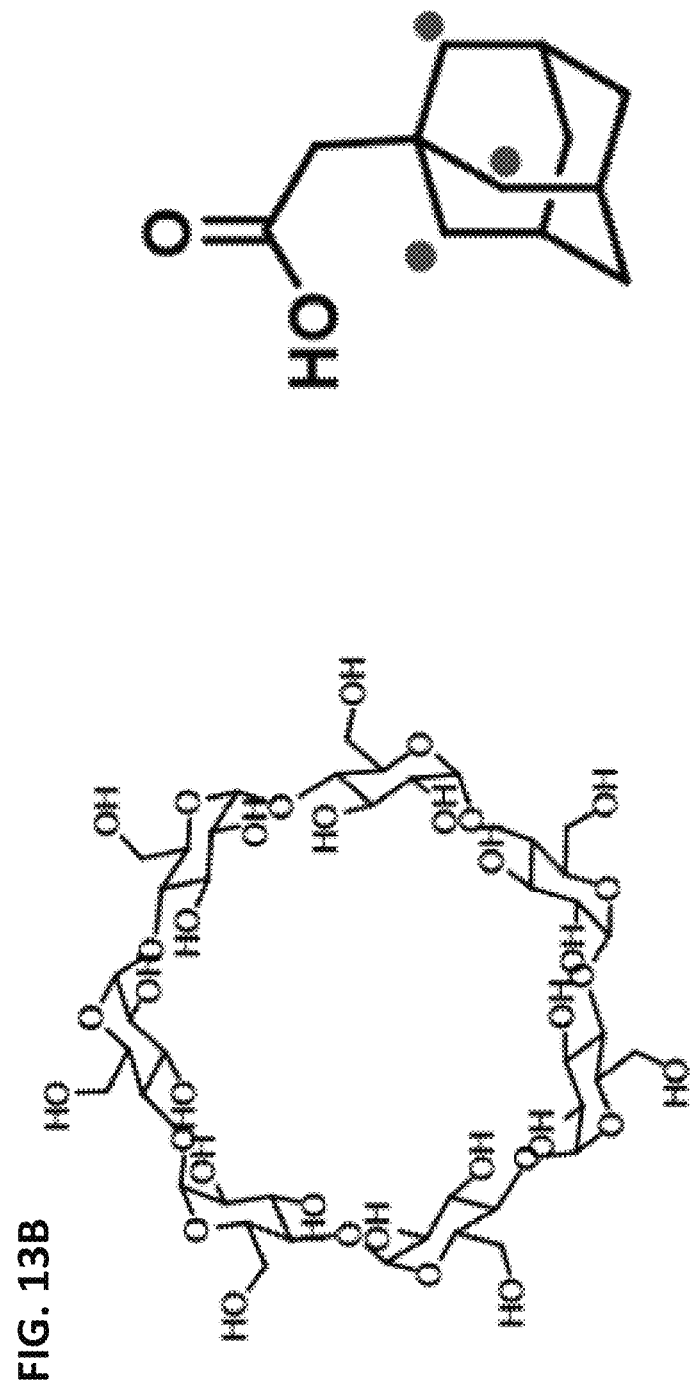
Figure 13C:
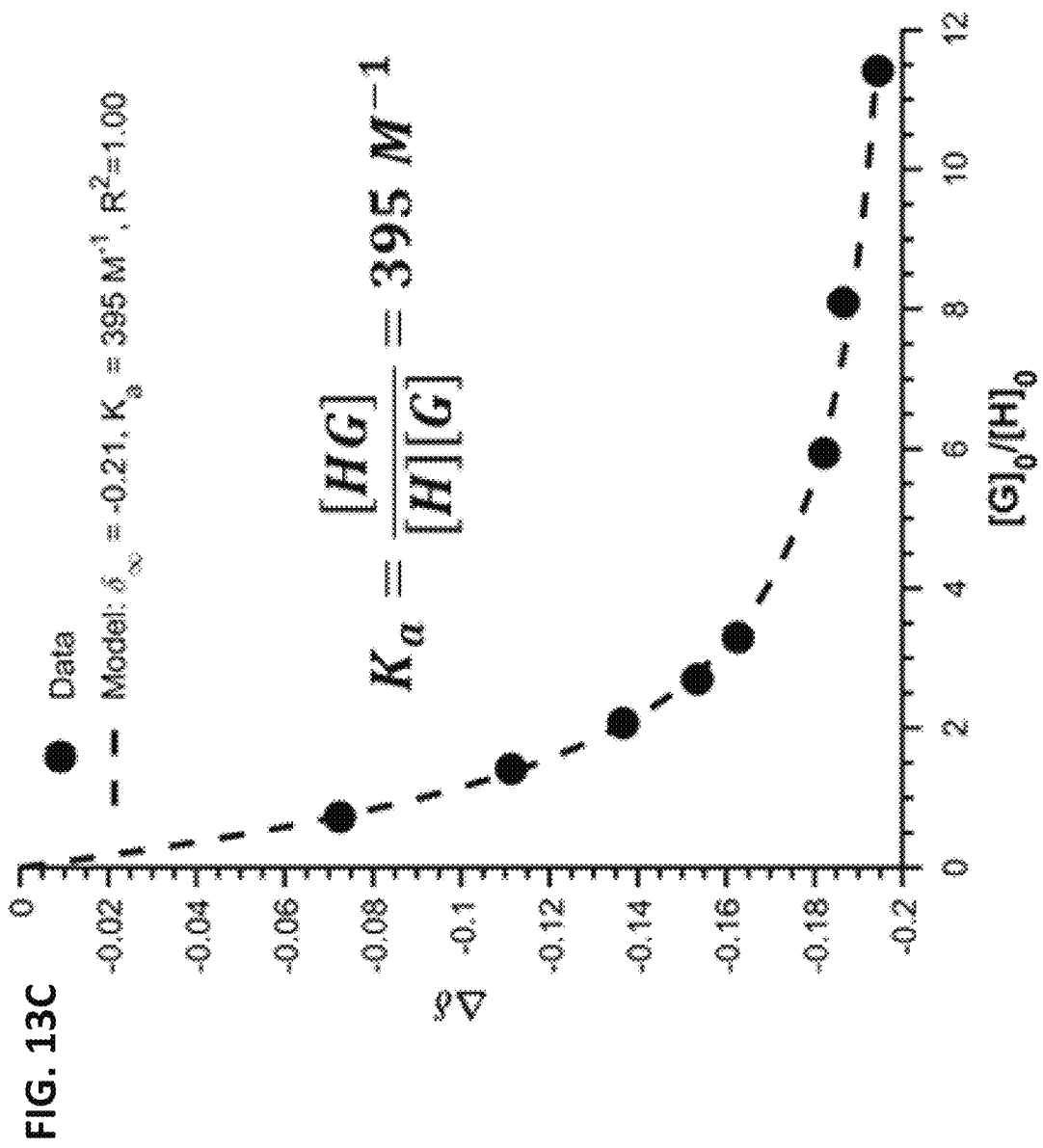

Characterization of Host-Guest Modified Peptide Amphiphile Superstructure Formation To assess the extent of host-guest interactions, proton nuclear magnetic resonance (1H-NMR) spectra were obtained to determine the binding isotherms of the CD-$E_2$ PA and Ada-$E_2$ PA (FIG. 11-13). Since hydrogel formation results in extensive broadening of NMR signals, CD-$E_2$ PA was titrated with soluble 1-adamantaneacetic acid and Ada-$E_2$ PA was titrated with β-cyclodextrin. The binding isotherms showed that both the CD-$E_2$ PA and Ada-$E_2$ PA follow the stoichiometry of a 1:1 host-guest system with association constants ($K_a$) of 434 M$^{-1}$ and 3378 M$^{-1}$, respectively. The difference in association constants between the CD-$E_2$ PA and Ada-$E_2$ PA is likely due to the changes in spacer length and conformational flexibility, where for example, the PA tethered adamantane is likely to be more hydrophobic coupled through an amide bond to a hydrophobic glycine spacer relative to the 1-admantaneacetic acid used with the CD-$E_2$ PA. Additionally, 1:1 stoichiometry of the binding was observed, which facilitates inter-fiber crosslinking.

Figure 2A:
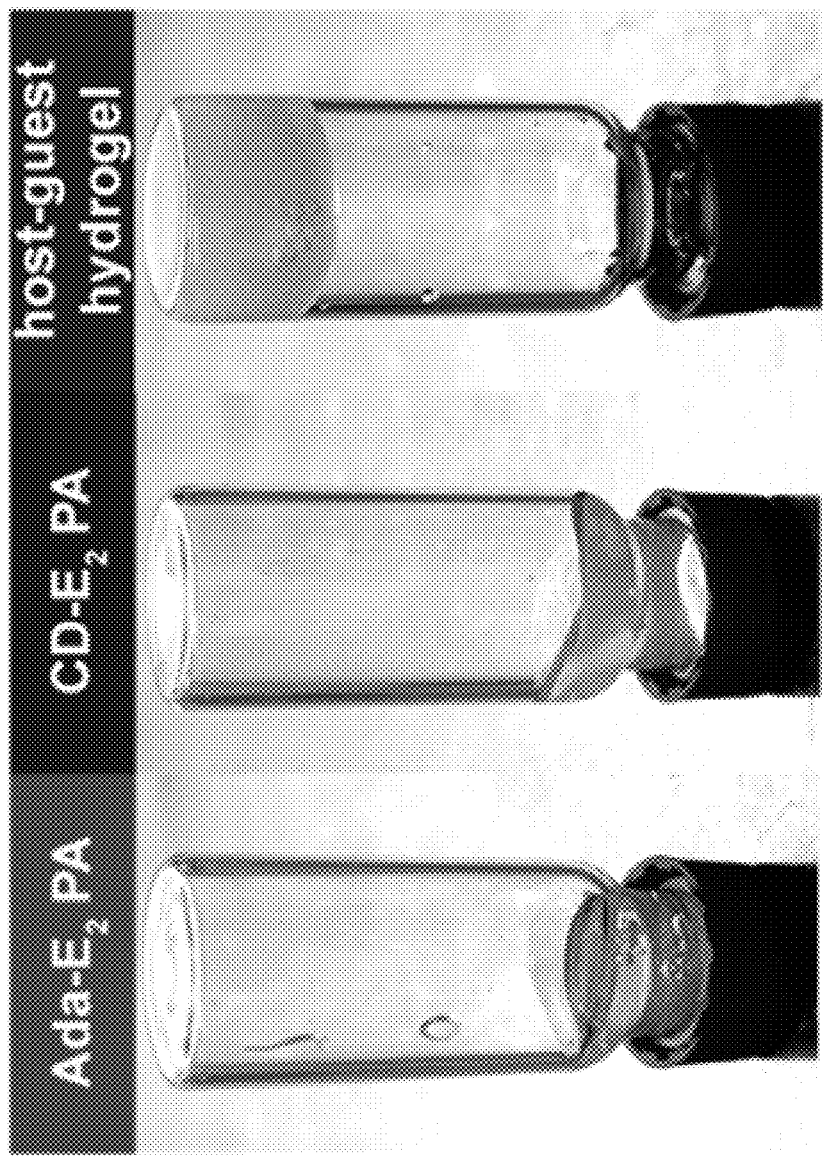
Figure 14A:
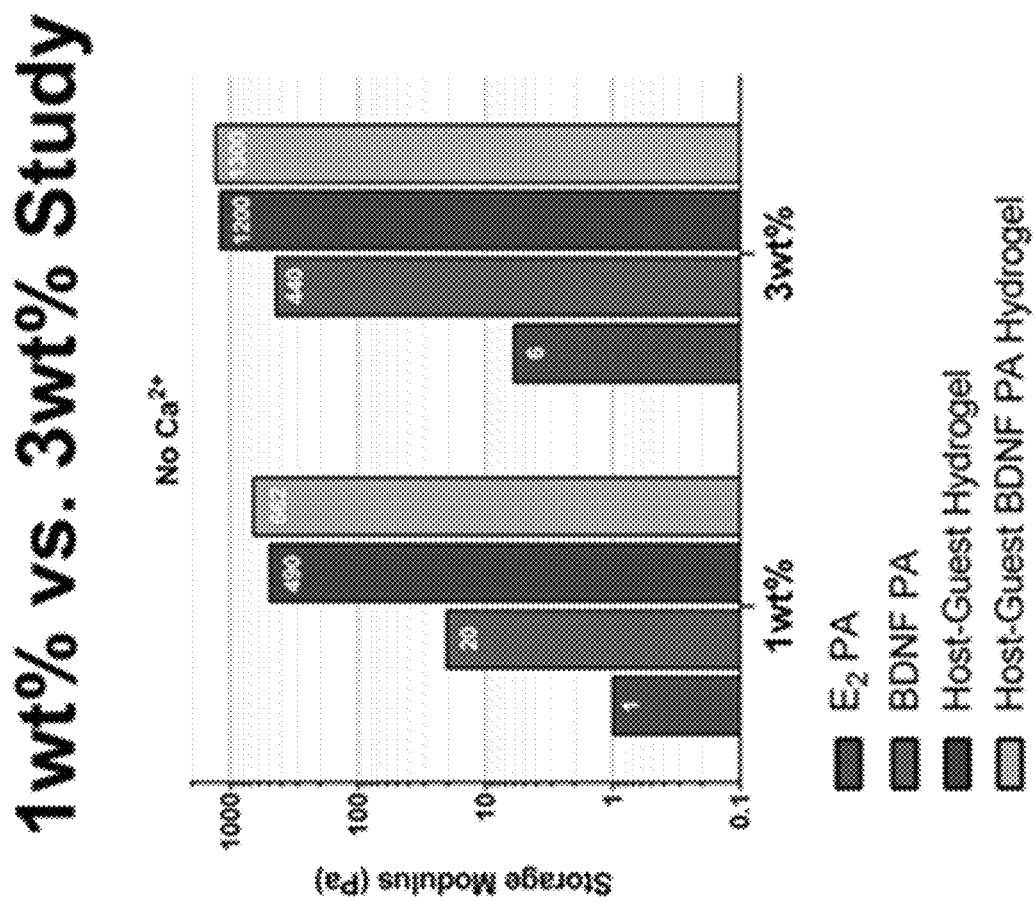
FIG. 14A-B. Comparisons of storage moduli for different hydrogel conditions (FIG. 14A) Comparison of storage moduli for 1 wt % versus 3 wt % hydrogels.
Figure 14B:
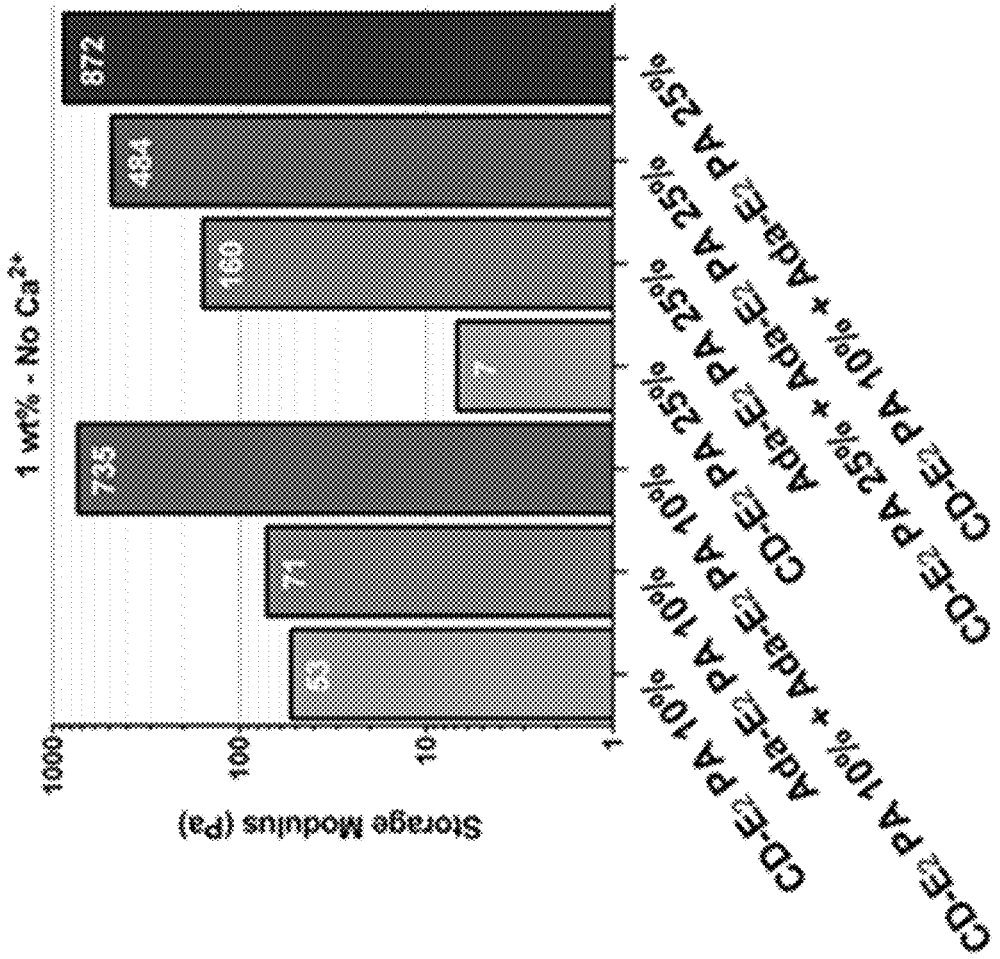
Figure 15:
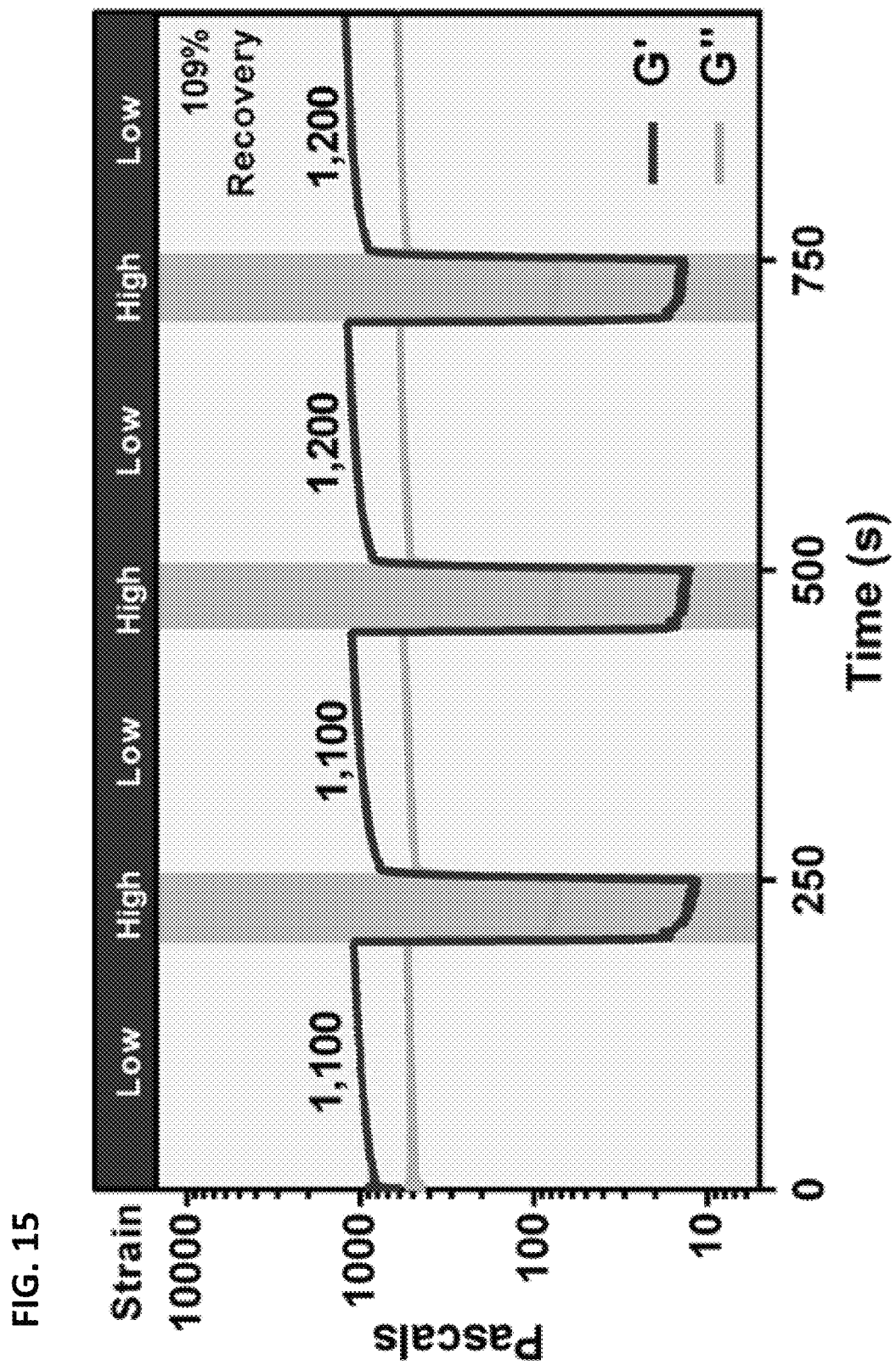
FIG. 15. Rheological Recovery Test of the superstructured mixture. Storage (G') and loss modulus (G") of the superstructured mixture as it was exposed to high and low shear intervals over time. With G' of 1,100 Pa before high strain and 1,200 Pa after 3 intervals of 50% strain with a 109% recovery.

When the CD-$E_2$ PA and Ada-$E_2$ PA were mixed, formation of a soft gel occurred within a minute of pipetting as a result of host-guest crosslinking among PA nanoribbons. While individual PAs formed clear solutions, a stable and opaque self-supporting gel, the host-guest hydrogel, was formed upon mixing (FIG. 2a). Scanning electron microscopy (SEM) was used to study the morphology of the material formed and its individual components (FIG. 2b) (all samples were gelled with divalent cations prior to the required processing for SEM imaging). The CD-$E_2$ PA and Ada-$E_2$ PA samples contained similar homogenous supramolecular polymer structures whereas the host-guest hydrogel revealed large bundles (approximately 1 μm in size) of the nanostructures across the surface of the gel. Differences were also observed in the bulk rheological properties of these systems. Storage (G') and loss (G") moduli were measured for the individual components and the host-guest hydrogel (see FIG. 2c). Gels of $E_2$ PA, Ada-$E_2$ PA, and CD-$E_2$ PA had storage moduli of 20±12 pascals (Pa), 75±17 Pa, and 130±81 Pa, respectively. However, the storage modulus was observed to dramatically increase to 1200±34 Pa when the Ada-$E_2$ PA and CD-$E_2$ PA were mixed 1:1 by volume. When a higher concentration of Ada-PA (25 mol % Ada-PA) relative to the CD-PA (10 mol % CD-PA) was investigated, an increase in storage modulus was observed relative to the 1:1 stoichiometric ratio (FIG. 14). To test the host-guest hydrogel's recovery properties, a high strain was applied to fracture the gel which caused G' to drop below the value measured for G" (FIG. 15). When the high strain was removed, the mixed material returned to its original values of G' and G". This reversible change in rheological properties may indicate that the material possesses self-healing capabilities mediated by the reversible host-guest interactions among the supramolecular polymers. Based on the observation of large bundles of nanoscale ribbons in the host-guest hydrogel, it was hypothesized that an intense dynamic event has occurred in the system upon mixing.[8, 11] This interesting phenomenon involves the spatial relocation across long distances (possibly microns) of monomers (or monomer clusters) containing either host or guest moieties in order to concentrate and optimize the number of the highly favorable host-guest contacts. The observed large bundles of supramolecular polymers are referred to herein as a "superstructure" whose formation is hypothesized to occur through this dynamic mechanism.

Figure 16B:
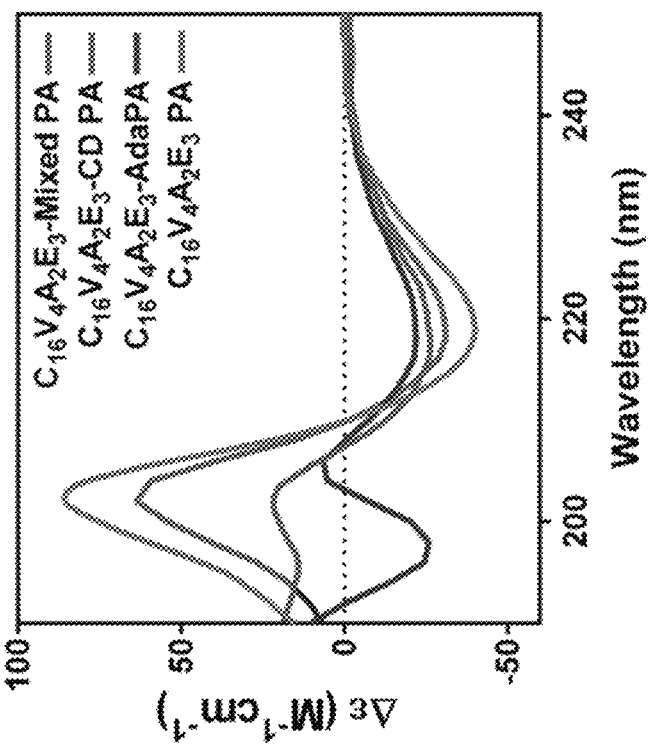
FIG. 16A-B. Fiber analysis of $V_4$-modified host-guest PAs.
Figure 16A:
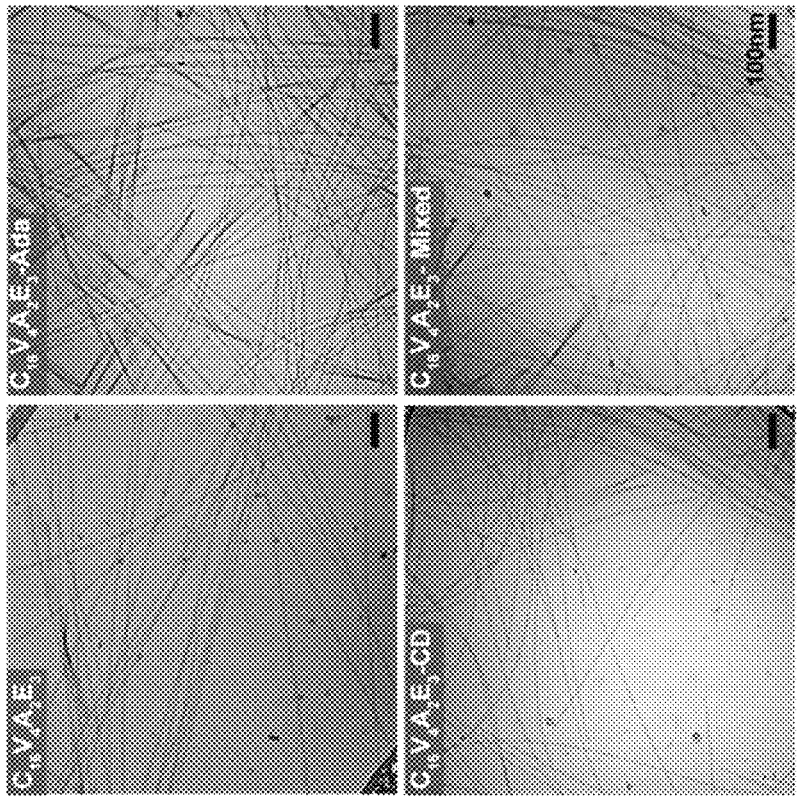
Figure 17B:
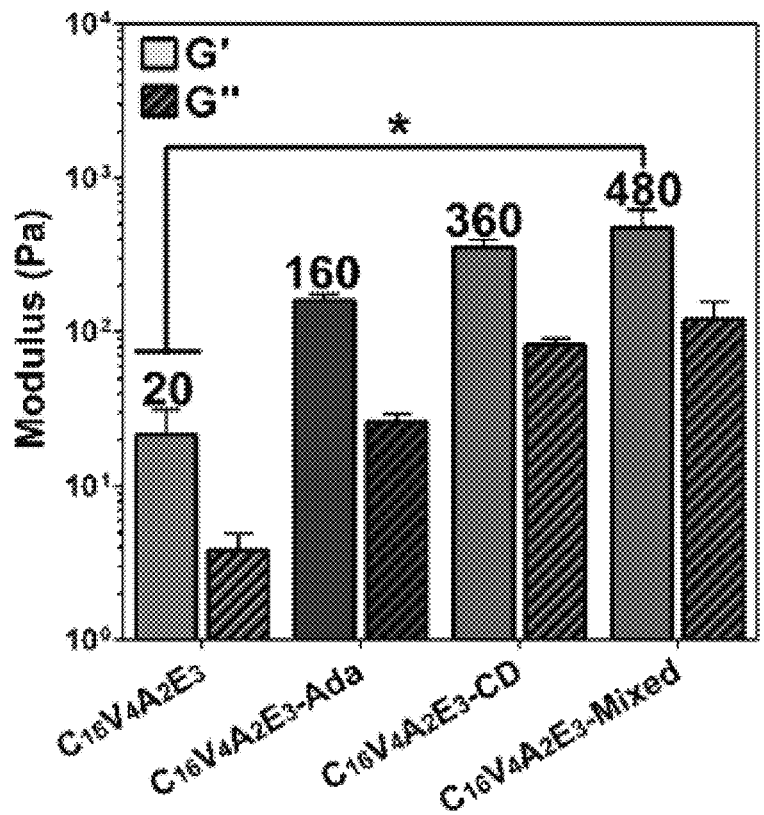
Figure 17C:
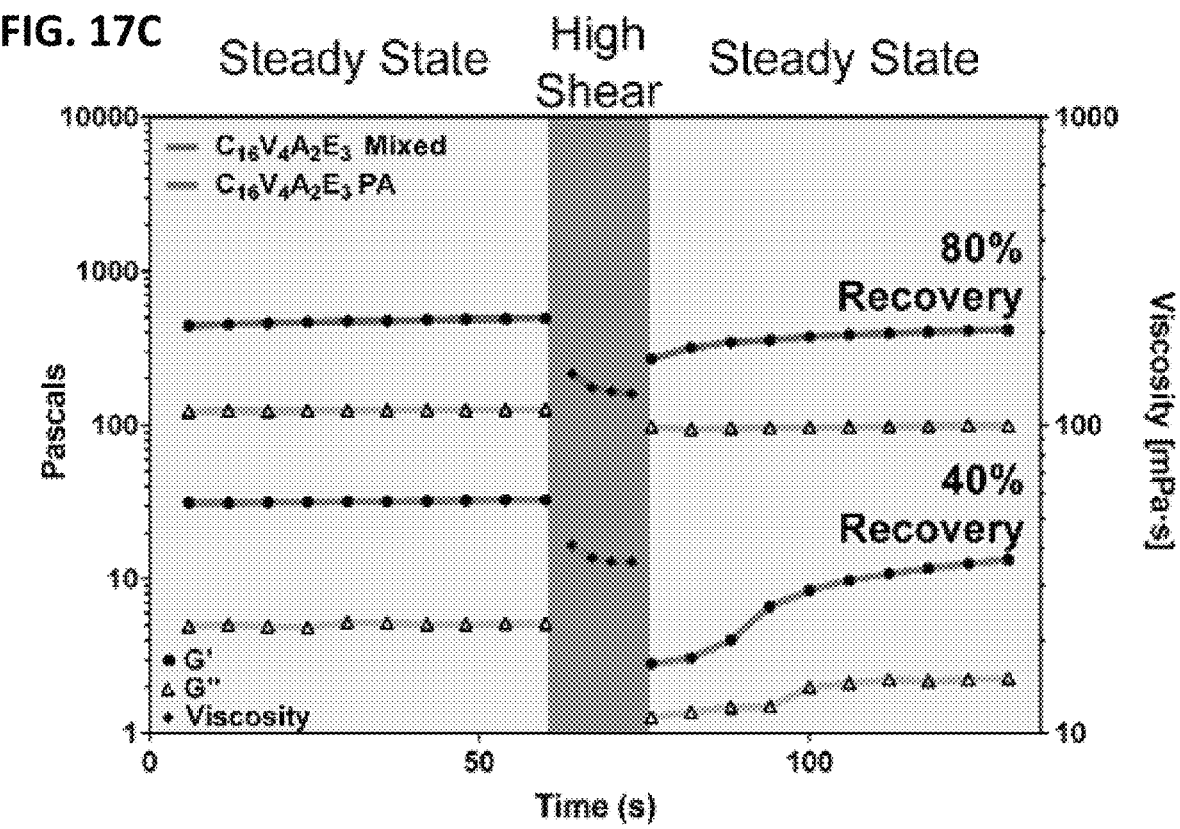

To test the hypothesis that exchange dynamics in these supramolecular systems contributed superstructure formation, additional host-guest modified peptide amphiphiles with stronger intermolecular cohesion were synthesized. These additional PAs contained two additional valine residues, which may increase the strength of the β-sheet.[42] One glutamic acid residue was also removed to lower the assembly's charge density which then increases further the cohesive energy of the supramolecular polymers. The objective of these modifications in the structure of PAs was to reduce the propensity for molecular exchange. These new molecules formed nanoribbons as observed by cryo-TEM and all contain evidence of internal β-sheet character as observed by CD (FIG. 16). Interestingly, significant hierarchical superstructure formation was not observed within the mixture of these control molecules as demonstrated by SEM micrographs (FIG. 17a). Bundle formation was significantly reduced with only small bundled structures of approximately 150 nm in width observed as opposed to approximately 1 μm in the supramolecular polymers where dynamic exchange was observed. Moreover, the storage modulus of these mixtures was not enhanced relative to that of individual cyclodextrin and adamantane peptide amphiphile supramolecular polymers indicating that the stronger β-sheet and reduced charge indeed inhibit molecular exchange (see FIG. 17b-c).

Figure 2C:
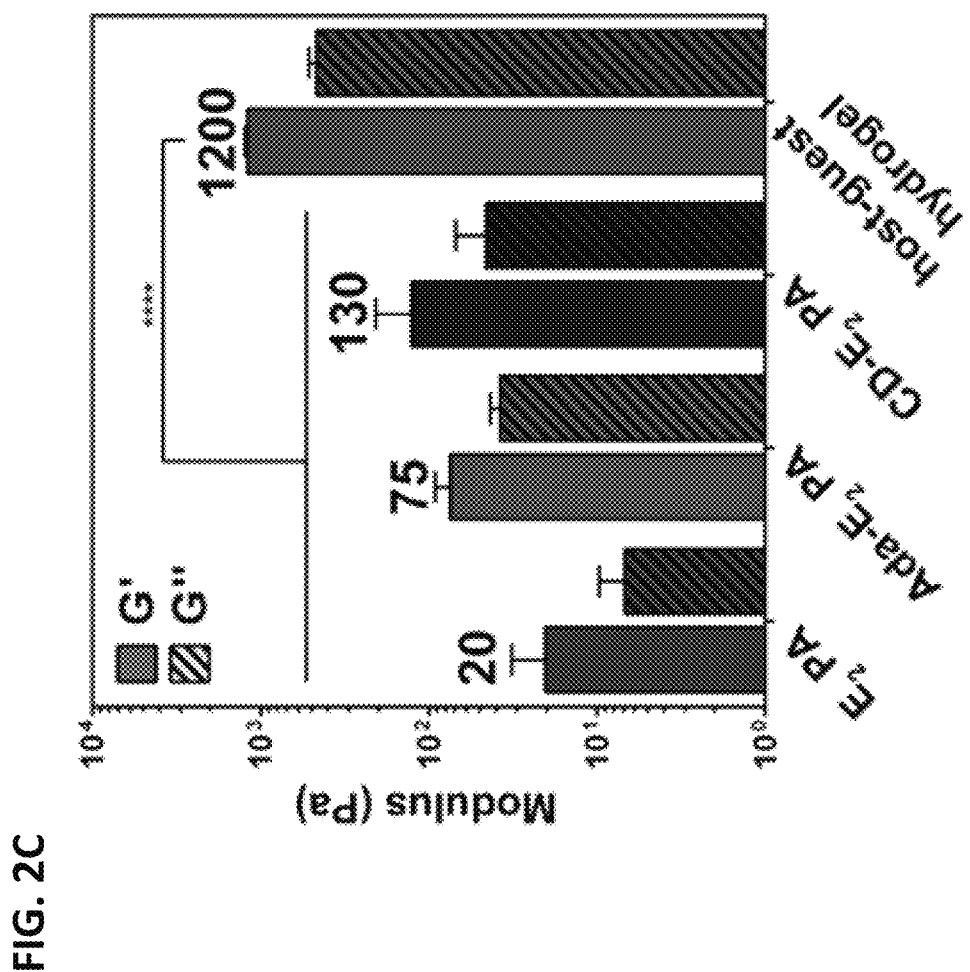
Figure 2H:
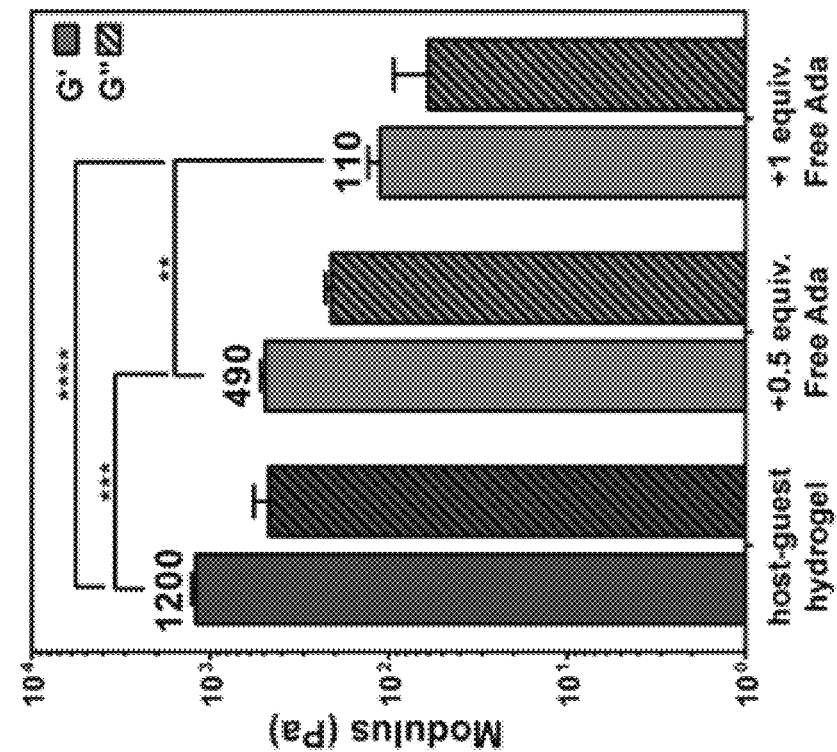
Figure 2G:
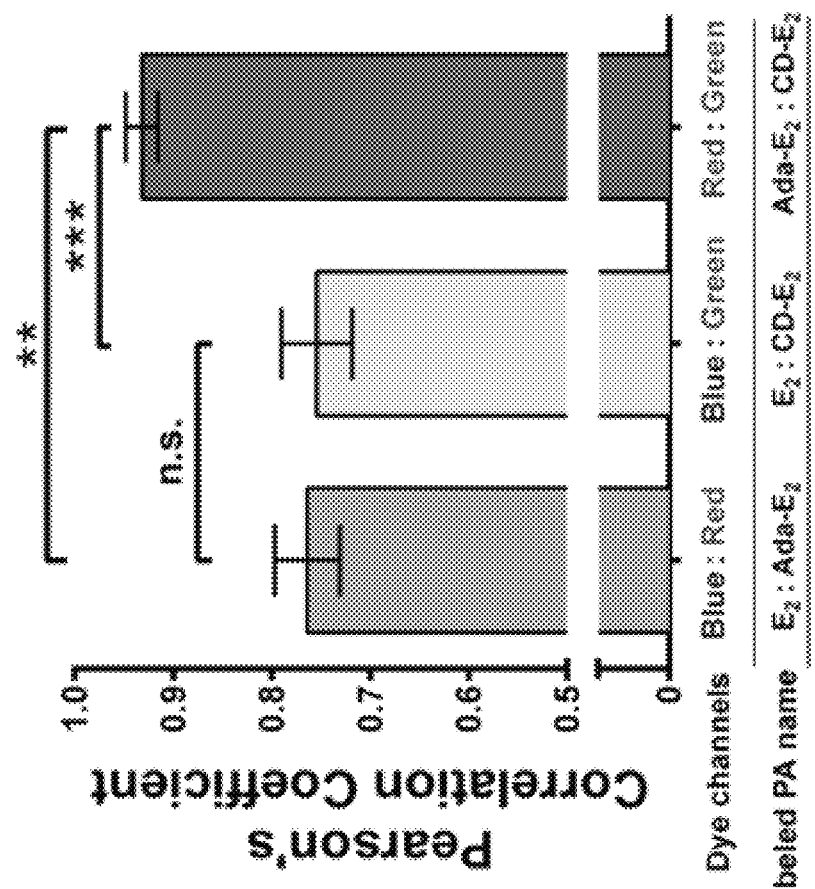
Figure 18A:
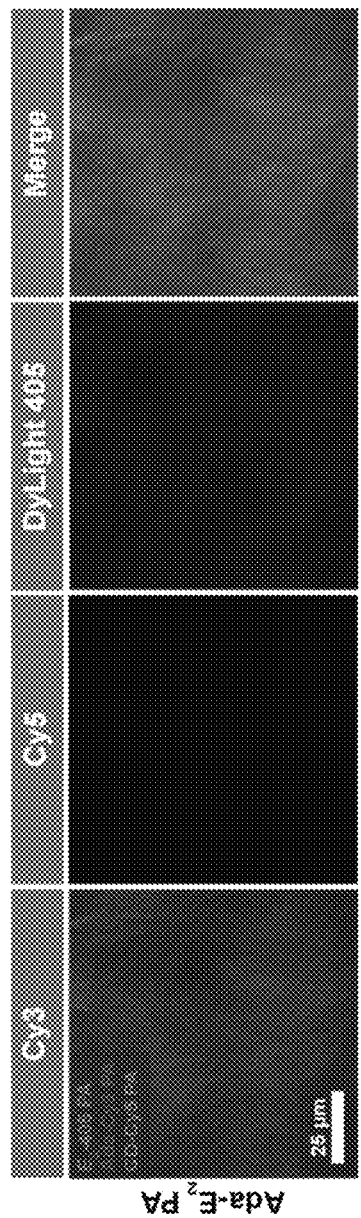
FIG. 18A-C. Split channels of the Ada-$E_2$ PA, CD-$E_2$ PA and superstructured mixture. Confocal Micrograph z-stacks split into individual channels (Left to right): Cy3 functionalized adamantane PA (Red), Cy5 functionalized cyclodextrin PA (Green), and DyLight 405 functionalized $E_2$ PA (Blue) of the (FIG. 18A) Ada-$E_2$ PA, (FIG. 18B) CD-$E_2$ PA, and (FIG. 18C) the superstructured host-guest hydrogel.
Figure 18B:
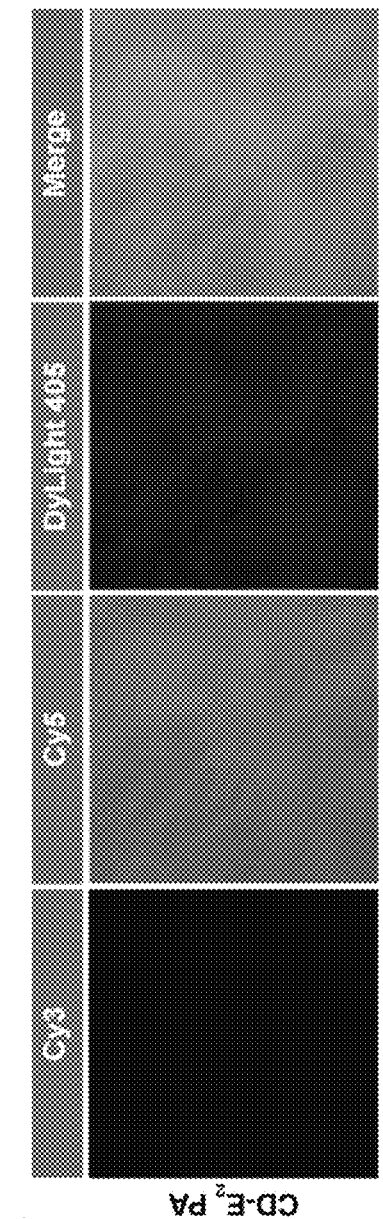
Figure 18C:
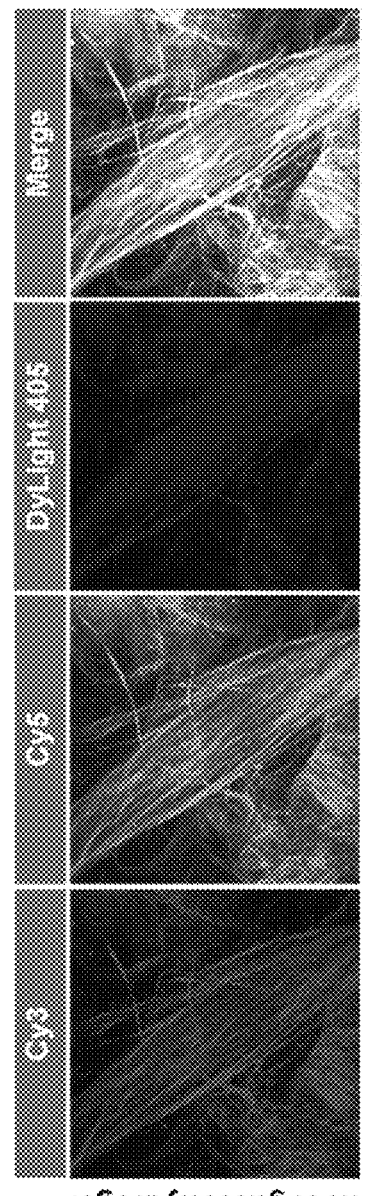

To study the superstructured material bundling phenomena further, confocal microscopy was used to allow for probing of the internal structure of the gels formed. To enable visualization, the PAs were modified with fluorophores, the $E_2$ PA was modified with DyLight 405 (Blue) while the Ada PA and CD PA were modified with cyanine 3 (Cy3, Red) and cyanine 5 (Cy5, Green), respectively. Samples of the CD-$E_2$ PA and Ada-$E_2$ PA with the fluorophores were both liquid in nature and their micrographs revealed isotropic solutions with small aggregates of fibers (FIG. 2d-f and FIG. 18a-b). When the two samples were mixed, the resulting superstructured host-guest hydrogel exhibited 10-100 μm bundles throughout the gel's structure, similar to those observed by SEM, suggesting the addition of fluorophores did not significantly impact superstructure formation (FIG. 2f and FIG. 18c). The emergence of the large bundles resulted in enhanced porosity throughout the depth of the gels imaged. The white and yellow color suggested the colocalization and possible reorganization of the Cy3-labeled Ada-$E_2$ PA and Cy5-labeled CD-$E_2$ PA within the superstructure bundles. Dylight 405-labeled $E_2$ PA was observed throughout the whole image indicating that the host-guest PAs are primarily responsible for the formation of the bundles. To further understand this self-assembly driven bundling phenomenon, micrographs of the superstructured assembly were assessed for colocalization between the different dye-labeled PAs utilizing the Pearson's correlation coefficient, which quantitatively compares pixel colocalization.[47] Briefly, the Pearson's correlation coefficient measures the pixel-by-pixel covariance in the signal levels of two images; a perfect positive correlation is 1, no observed correlation is 0, and a perfectly inverse correlation is −1[48] By comparing the Pearson's correlation coefficients of the DyLight 405-labeled $E_2$ PA, Cy3-labeled Ada-$E_2$ PA, and the Cy5-labeled CD-$E_2$ PA in images of the superstructured material, an enhanced Pearson's correlation coefficient was evident for the Ada-$E_2$ PA with the CD-$E_2$ PA when compared to either of these with the $E_2$ PA (FIG. 2g). It is suggested that the increase in colocalization of the Ada-$E_2$ PA and the CD-$E_2$ PA is a result of reorganization via dynamic exchange of these molecules and thus their enrichment within the bundles. The $E_2$ PA does not colocalize as well, implying there are regions of higher density of $E_2$ PA molecules that do not overlap with the cyclodextrin or adamantane PAs and the most likely cause of this would be a redistribution of molecules as proposed above.

Figure 2I:
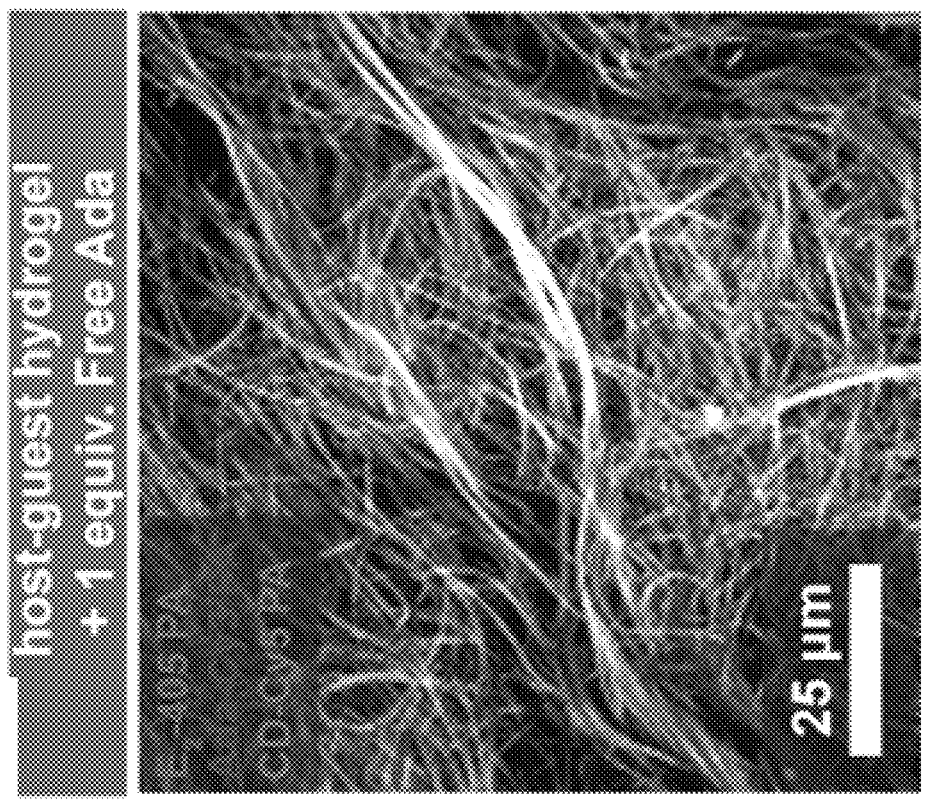
Figure 2J:
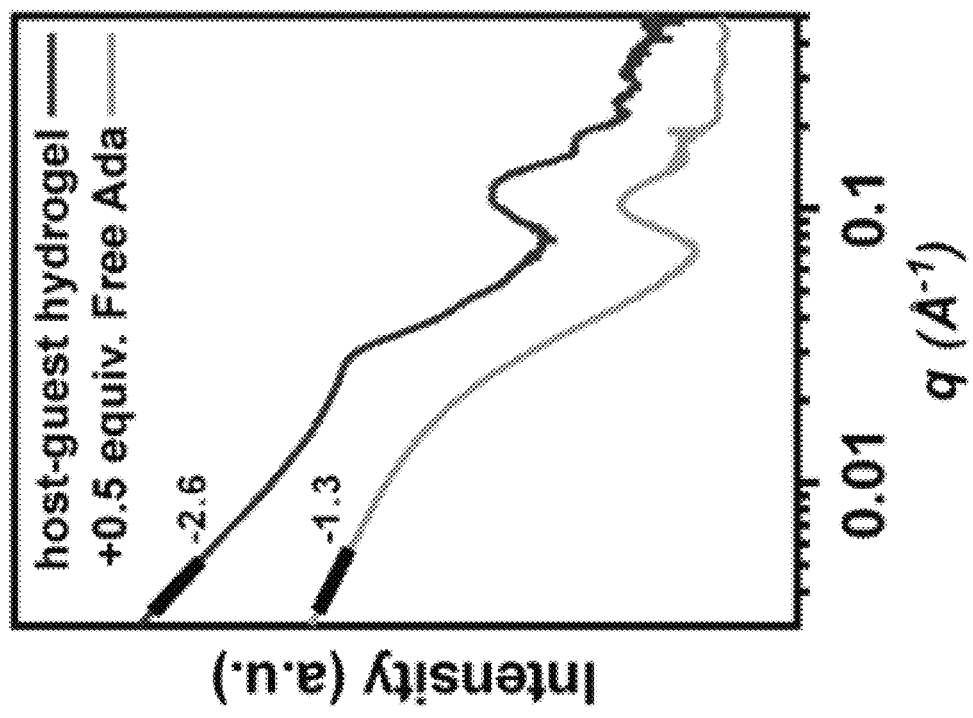
Figure 2K:
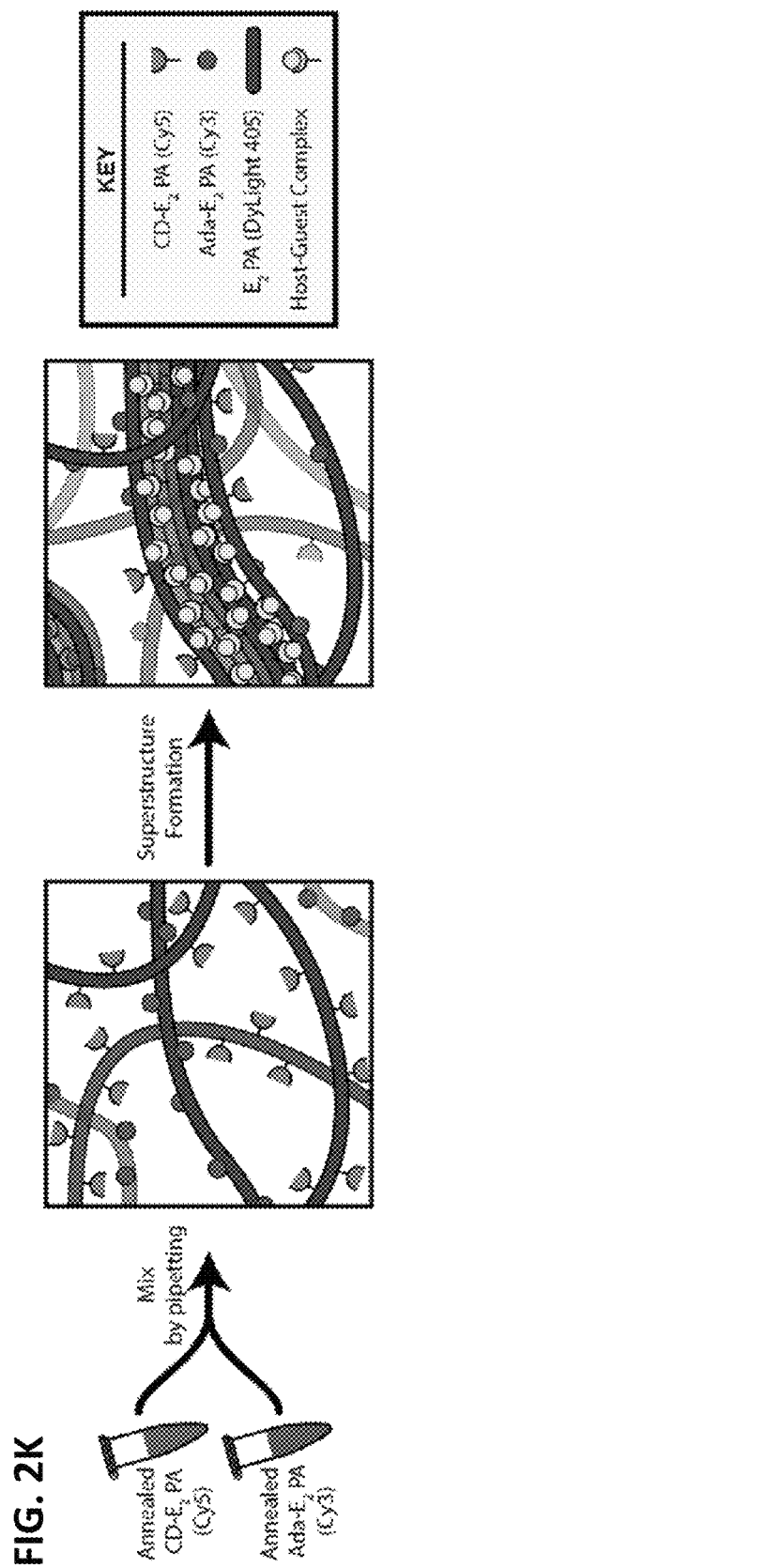
Figure 19A:
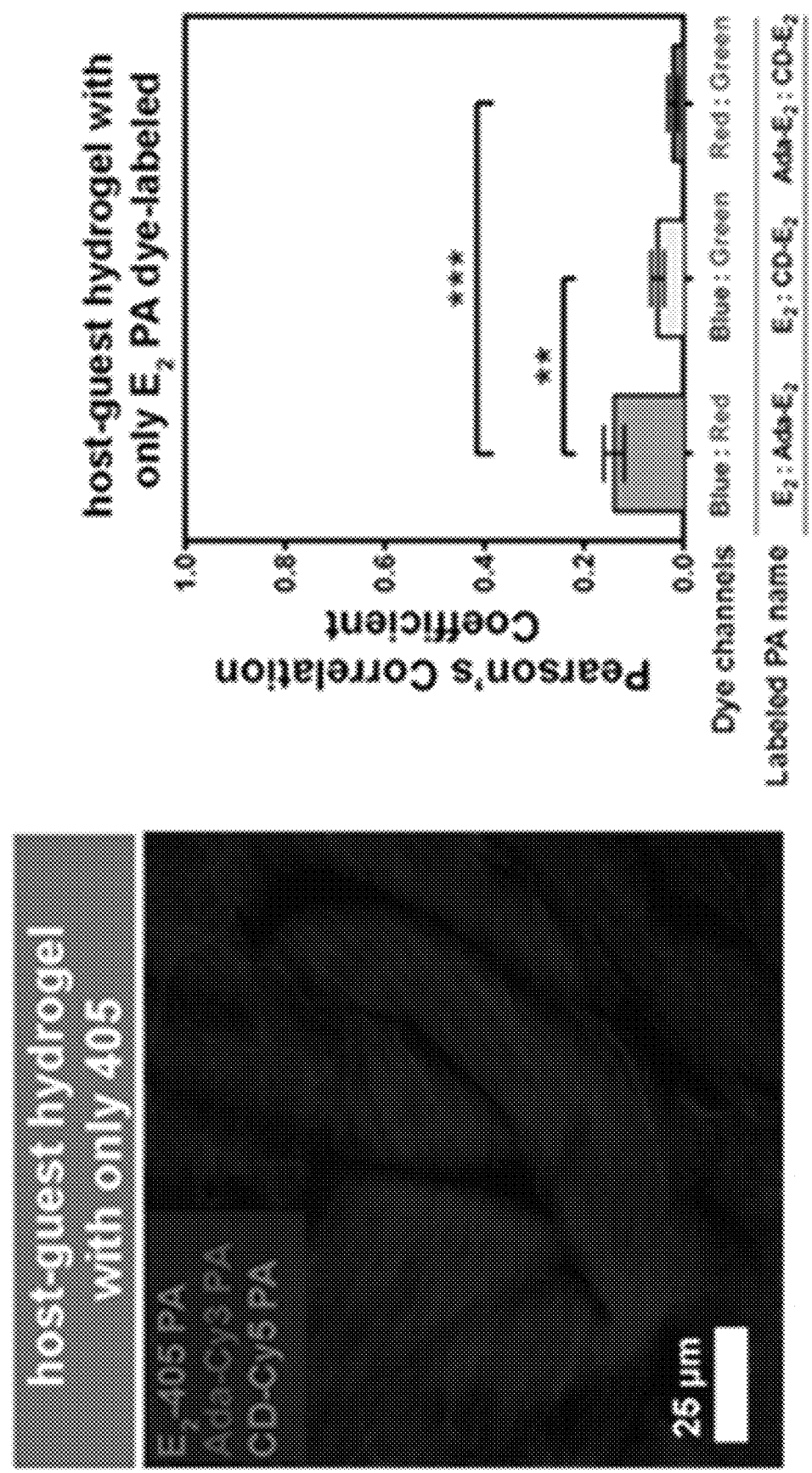
FIG. 19A-C. Pearson's correlation analysis of single fluorescent labelled control samples. Comparison of Pearson's correlation coefficients between fluorescent channels of images with only (FIG. 19A) the $E_2$ PA dye-labeled (405 only), (FIG. 19B) the Ada-$E_2$ PA dye-labeled (Cy3 only) and (FIG. 19C) the CD-$E_2$ PA dye-labeled (Cy5 only). Data displayed as mean±SEM, with significance assessed with a one-way ANOVA followed by a Bonferroni post-hoc test, P<0.01, *P<0.001.
Figure 19B:
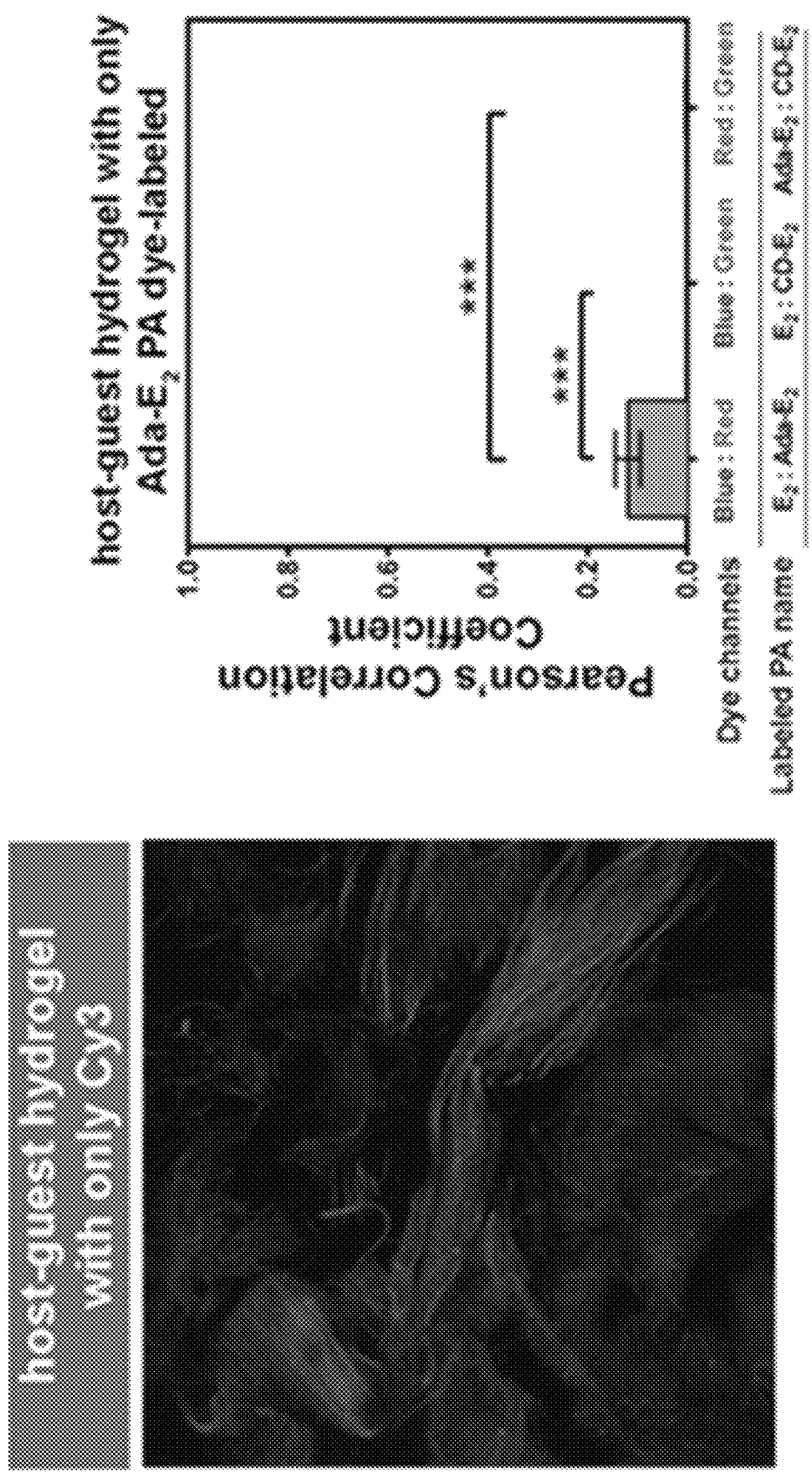
Figure 19C:
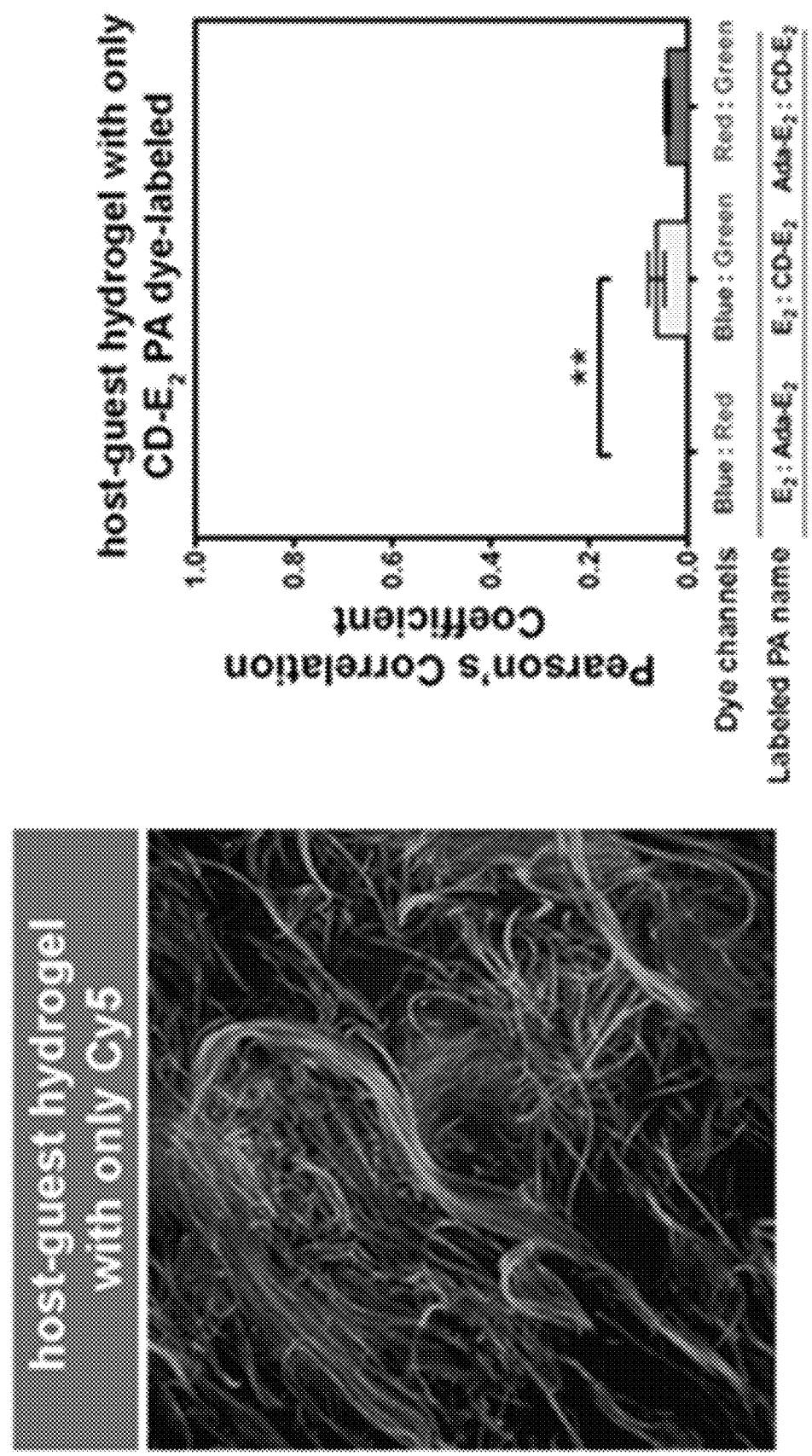
Figure 20:
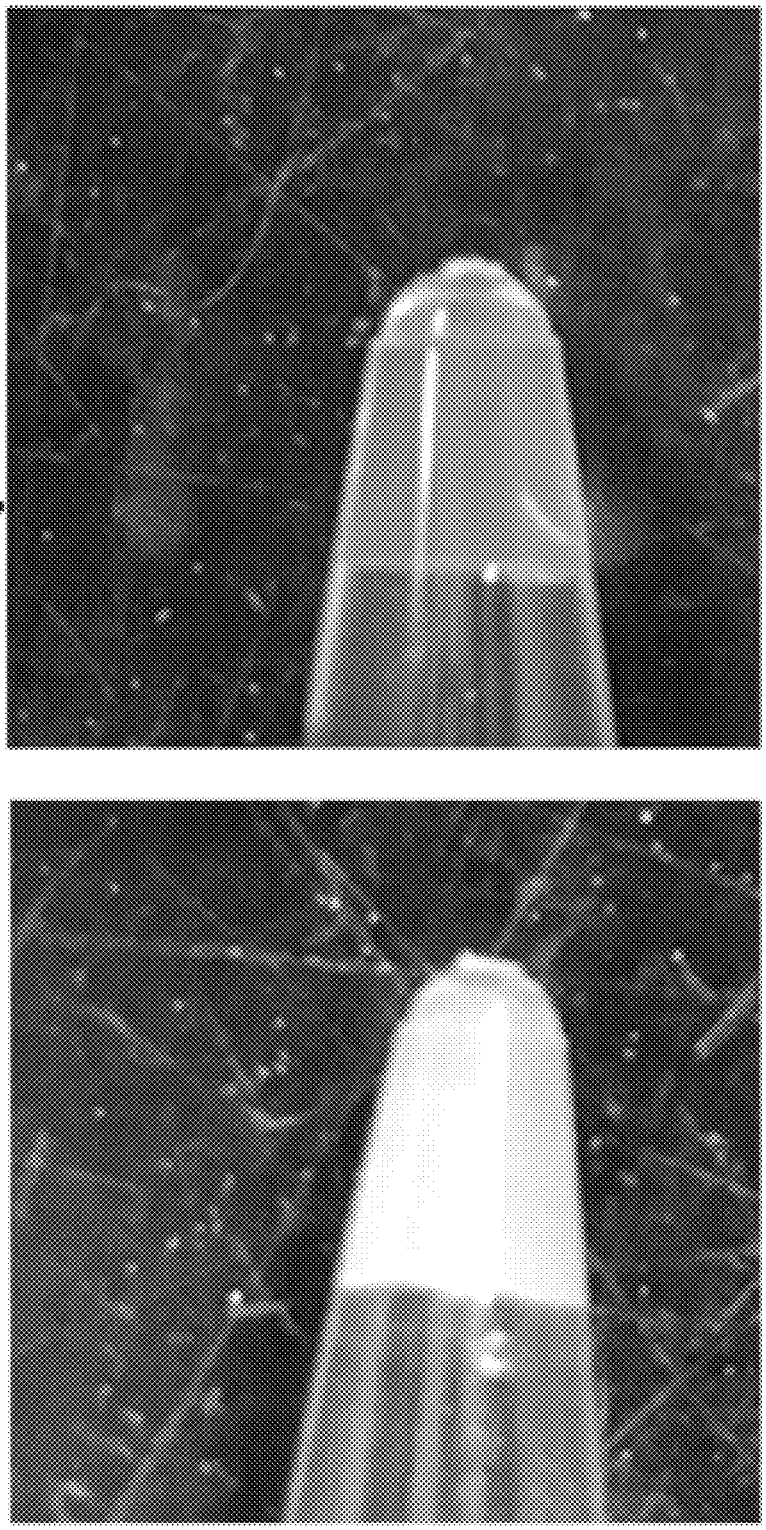
FIG. 20. Photographs of superstructured host-guest hydrogel disassembly with free adamantane. Photographs of the superstructured host-guest hydrogel before (left) and after (right) the addition of 1 equivalent (equiv.) free adamantane (Free Ada).

Control experiments of single, fluorescently labelled, PA samples did not reveal any appreciable colocalization between channels (FIG. 19). Hence, this quantitative analysis of the confocal Z-stacks of the superstructured PA material provides evidence to support superstructure formation as a result of the host-guest interaction between the PA nanoribbons. To test the reversibility of the superstructure formation, a solution of 1-adamantaneacetic acid (free adamantane) was used to outcompete the Ada-$E_2$ PA and dissociate the host-guest interaction with the CD-$E_2$ PA which resulted in a visible decrease in opacity of the sample (FIG. 20). Furthermore, as free adamantane was added to the superstructured host-guest hydrogel, the storage modulus decreased as well. With 0.5 equivalents of free adamantane added relative to the CD-$E_2$ PA, the modulus was 490±22 Pa and with 1 equivalent the modulus decreased further to 110±13 Pa (FIG. 2h). This modulus is similar to that measured for the Ada-$E_2$ PA and the CD-$E_2$ PA prior to mixing (FIG. 2c). SAXS analysis after addition of adamantane (FIG. 2i) demonstrated that the peak at approximately 24.7 nm for the superstructured host-guest hydrogel disappeared entirely and the Guinier slope returned to −1.3, resulting in a scattering distribution more representative of the individual CD-$E_2$ PA and Ada-$E_2$ PA solutions (as shown in FIG. 1h). By confocal microscopy, as 1 equivalent of adamantane was added to the superstructured host-guest hydrogel, bundle formation decreased throughout the gel (see FIG. 2j). After the addition of 2 equivalents of adamantane, large bundles could not be observed and only very small aggregates of filaments of approximately 1 μm in width were observed, suggesting the dissociation of the host-guest interactions and the reversal of the enhanced porosity that was driven by the formation of the superstructures formed within the gel (FIG. 21). In summary, interactions between the Ada-$E_2$ PA and CD-$E_2$ PA and dynamic exchange drove superstructure formation, which in turn created not only morphological changes in the gels but also rheological changes as well. Dynamic exchange among the molecules allowed the formation of supramolecular polymers that concentrate host-guest interactions within the regions containing the bundled fibers of the superstructure (FIG. 2k). Furthermore, the reversibility of this process was demonstrated through the addition of soluble guest molecules to displace inter-fiber crosslinking.

Figure 3A:
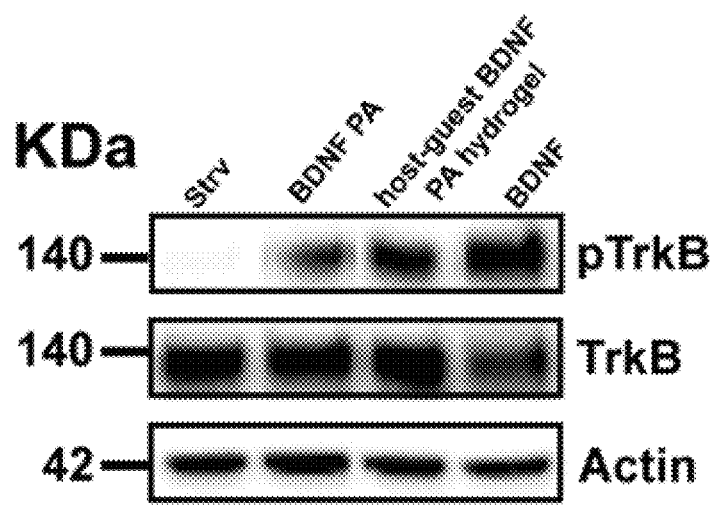
Figure 3B:
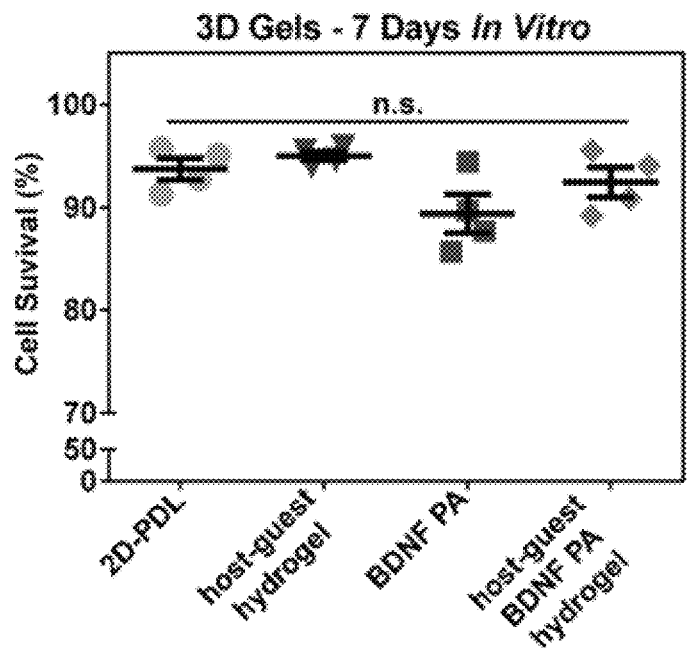
Figure 22D:
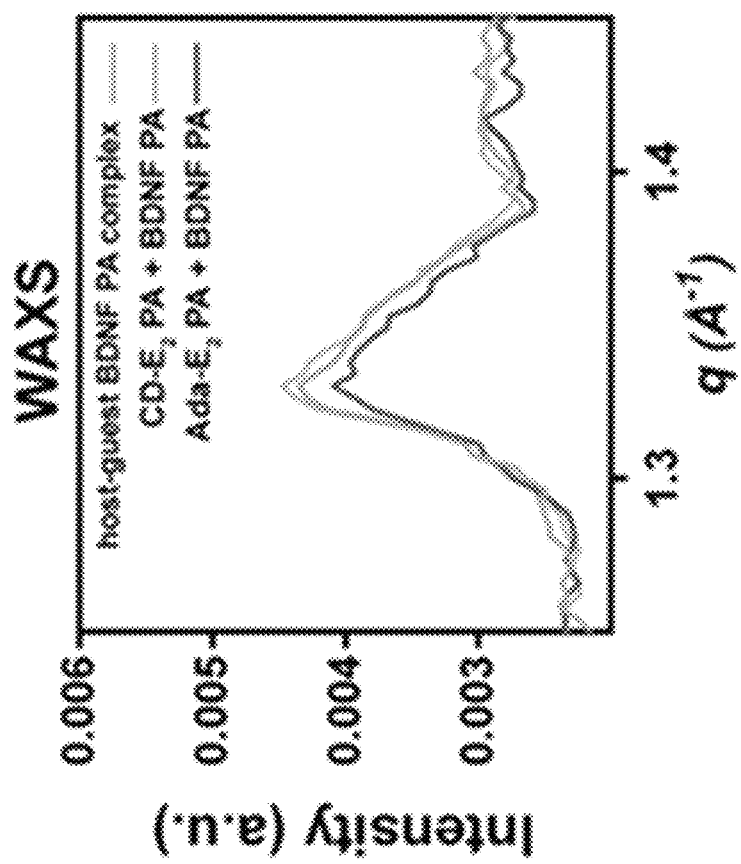
Figure 22C:
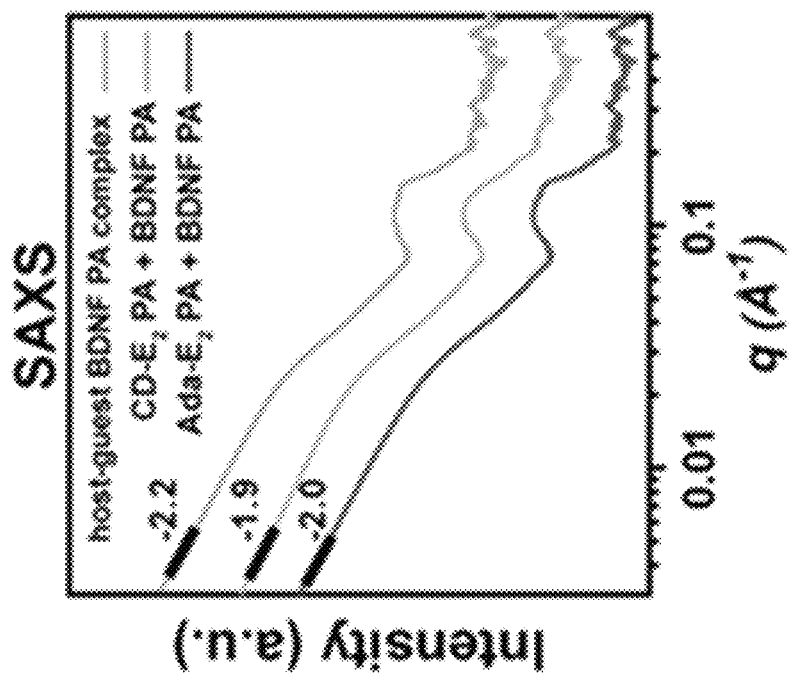
Figure 22E:
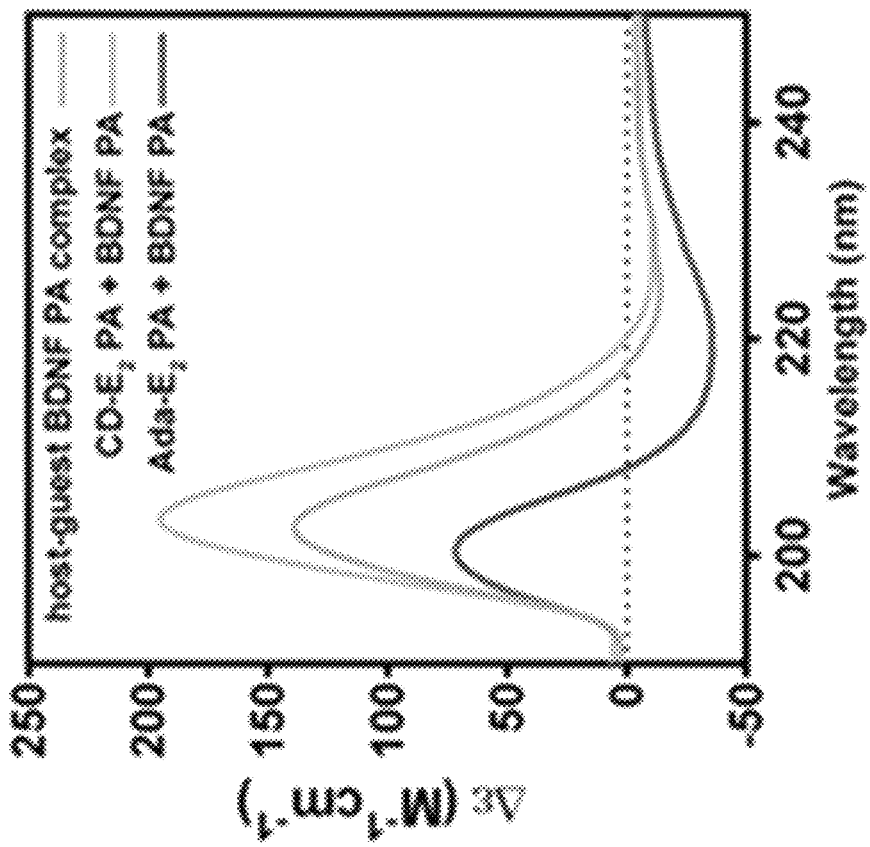
Figure 22G:
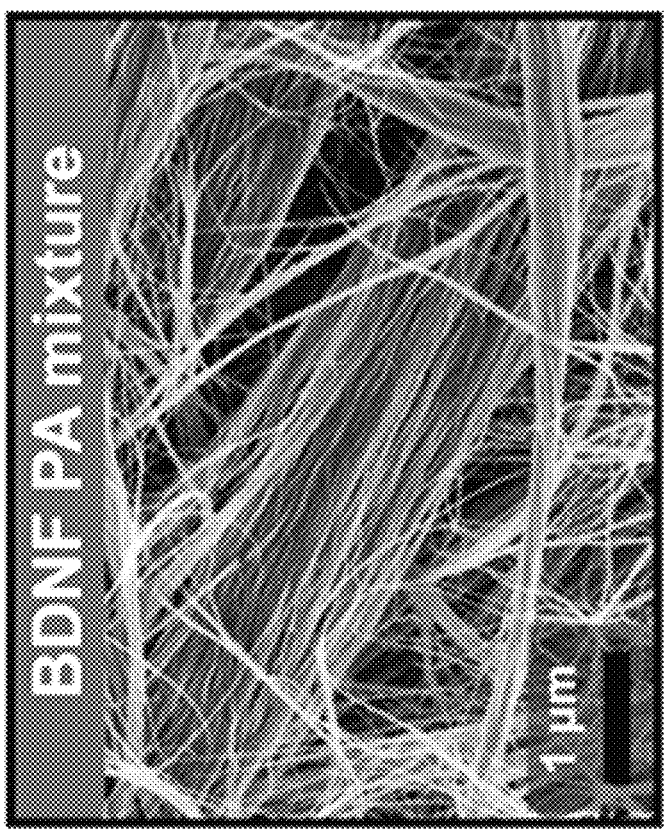
Figure 22F:
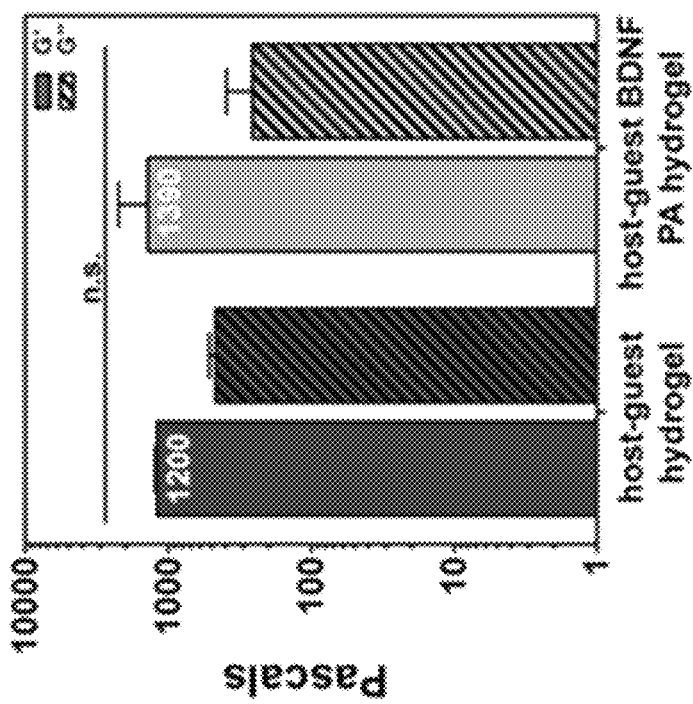
Figure 23B:
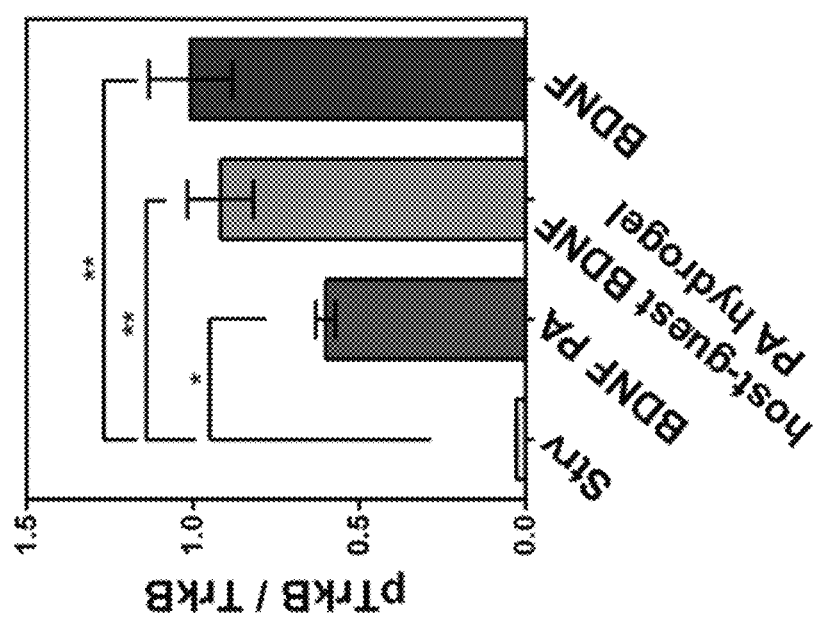
FIG. 23A-B. TrkB receptor activation of primary cortical neurons treated with BDNF superstructure.
Figure 23A:
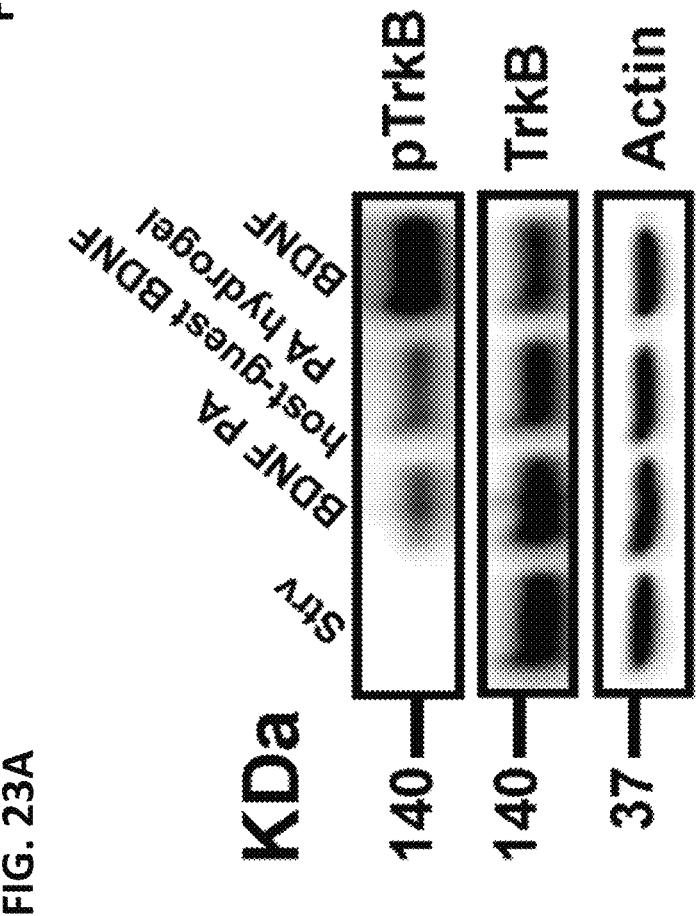
Figure 24A:
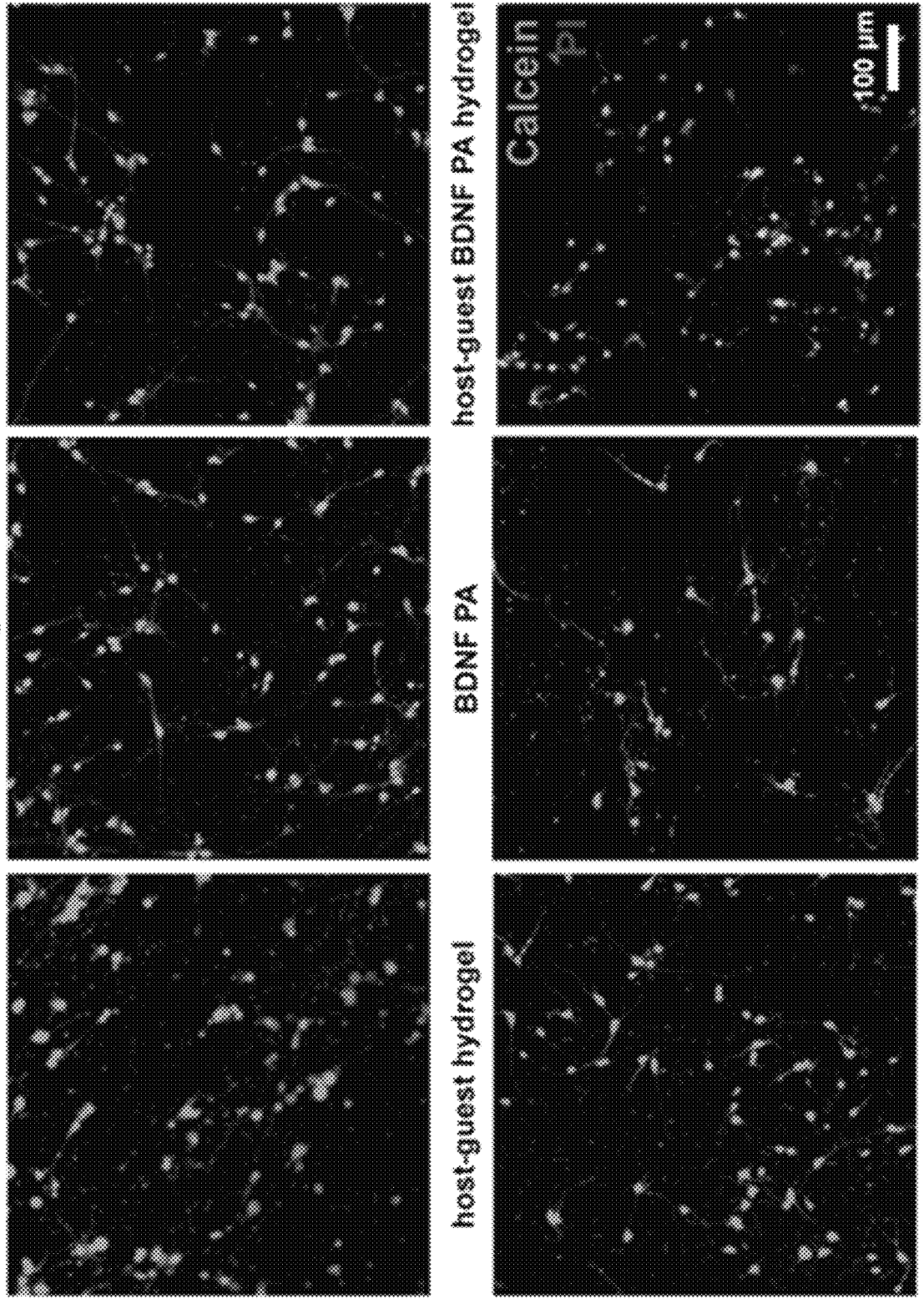
FIG. 24A-B. Live-Dead Analysis of embryonic primary cortical neurons seeded on 3D gels.
Figure 24B:
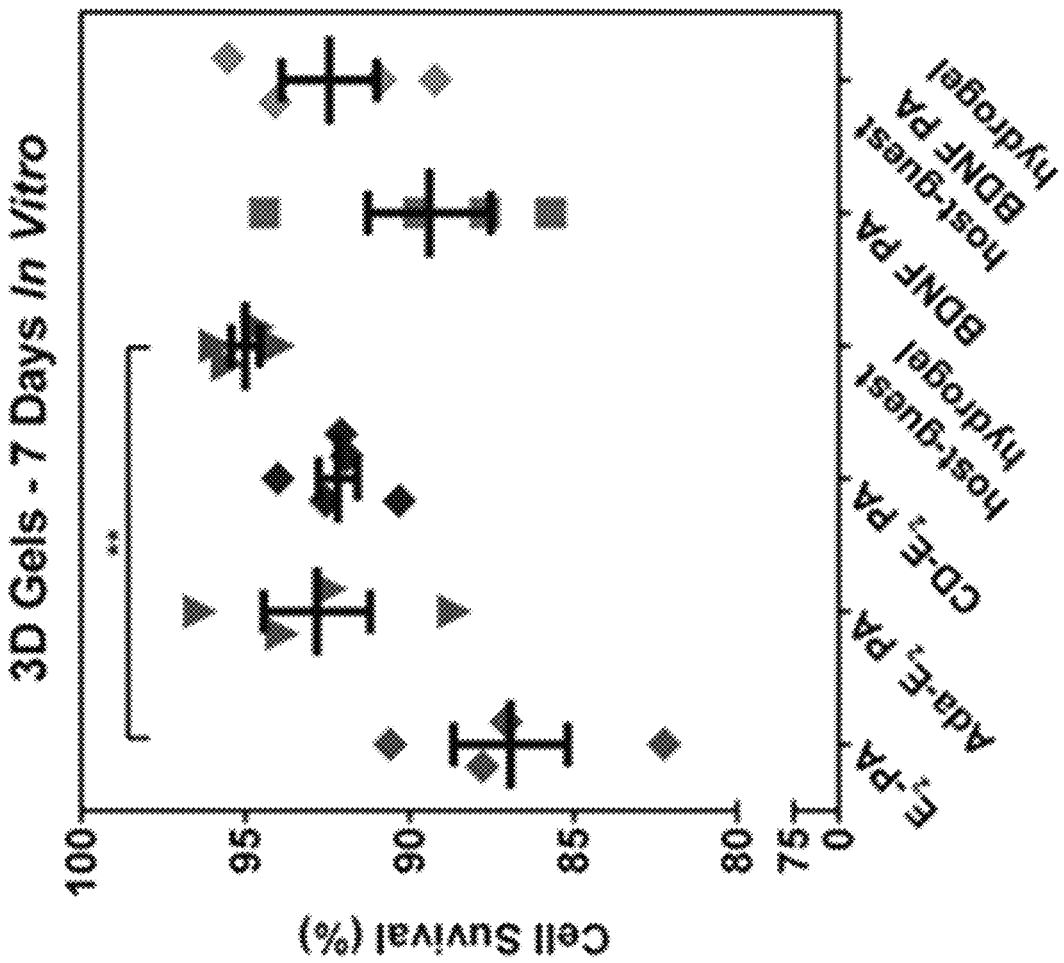

Cellular Response to the Incorporation of Bioactivity in the Host-Guest Biomaterial The effect of the superstructure on bioactivity was investigated by incorporating a PA molecule in the supramolecular system that has been shown to mimic brain-derived neurotrophic factor (BDNF PA).[30] The objective was to explore whether the addition of the host-guest moieties and their ability to create superstructures would interfere or enhance bioactivity. Thus the BDNF PA was co-assembled with the CD-$E_2$ PA at 10 mol % (10 mol % BDNF PA, 10 mol % cyclodextrin PA, and 80 mol % $E_2$ PA) and separately with the Ada-$E_2$ PA (10 mol % BDNF PA, 10 mol % adamantane PA, 80% $E_2$ PA) (FIG. 22a). The BDNF PA was co-assembled at 10 mol % within the host-guest hydrogel. The two PAs were mixed in a 1:1 ratio to form a superstructure that incorporates the BDNF PA. The properties of this supramolecular system do not differ significantly from the properties of the superstructure mixture without the BDNF PA (FIG. 22b-g). BDNF PA activates the BDNF specific TrkB receptor[30], accordingly receptor phosphorylation was also investigated using the supramolecular biomaterial. The host-guest BDNF PA mixture, BDNF PA, and BDNF protein alone were added to media to treat embryonic primary mouse cortical neurons in vitro, and the amount of phosphorylated receptor was quantified using Western blot analysis (FIG. 3a). The BDNF PA and BDNF superstructured materials induced similar levels of p-TrkB, and therefore it was concluded that the BDNF superstructured material bioactivity is not compromised relative to the BDNF PA (FIG. 23). To exclude the possibility of any cytotoxic effects of the CD-$E_2$ PA or Ada-$E_2$ PA, a cell viability assay was performed on primary cortical neurons seeded on 3D host-guest hydrogel scaffolds with and without the BDNF PA for 7 days in vitro. The cell survival remained above 80% for all conditions, which is indicative of a healthy primary culture (FIG. 3b and FIG. 24).

Figure 3C:
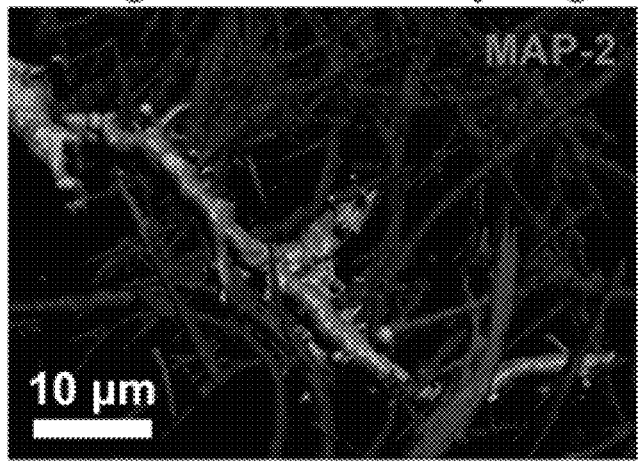
Figure 3D:
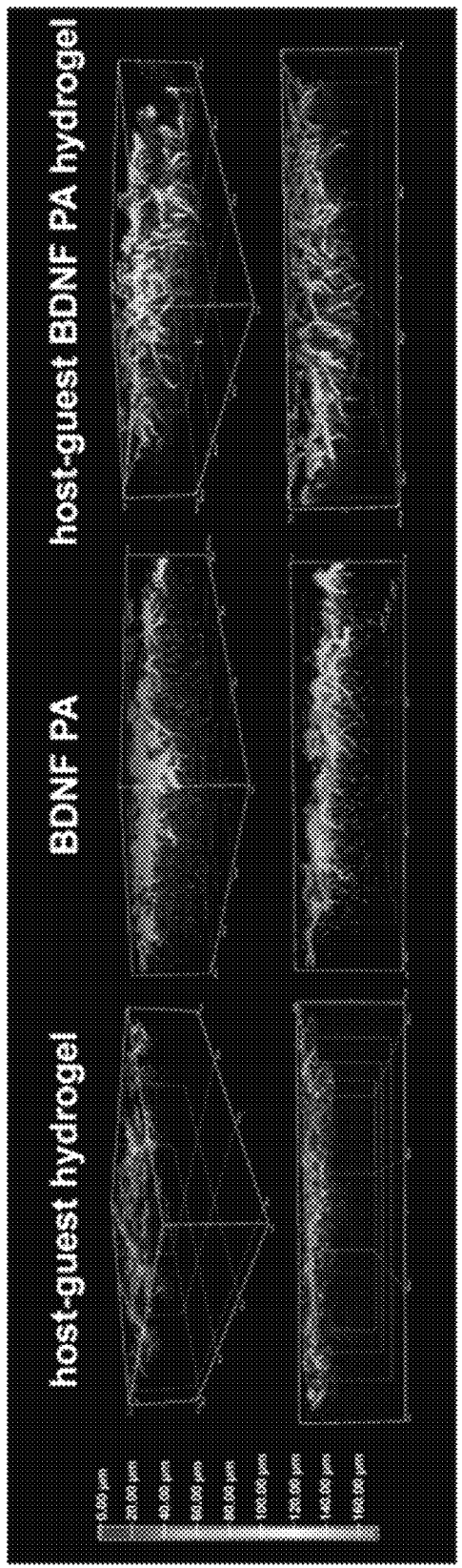
Figure 3E:
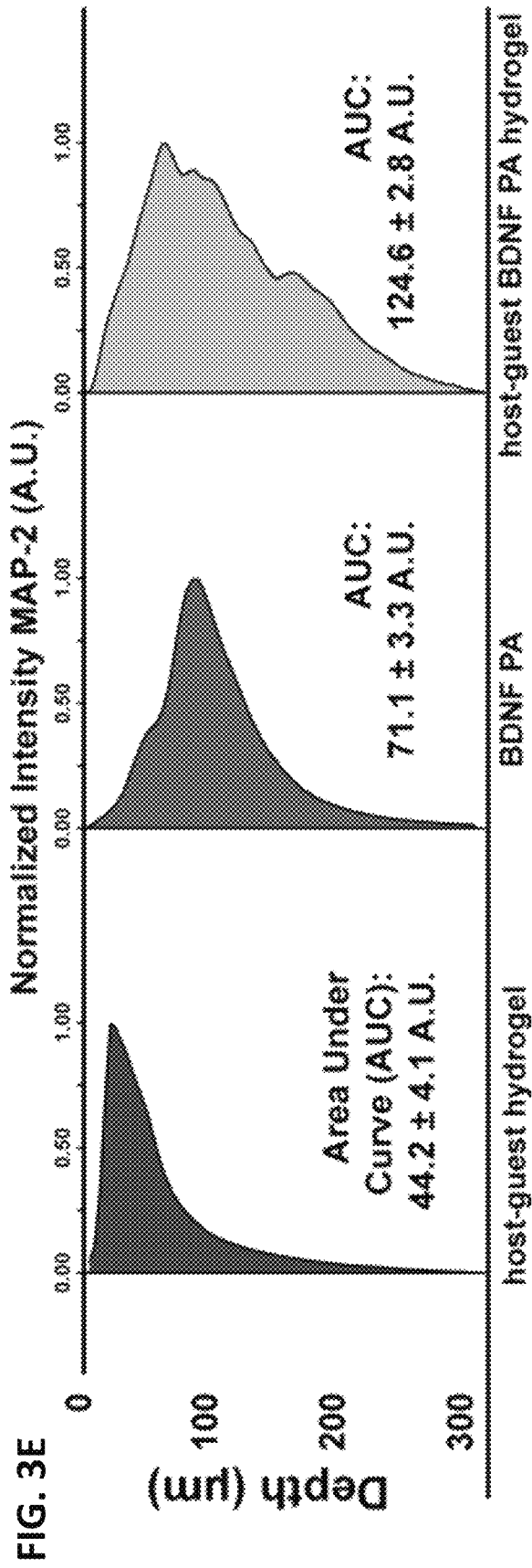
Figure 25A:
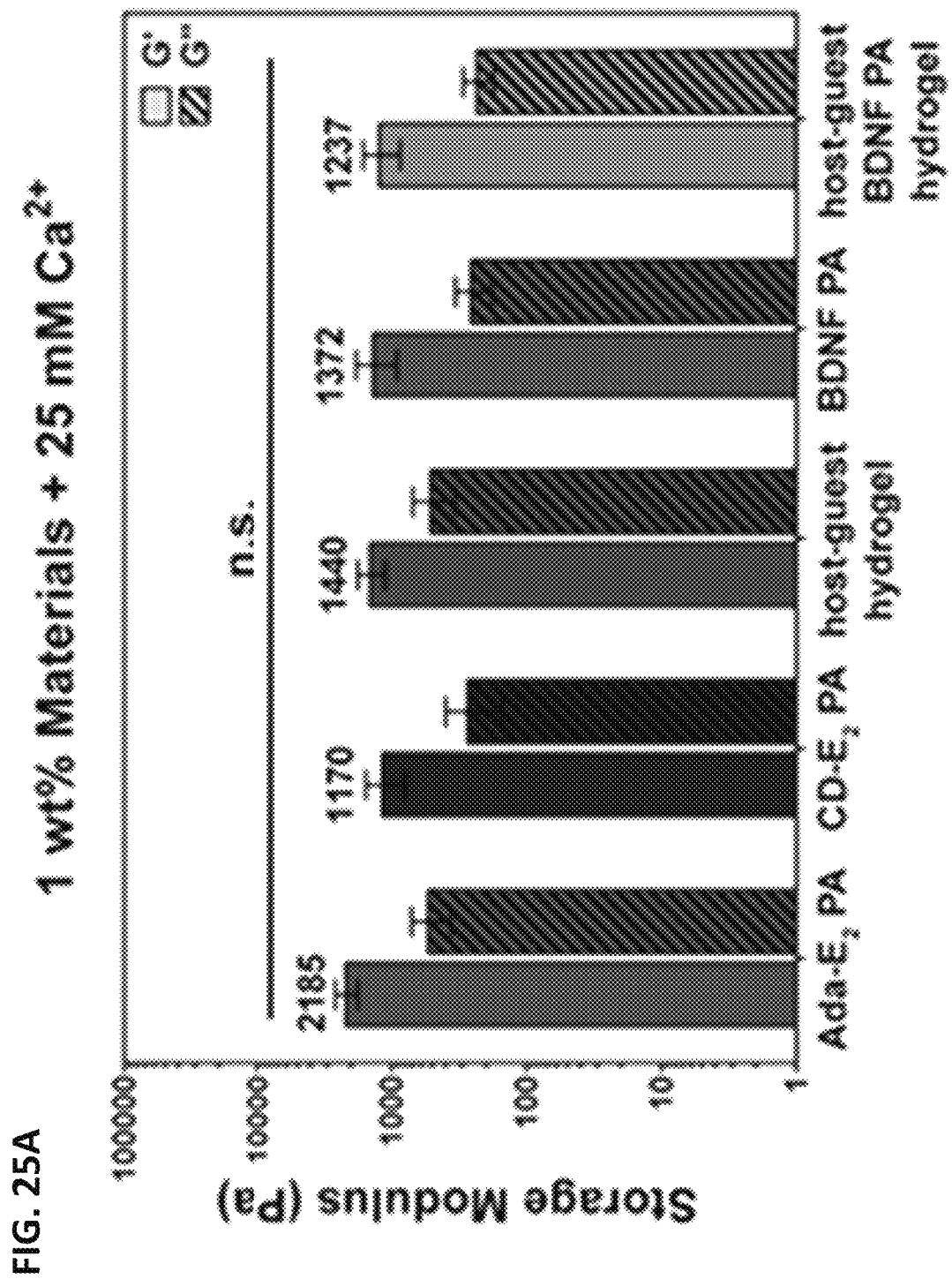
FIG. 25A-C. Rheological properties of PA scaffolds and infiltration of cortical neurons in PA scaffolds.
Figure 25B:
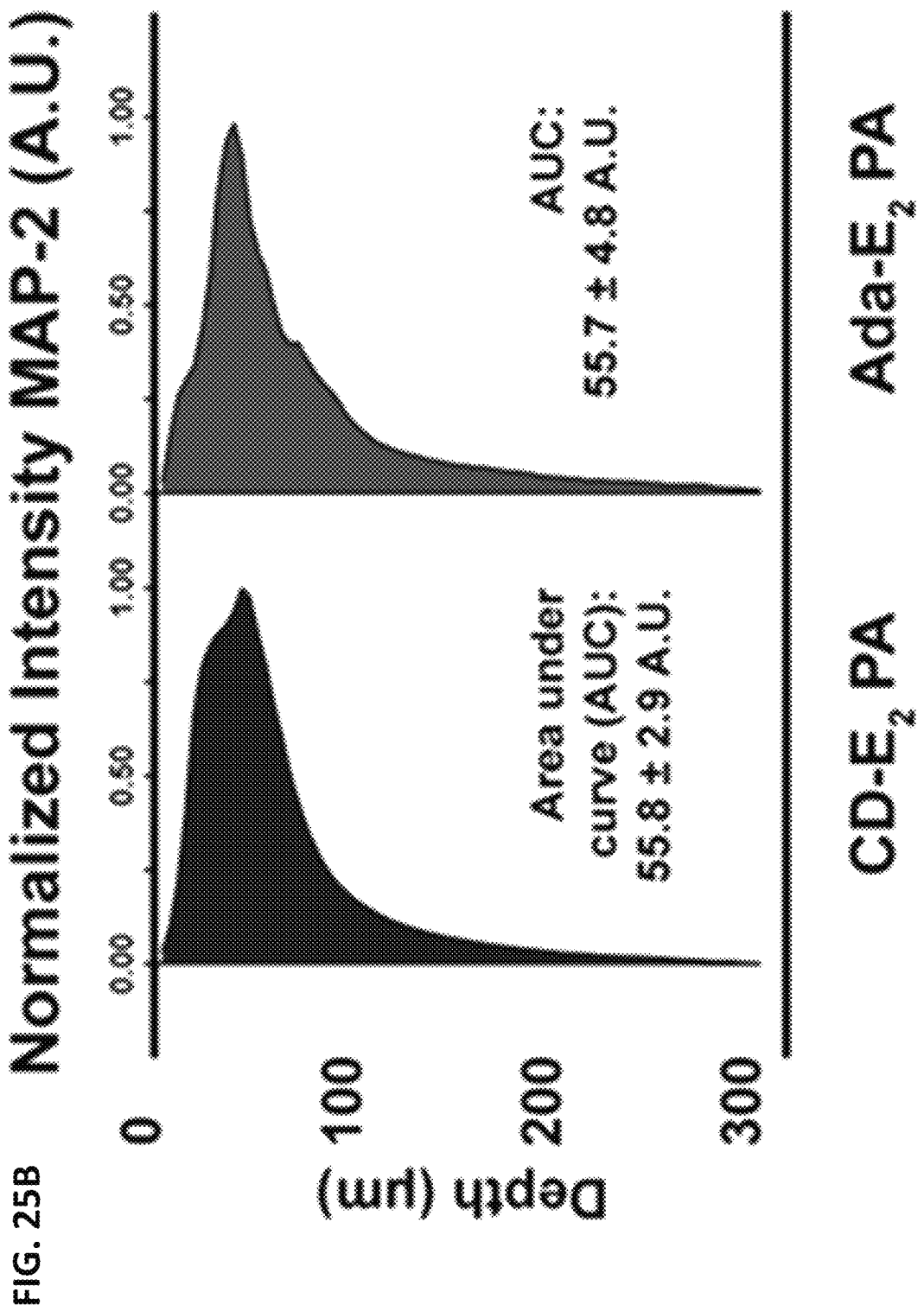
Figure 25C:
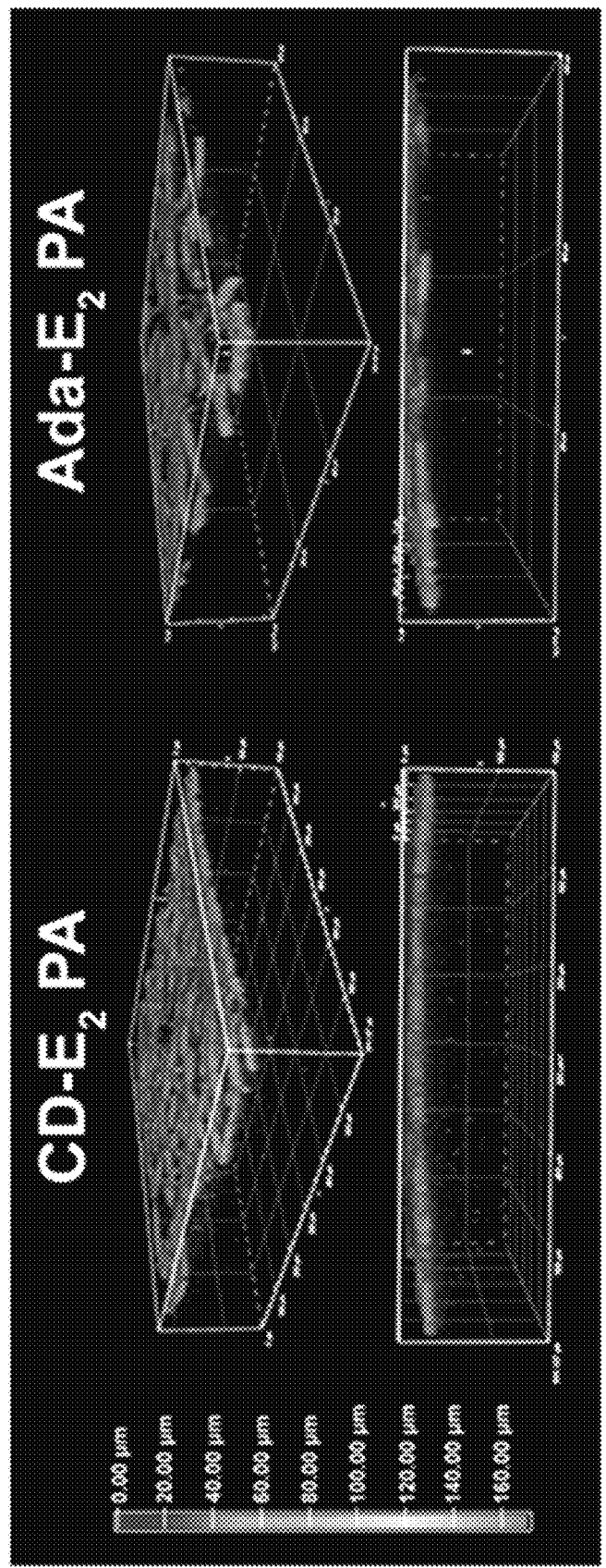
Figure 26E:
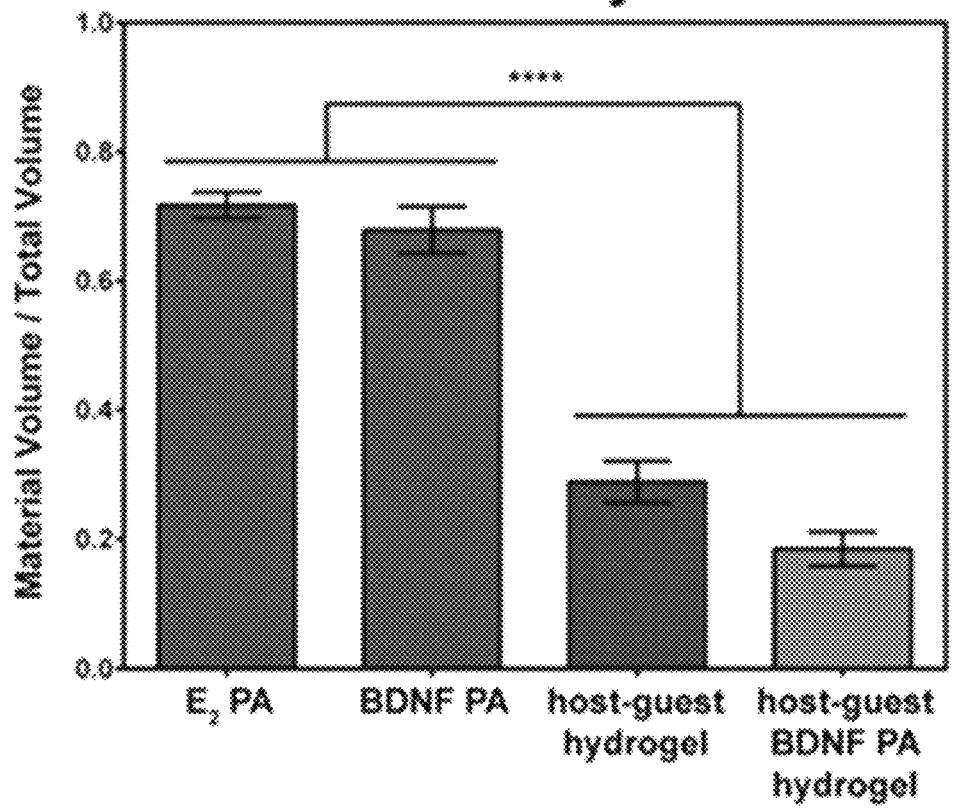

Next, it was investigated whether neurons could infiltrate gels of the BDNF superstructured material. The BDNF PA increases infiltration of primary cortical neurons on 3D PA gels[30], so it was evaluated if the superstructured material had an effect on BDNF PA-induced infiltration. Gels were prepared in a mold to create them with uniform size and degree of swelling after media addition for each gel condition tested and were subsequently seeded with neurons. Under the conditions used for in vitro testing (25 mM $Ca^{2+}$ was added to induce ionic crosslinking of the BDNF PA hydrogel as the modulus without calcium is not self-supporting (FIG. 14a)), the bioactive host-guest BDNF PA hydrogel, the BDNF PA alone, and the host-guest BDNF PA hydrogel all had a G' between 1.2 and 1.4 kPa which is within the range of mechanical properties of neural tissue (FIG. 25a).[50] The cells were grown for 1 week in vitro and the depth of infiltration of the neurons was analyzed using microtubule associated protein 2 (MAP-2), a dendritic marker for phenotypic maturity. A shadow projection revealed that neurons were able to extend their dendrites and interweave them through the network of bundles within the superstructured material (FIG. 3c). Only cells seeded on the BDNF PA and the host-guest BDNF PA hydrogel induced significant infiltration over 50 μm (FIG. 3d and FIG. 25b-c). The host-guest BDNF PA hydrogel facilitated the growth of the most widely distributed network of neurons throughout the depth of the gel as shown by comparing the area under the curve (AUC) of normalized MAP-2 intensity vs depth in the host-guest BDNF PA hydrogel, the BDNF PA, and the host-guest hydrogel having AUC values of 124.6±2.8, 71.1±3.3., and 44.2±4.4, respectively (FIG. 3e). It was hypothesized that this greater infiltration in the host-guest BDNF PA hydrogel is due to two factors. First, it is necessary for the cells to sense the BDNF mimetic signal on the supramolecular polymers to induce any infiltration, which is supported by the lower infiltration in the case of the host-guest hydrogel without the BDNF PA incorporated. The striking differences in cell response on the host-guest hydrogel and its BDNF-functionalized equivalent, which have the same storage modulus and are therefore the same from a mechanobiology perspective, suggest that cells are initially responding to the BDNF signal and the stiffness of the scaffold is not playing a critical role. Second, it was hypothesized that the ability of cells to infiltrate the bioactive material is enhanced by the additional porosity of the superstructured scaffold. Confocal z-stacks were taken of $E_2$-405 labeled gels, and shadow projections were used to analyze the various samples. It was found that the host-guest hydrogel and the host-guest BDNF PA hydrogel contained large pores as indicated by a significantly lower ratio of material volume to total scaffold volume (FIG. 26). Therefore, the BDNF signal in conjunction with enhanced porosity generated by the superstructure formation is thought to enable neurons to penetrate deeper into the PA network (FIG. 3f). Taken together, these results show that the self-assembly of the hierarchical superstructure is able to enhance neuronal bioactivity of PAs in vitro.

3D Printing of the Superstructured PAs

Figure 4B:
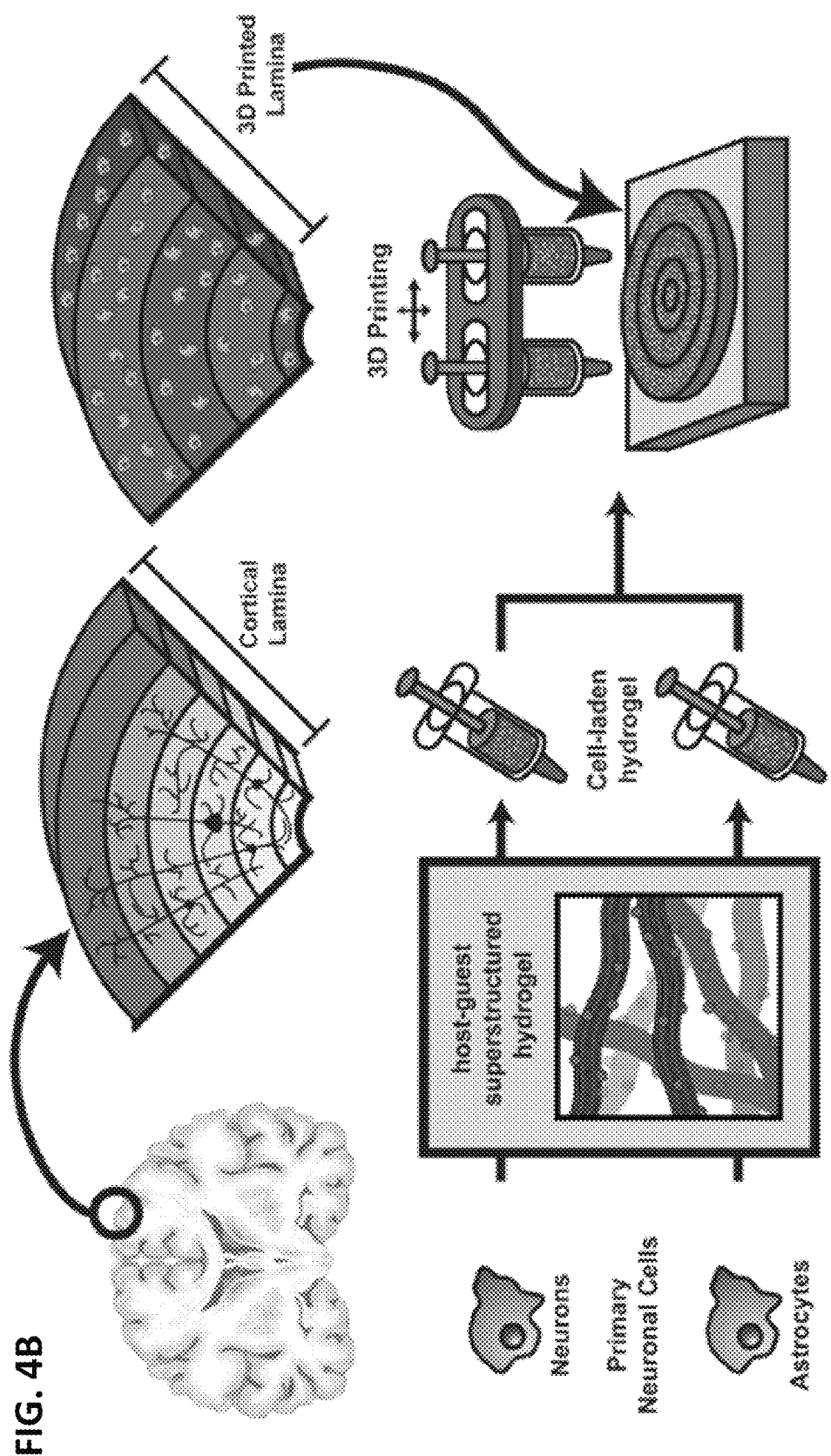

The effect of superstructure formation on the three-dimensional (3D) printing capabilities of the peptide amphiphile gels was evaluated. The goal was to print the PA material into self-standing objects without adding a layer of divalent cations to the printing surface[51] which does not allow for gelation to occur beyond the first printed layer. It was also desirable to avoid the need for incorporating additive molecules, as these may compromise some of the materials properties and could limit applications. The second objective was to utilize the ability of the superstructured material to be co-assembled with bioactive epitopes in more complex forms for in vitro cell assays. 3D printing of neuronal cells in spatially defined scaffolds that can simulate the complexity of neural tissue for a variety of in vitro assays is an important but challenging goal.[52, 53] For example, extruding neuronal cells is particularly challenging since the bio-ink carrier must be of appropriate softness to avoid shearing cells during extrusion while subsequently maintaining an appropriate stiffness to hold-shape post-extrusion.[54] Creating a material that addresses this problem while presenting biologically relevant signals will create a versatile new platform for in vitro studies or tissue regeneration. Initially, the thixotropy of the superstructured material and the $E_2$ PA to determine their printability was studied. This was performed by conducting a rheological interval study to mimic the shear strain expected before, during, and after extrusion through a print head (FIG. 4a). During each phase, the storage and loss modulus were recorded for each material. After the crosslinks of the superstructured hydrogel are disrupted during high shear, its mechanical properties quickly recover to original values suggesting that the material's integrity could be maintained throughout the printing process, with a 113% recovery (before: G'=1199.8 Pa; after: G'=1361.5 Pa). Conversely, the $E_2$ PA had a much lower storage modulus initially which then further decreased significantly after exposure to high shear forces, and only 61% recovery (before: G'=43.9 Pa; after: G'=26.8 Pa). The observed recovery of mechanical properties after high shear implies that the superstructured material is capable of retaining a 3D printed shape following extrusion.

Figure 4D:
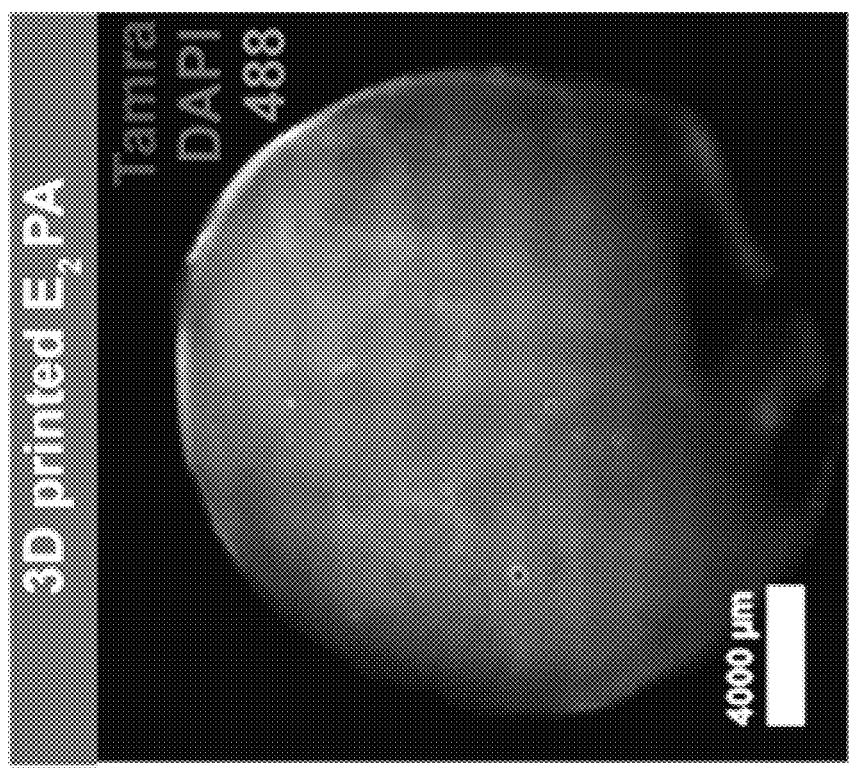
Figure 4C:
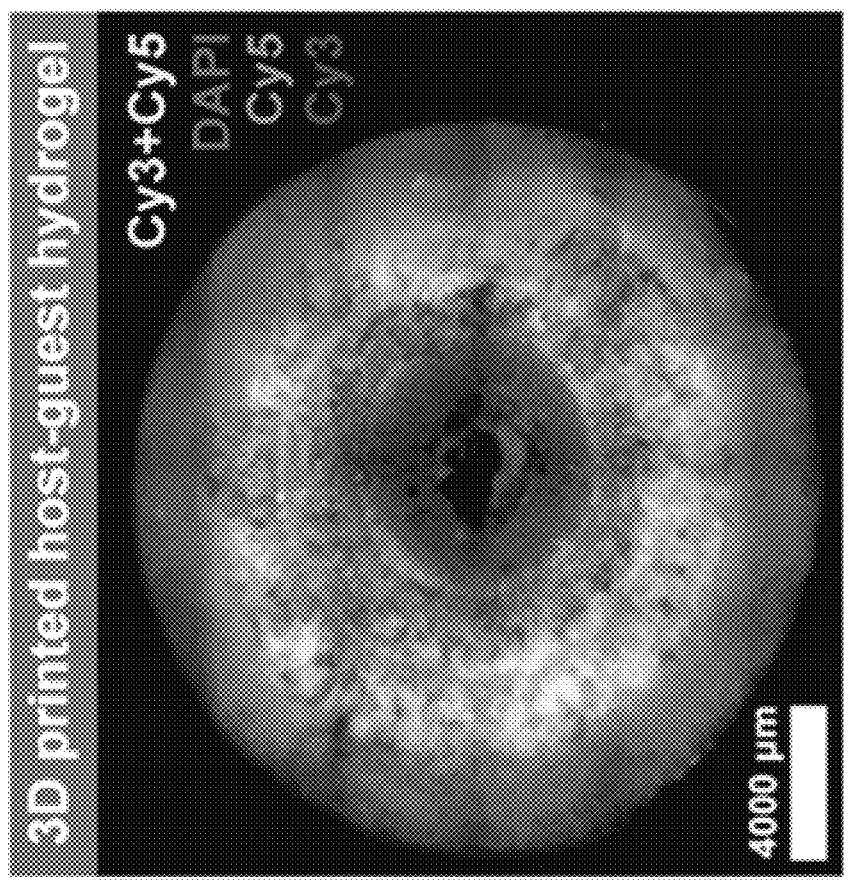
Figure 28A:
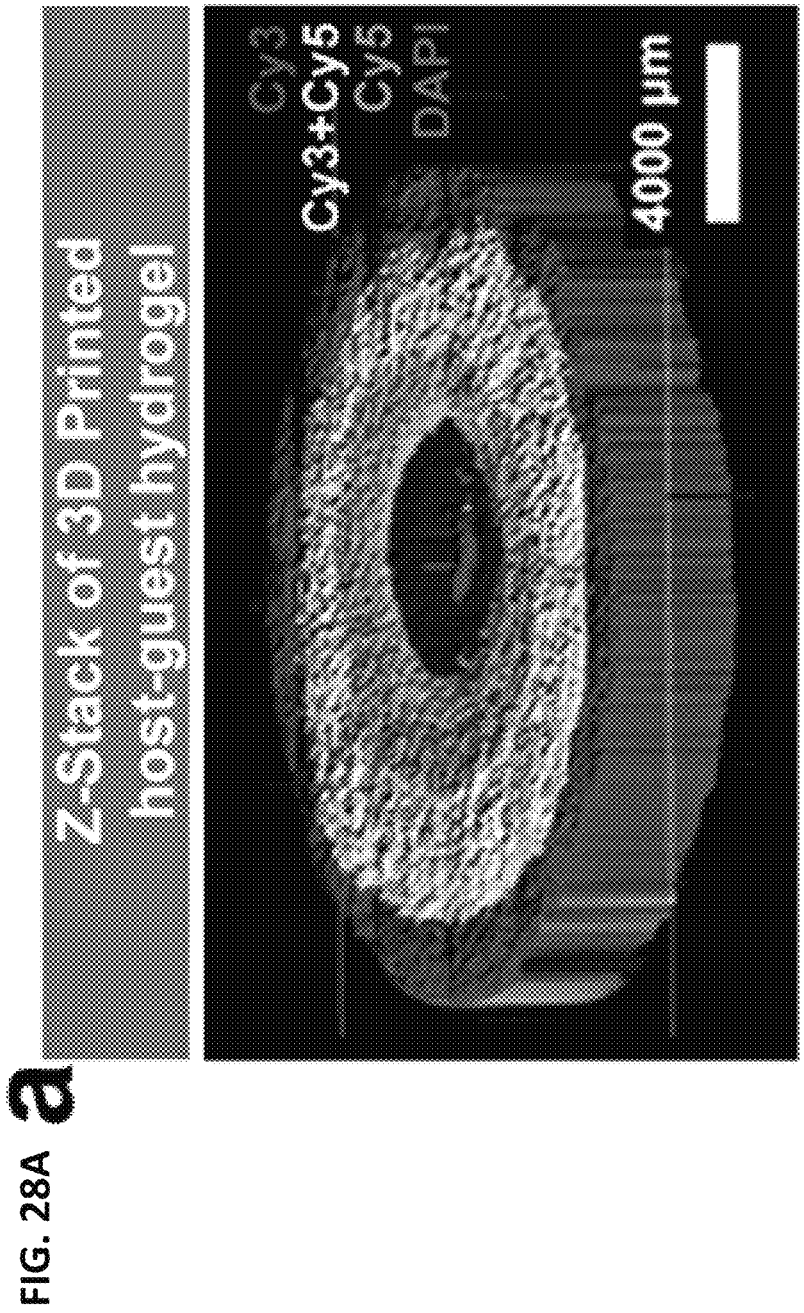
FIG. 28A-C. 3D printed concentric circles of the host-guest hydrogel.
Figure 28C:
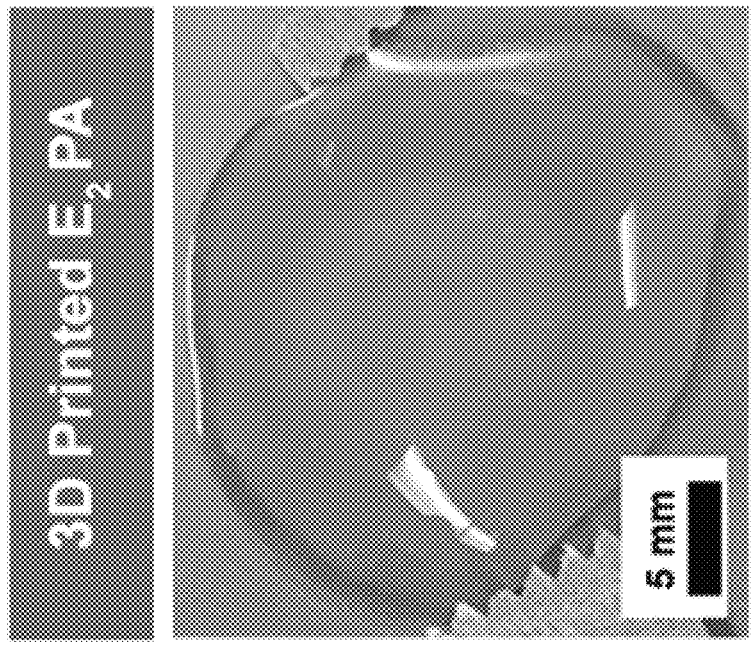
Figure 28B:
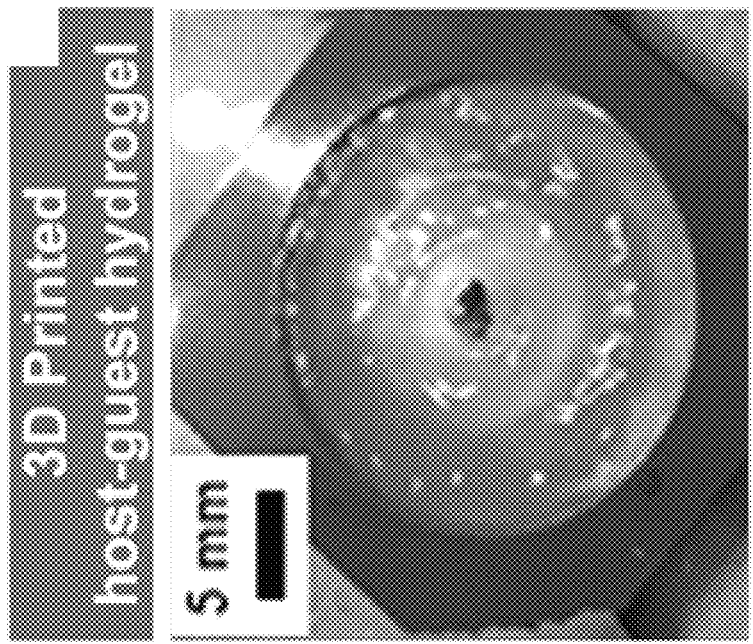
Figures 29A, 29B:
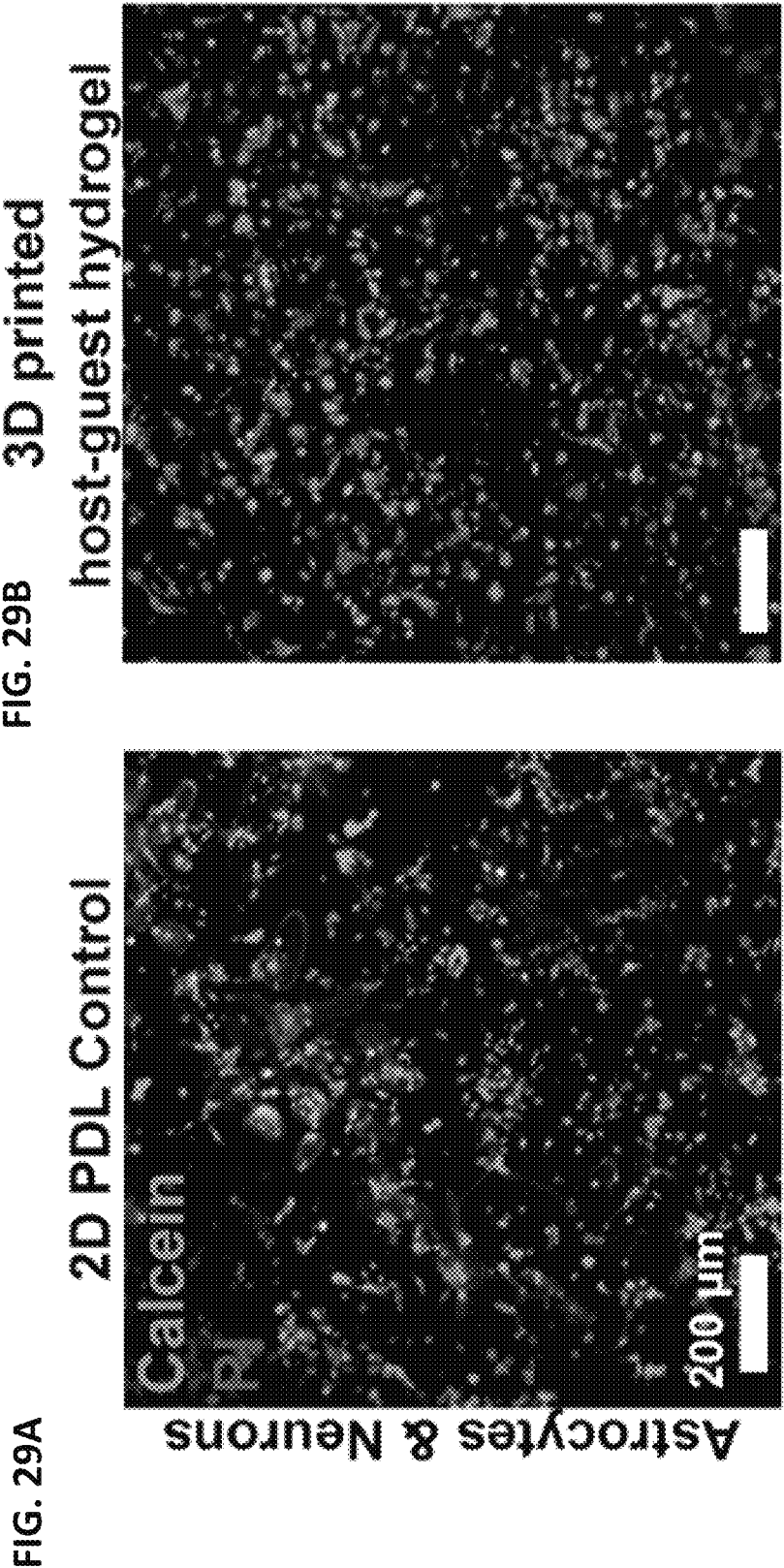
FIG. 29A-B. Live-Dead assay images. Confocal micrograph of primary cortical neurons and astrocytes stained for calcein (live marker, green) and propidium iodide (dead marker, red) of cells on a (FIG. 29A) 2D PDL control and (FIG. 29B) within the 3D printed host-guest hydrogel, both for 3 days in vitro.
Figure 30:
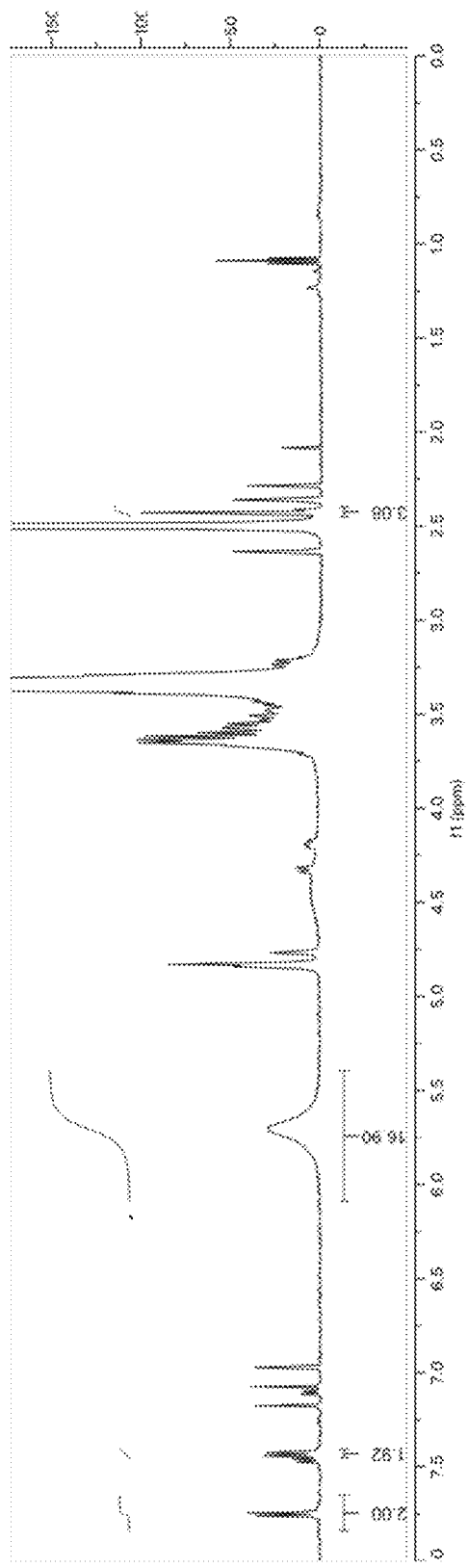
FIG. 30. $^1$H NMR spectrum of 6-O-monotosyl-6-deoxy-β-cyclodextrin (CD-tos).
Figure 31:
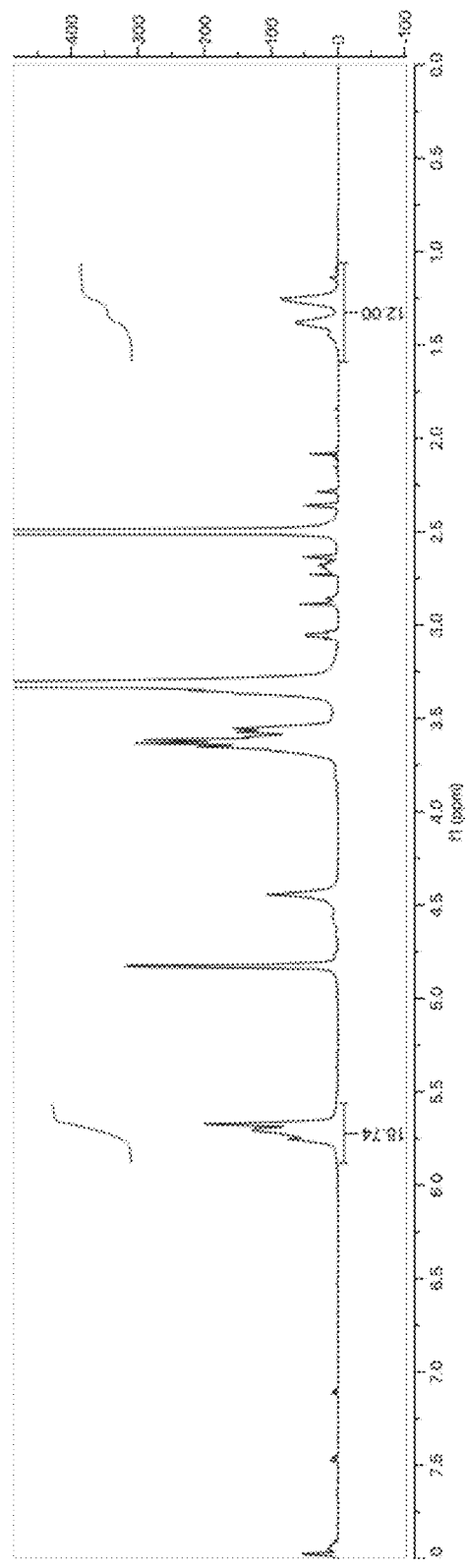
FIG. 31. $^1$H NMR spectrum of 6-(6-aminohexyl)amino-6-deoxy-β-cyclodextrin (CD-HDA).
Figure 32B:
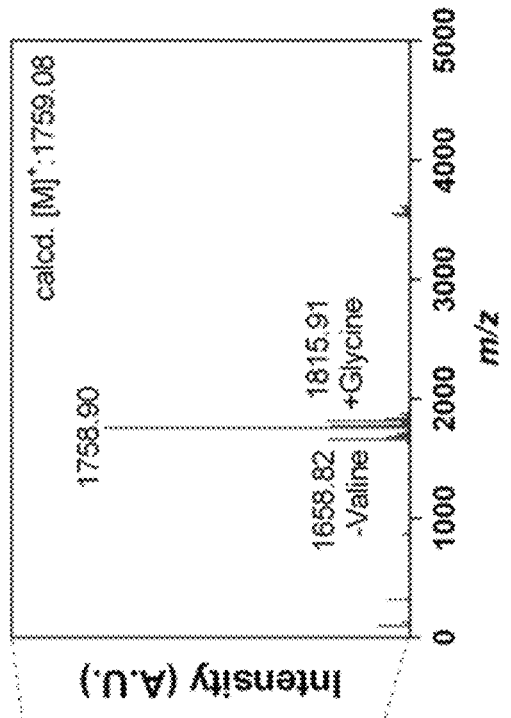
FIG. 32A-B. LCMS of the adamantane PA.
Figure 32A:
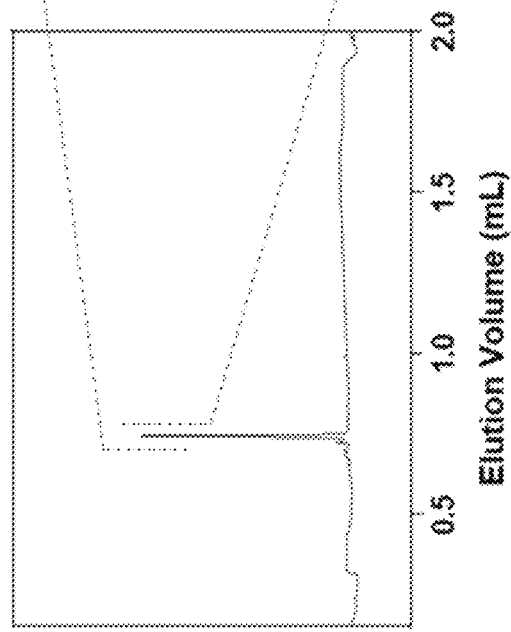
Figure 33A:
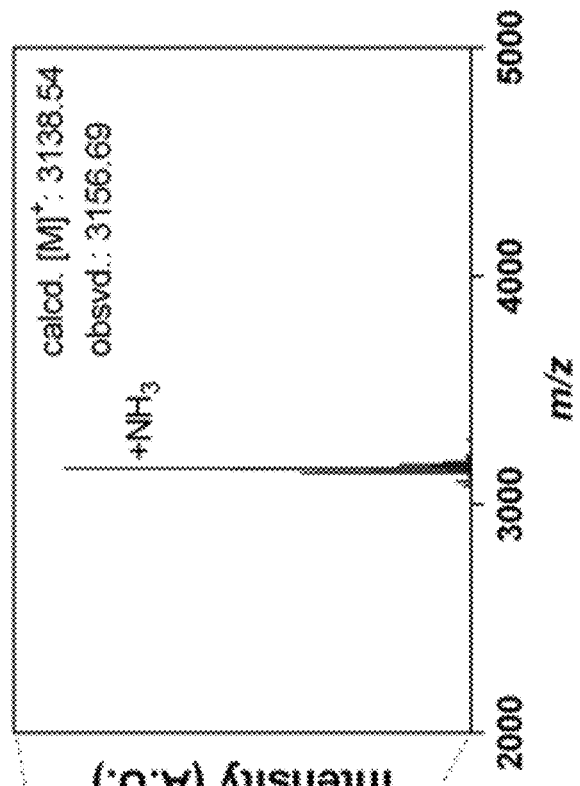
FIG. 33A-B. LCMS of the cyclodextrin PA.
Figure 33B:
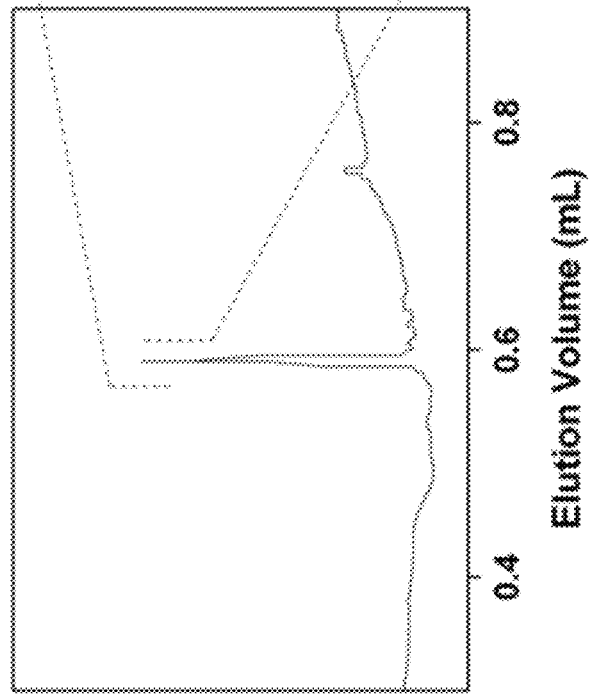
Figure 34B:
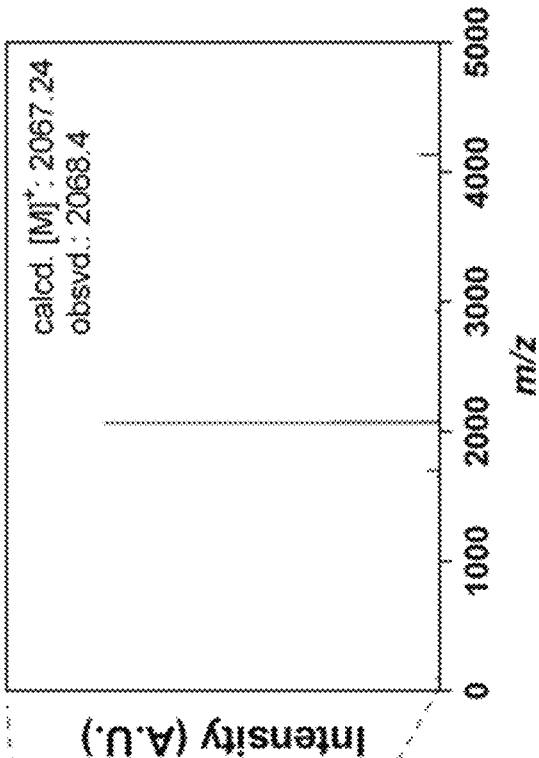
FIG. 34A-B. LCMS of the BDNF PA.
Figure 34A:
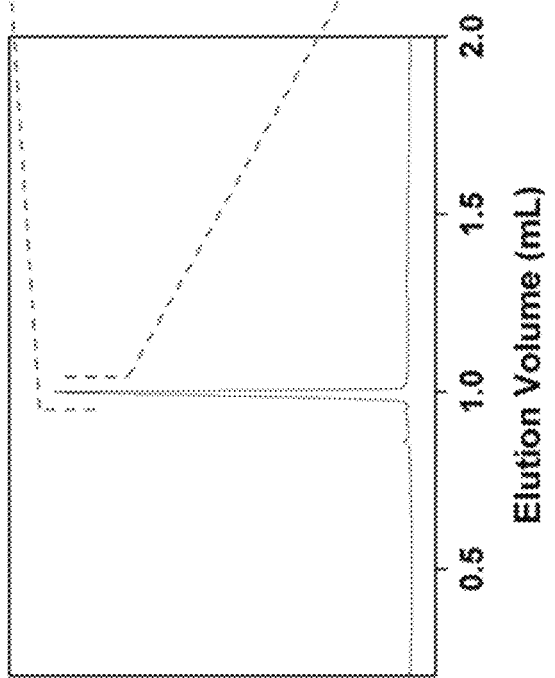

Once the shear recovery properties of the superstructured hydrogel were stablished, multiple superstructured inks laden with different cell types and bioactive cues were prepared. These inks could be printed in concentric circles to mimic the natural organization of the layers found within the brain cortex as well as into ordered macroporous self-supporting hydrogels (FIG. 4b and FIG. 27).[55] The addition of cells to the host-guest hydrogel did not visually change the properties of the material suggesting that the presence of cells did not impede host-guest interactions or restrict superstructure formation. To test if this was possible, several fluorophore-labeled inks were used to allow visualization. When printed, the superstructured material held its shape and microscopy revealed clearly layers with distinct colors, confirming the possibility of printing complex patterns (FIG. 4c and FIG. 28a-b). In contrast the 3D printed $E_2$ PA behaved as a liquid droplet and the spatial resolution was highly dependent on the print speed (FIG. 28c) since the layers quickly deform as the liquid relaxed over time. Within the one hour elapsed between printing and imaging, the $E_2$ PA samples did not contain distinct concentric layers (FIG. 4d).

Figure 4F:
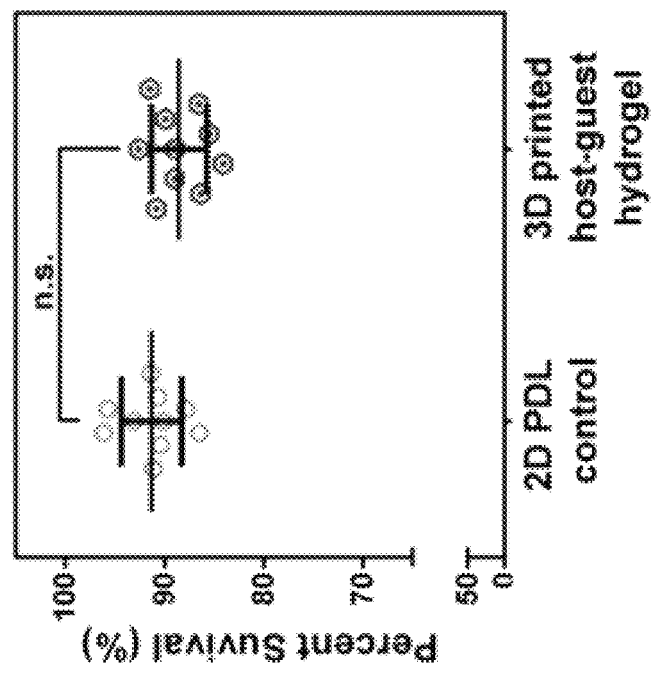
Figure 4E:
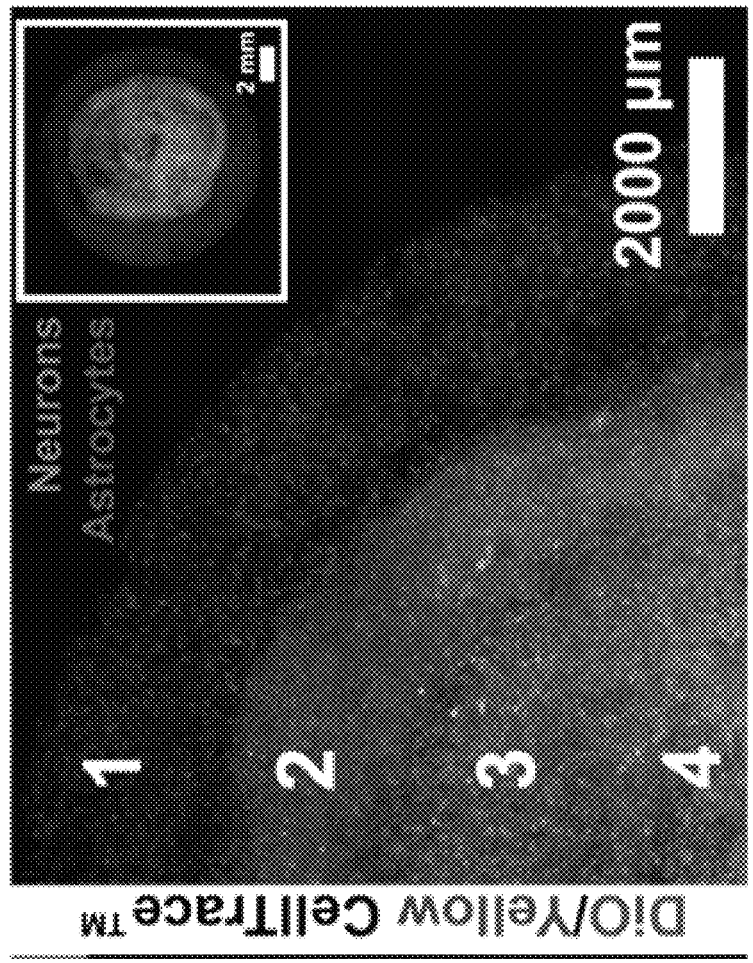

Next, primary cortical astrocytes and neurons—the two major cell types in the CNS—were isolated from mice (at P0 and E16 respectively) and incorporated into the superstructured ink to further mimic the composition of CNS tissue, and tested for cell viability. Neurons were labeled with a membrane-intercalating dye called Vybrant™ DiO and astrocytes with Yellow Celltrace™ prior to printing. Cells were printed in a sequential pattern to simulate the layer-specific morphological and biochemical differences that prevail within the brain cortex as glial cells support neuron growth during development and beyond.[56] The layers were also printed with the bioactive host-guest BDNF PA hydrogel and the different cell types. The 3D printed scaffolds were then cultured for 7 days in vitro and later imaged (FIG. 4e). After this period of time, the cells were evenly distributed throughout the 3D printed layers and the host-guest hydrogels maintained spatial resolution of their layered pattern. Furthermore, during these experiments no evidence of hydrogel degradation was found, consistent with previous studies which have demonstrated the presence of peptide amphiphile hydrogels for two weeks in a relevant in vivo model of muscle regeneration.[28] To assess cell viability, a live/dead assay was conducted 3 days after printing using calcein and propidium iodide, and the cell survival was quantified (FIG. 4f and FIG. S25). The superstructured material had a cell survival of 89±3% and was not statistically different from cells grown on the positive control which was a two-dimensional (2D) poly-D-lysine (PDL) coated coverslip with a percent survival of 91±3%, confirming that the 3D printing process did not substantially affect cell viability. This work demonstrated the ability of the superstructured materials to not only be printed into complex shapes, but also incorporate a bioactive signal and different cell types to better mimic tissue architectures.

CONCLUSIONS

Demonstrated herein is the use of monomer exchange dynamics in mixtures of two supramolecular polymers to create a superstructured hydrogel containing domains with highly concentrated host-guest interactions. These interactions can be molecularly tuned to obtain a specific storage modulus or to change it by adding molecules that disrupt the host-guest complex. The complexes can be disrupted under high shear to enable 3D printing of these materials but following recovery of the structure, printed objects are able to maintain their shapes and layered patterns. Finally, the potential for use of these hydrogels as bioactive supramolecular biomaterials is demonstrated herein, by co-assembling bioactive monomers that promote the infiltration of neurons and also activate a neuronal receptor.

REFERENCES

[1] M. L. Gardel, J. H. Shin, F. C. Mackintosh, L. Mahadevan, P. Matsudaira, D. A. Weitz, Science 2004, 304, 1301.
[2] E. Karsenti, Nat Rev Mol Cell Bio 2008, 9, 255.
[3] D. Needleman, Z. Dogic, Nat Rev Mater 2017, 2.
[4] G. M. Whitesides, B. Grzybowski, Science 2002, 295, 2418.
[5] S. Datta, M. L. Saha, P. J. Stang, Accounts Chem Res 2018, 51, 2047.
[6] C. Rest, R. Kandanelli, G. Fernandez, Chem Soc Rev 2015, 44, 2573.

[7] S. I. Stupp, T. D. Clemons, J. K. Carrow, H. Sai, L. C. Palmer, *Israel Journal of Chemistry* 2020, 60, 1.
[8] R. Freeman, M. Han, Z. Alvarez, J. A. Lewis, J. R. Wester, N. Stephanopoulos, M. T. Mcclendon, C. Lynsky, J. M. Godbe, H. Sangji, E. Luijten, S. I. Stupp, *Science* 2018, 362, 808.
[9] L. Albertazzi, D. van der Zwaag, C. M. A. Leenders, R. Fitzner, R. W. van der Hofstad, E. W. Meijer, *Science* 2014, 344, 491.
[10] R. M. P. da Silva, D. van der Zwaag, L. Albertazzi, S. S. Lee, E. W. Meijer, S. I. Stupp, *Nat Commun* 2016, 711561/1-10.
[11] J. R. Wester, J. Lewis, R. Freeman, H. Sai, L. Palmer, S. Henrich, S. Stupp, *Journal of the American Chemical Society* 2020, 142, 12216.
[12] J. C. Harrison, M. R. Eftink, *Biopolymers* 1982, 21, 1153.
[13] W. C. Cromwell, K. Bystrom, M. R. Eftink, *J Phys Chem-Us* 1985, 89, 326.
[14] J. Boekhoven, C. M. R. Perez, S. Sur, A. Worthy, S. I. Stupp, *Angew Chem Int Edit* 2013, 52, 12077.
[15] C. X. Ma, T. F. Li, Q. Zhao, X. X. Yang, J. J. Wu, Y. W. Luo, T. Xie, *Advanced Materials* 2014, 26, 5665.
[16] Q. Yan, Y. Zhao, *Chem Sci* 2015, 6, 4343.
[17] Q. Yan, H. J. Zhang, Y. Zhao, *ACS Macro Lett* 2014, 3, 472.
[18] C. Y. Quan, J. X. Chen, H. Y. Wang, C. Li, C. Chang, X. Z. Zhang, R. X. Zhuo, *ACS Nano* 2010, 4, 4211.
[19] K. H. Song, C. B. Highley, A. Rouff, J. A. Burdick, *Adv Funct Mater* 2018, 28.
[20] S. Hamsici, G. Cinar, A. Celebioglu, T. Uyar, A. B. Tekinay, M. O. Guler, *J Mater Chem* B 2017, 5, 517.
[21] M. Nakahata, Y. Takashima, H. Yamaguchi, A. Harada, *Nat Commun* 2011, 2.
[22] Y. Takashima, S. Hatanaka, M. Otsubo, M. Nakahata, T. Kakuta, A. Hashidzume, H. Yamaguchi, A. Harada, *Nat Commun* 2012, 3.
[23] T. Nakamura, Y. Takashima, A. Hashidzume, H. Yamaguchi, A. Harada, *Nat Commun* 2014, 5.
[24] C. Redondo-Gomez, Y. Abdouni, C. R. Becer, A. Mata, *Biomacromolecules* 2019, 20, 2276.
[25] M. K. Klein, H. A. Kassam, R. H. Lee, W. Bergmeier, E. B. Peters, D. C. Gillis, B. R. Dandurand, J. R. Rouan, M. R. Karver, M. D. Struble, T. D. Clemons, L. C. Palmer, B. Gavitt, T. A. Pritts, N. D. Tsihlis, S. I. Stupp, M. R. Kibbe, *ACS Nano* 2020, 14, 6649.
[26] S. S. Lee, T. Fyrner, F. Chen, Z. Alvarez, E. Sleep, D. S. Chun, J. A. Weiner, R. W. Cook, R. D. Freshman, M. S. Schallmo, K. M. Katchko, A. D. Schneider, J. T. Smith, C. W. Yun, G. Singh, S. Z. Hashmi, M. T. Mcclendon, Z. L. Yu, S. R. Stock, W. K. Hsu, E. L. Hsu, S. I. Stupp, *Nat Nanotechnol* 2017, 12, 821.
[27] G. A. Silva, C. Czeisler, K. L. Niece, E. Beniash, D. A. Harrington, J. A. Kessler, S. I. Stupp, *Science* 2004, 303, 1352.
[28] E. Sleep, B. D. Cosgrove, M. T. Mcclendon, A. T. Preslar, C. H. Chen, M. H. Sangji, C. M. R. Perez, R. D. Haynes, T. J. Meade, H. M. Blau, S. I. Stupp, *P Natl Acad Sci USA* 2017, 114, E7919.
[29] M. J. Webber, J. Tongers, C. J. Newcomb, K. T. Marquardt, J. Bauersachs, D. W. Losordo, S. I. Stupp, *P Natl Acad Sci USA* 2011, 108, 13438.
[30] A. N. Edelbrock, Z. Alvarez, D. Simkin, T. Fyrner, S. M. Chin, K. Sato, E. Kiskinis, S. I. Stupp, *Nano Lett* 2018, 18, 6237.
[31] T. D. Clemons, M. Challenor, M. Fitzgerald, S. A. Dunlop, N. M. Smith, K. S. Iyer, *ACS Macro Lett* 2016, 5, 1132.
[32] K. C. Spencer, J. C. Sy, K. B. Ramadi, A. M. Graybiel, R. Langer, M. J. Cima, *Sci Rep*-Uk 2017, 7.
[33] M. Zhang, X. H. Li, Y. D. Gong, N. M. Zhao, X. F. Zhang, *Biomaterials* 2002, 23, 2641.
[34] J. E. Goldberger, E. J. Berns, R. Bitton, C. J. Newcomb, S. I. Stupp, *Angew Chem Int Edit* 2011, 50, 6292.
[35] E. J. Berns, Z. Alvarez, J. E. Goldberger, J. Boekhoven, J. A. Kessler, H. G. Kuhn, S. I. Stupp, *Acta Biomaterialia* 2016, 37, 50.
[36] F. Tantakitti, J. Boekhoven, X. Wang, R. V. Kazantsev, T. Yu, J. H. Li, E. Zhuang, R. Zandi, J. H. Ortony, C. J. Newcomb, L. C. Palmer, G. S. Shekhawat, M. Olvera de la Cruz, G. C. Schatz, S. I. Stupp, *Nat Mater* 2016, 15, 469.
[37] T. J. Moyer, H. G. Cui, S. I. Stupp, *J Phys Chem B* 2013, 117, 4604.
[38] H. G. Cui, A. G. Cheetham, E. T. Pashuck, S. I. Stupp, *Journal of the American Chemical Society* 2014, 136, 12461.
[39] D. A. Kirschner, C. Abraham, D. J. Selkoe, *P Natl Acad Sci USA* 1986, 83, 503.
[40] J. T. Nguyen, H. Inouye, M. A. Baldwin, R. J. Fletterick, F. E. Cohen, S. B. Prusiner, D. A. Kirschner, *J Mol Biol* 1995, 252, 412.
[41] N. Greenfield, *Nat Protoc* 2006, 1, 2876.
[42] E. T. Pashuck, H. G. Cui, S. I. Stupp, *Journal of the American Chemical Society* 2010, 132, 6041.
[43] M. C. Manning, M. Illangasekare, R. W. Woody, *Biophys Chem* 1988, 31, 77.
[44] A. Micsonai, F. Wien, L. Kernya, Y. H. Lee, Y. Goto, M. Refregiers, J. Kardos, *P Natl Acad Sci USA* 2015, 112, E3095.
[45] H. Y. Yang, S. N. Yang, J. L. Kong, A. C. Dong, S. N. Yu, *Nat Protoc* 2015, 10.
[46] C. B. Rodell, A. L. Kaminski, J. A. Burdick, *Biomacromolecules* 2013, 14, 4125.
[47] E. M. M. Manders, J. Stap, G. J. Brakenhoff, R. Vandriel, J. A. Aten, *J Cell Sci* 1992, 103, 857.
[48] K. W. Dunn, M. M. Kamocka, J. H. McDonald, *Am J Physiol-Cell Ph* 2011, 300, C723.
[49] G. J. Brewer, *J Neurosci Res* 1995, 42, 674.
[50] S. Budday, G. Sommer, J. Haybaeck, P. Steinmann, G. A. Holzapfel, E. Kuhl, *Acta Biomaterialia* 2017, 60, 315.
[51] S. M. Chin, C. V. Synatschke, S. Liu, R. Nap, N. Sather, Q. Wang, Z. Alvarez, A. N. Edelbrock, T. Fyrner, L. C. Palmer, I. Szleifer, M. Olvera de la Cruz, S. I. Stupp, *Nat Commun* 2018, 9, 2395/1.
[52] L. M. Marquardt, V. M. Doulames, A. T. Wang, K. Dubbin, R. A. Suhar, M. J. Kratochvil, Z. A. Medress, G. W. Plant, S. C. Heilshorn, *Sci Adv* 2020, 6.
[53] U. A. Gurkan, Y. T. Fan, F. Xu, B. Erkmen, E. S. Urkac, G. Parlakgul, J. Bernstein, W. L. Xing, E. S. Boyden, U. Demirci, *Advanced Materials* 2013, 25, 1192.
[54] S. V. Murphy, P. De Coppi, A. Atala, *Nature Biomedical Engineering* 2019.
[55] J. van den Ameele, L. Tiberi, P. Vanderhaeghen, I. Espuny-Camacho, *Trends Neurosci* 2014, 37, 334.
[56] D. Lanjakornsiripan, B. J. Pior, D. Kawaguchi, S. Furutachi, T. Tahara, Y. Katsuyama, Y. Suzuki, Y. Fukazawa, Y. Gotoh, *Nat Commun* 2018, 9.

1. Synthesis 1.1. Synthesis of 6-(6-aminohexyl)amino-6-deoxy-β-cyclodextrin (CD-HDA)

CD-HDA was synthesized according to methods described previously by Loebel et al.[1] with a few minor modifications described below. β-Cyclodextrin (CD) (50 g, 44 mmol, 1 equiv) was suspended in milli-Q water (300 mL) and cooled to 0° ° C. in an ice bath. p-Toluenesulfonyl chloride (10.07 g, 53 mmol, 1.2 equiv) was dissolved in acetonitrile (25 mL). This solution was added dropwise by glass pipette to the CD suspension over 10 minutes under stirring. The reaction mixture was maintained at 0° C. for 2 hours under vigorous stirring. NaOH (5.3 g, 133 mmol, 3 equiv) was dissolved in milli-Q water (20 mL). The CD solution was removed from ice, and the NaOH solution was added dropwise by glass pipette to the CD solution under stirring. The CD solution was left at room temperature for a further 30 minutes under vigorous stirring. The pH was then adjusted by addition of solid ammonium chloride until the pH stabilized between 8.5-9 by pH paper. The solution was decanted into 50 ml conical tubes and cooled on ice. The solid was collected by centrifugation (3200 g, 2 min) and washed with water (2×40 mL), acetone (2×40 mL) and finally diethyl ether (1×40 mL) to afford the monotosylated product: 6-O-monotosyl-6-deoxy-β-cyclodextrin (CD-tos, shown in schematic 1) (12.4 g, 25%). $^1$H NMR (500 MHz, DMSO-$d_6$) δ=2.43 (s, 3H), 3.0-3.75 (m, overlap with HOD), 4.10-4.72 (m, 6H), 4.77 (s, 2H), 4.83 (m, 7H), 5.51-5.93 (br s, 14H), 7.43 (d, 2H), 7.75 (d, 2H) ppm (see section 4.1. for NMR spectra). MS (ESI): m/z: calcd. for $[C_{49}H_{76}O_{37}S]^+$: $[M+NH_4]^+$=1307.20; found: 1306.6 $[M+NH_4]^+$ Schematic 1: Structure of the 6-O-monotosyl-6-deoxy-β-cyclodextrin (CD-tos) intermediate

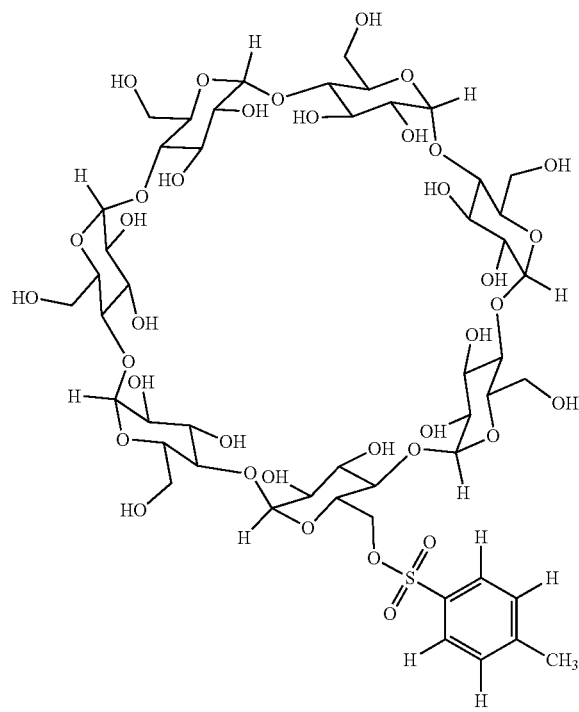

CD-tos (5.0 g, 3.9 mmol, 1 equiv) was dissolved in N,N-dimethylformamide (DMF) (25 mL) and placed under $N_2$ atmosphere. 1,6-hexanediamine (HDA) (17 mL, 172 mmol, 44 equiv) was heated to 60° C. and added via syringe to the CD-tos solution. The substitution reaction was carried out at 80° ° C. for approximately 20 hours. 5 mL of the reaction mixture was added to 50 mL conical tubes. Product was precipitated in ice cold acetone (40 mL). The product was centrifuged (3200 g, 2 min) and the supernatant decanted. The pellet was then re-dissolved in DMF (5 mL) and re-precipitated in cold acetone (40 mL). This process was repeated three times to ensure complete removal of unreacted HDA. The product was then washed in cold acetone (2×40 mL) followed by diethyl ether (2×40 mL) and dried under vacuum to afford 6-(6-aminohexyl)amino-6-deoxy-β-cyclodextrin (CD-HDA, shown in schematic 2). $^1$H NMR (500 MHz, DMSO-$d_6$) δ=1.20-1.54 (m, 12H), 3.25-3.44 (m, overlaps with HOD), 3.51-3.75 (m, 28H), 4.44 (s, 6H), 4.83 (s, 7H), 6.64-5.81 (m, 14H) ppm (see section 4.2. for NMR spectra). MS (ESI): m/z: calcd. for $[C_{48}H_{84}N_2O_{34}]^+$: $[M+2H]^+$=617.59; found: 617.31 $[M+2H]^+$ Schematic 2: Chemical structure of the 6-(6-aminohexyl)amino-6-deoxy-β-cyclodextrin (CD-HDA) product

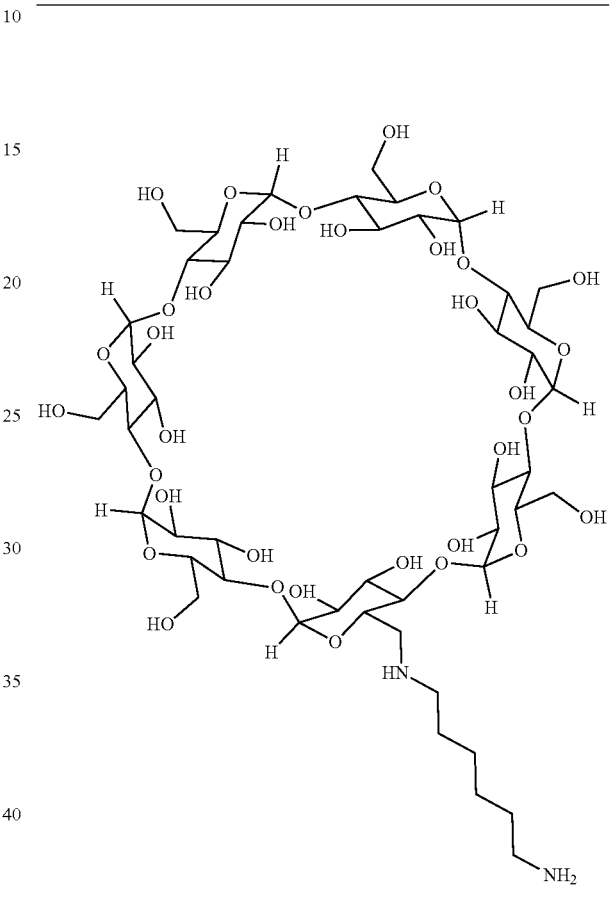

1.2. Synthesis of Peptide Amphiphiles

1.2.1. General PA Synthesis

Peptide amphiphiles (PAs) were synthesized using standard Fmoc-solid-phase peptide chemistry. PAs were synthesized on Rink amide MBHA resin (EMD) with the majority of amino acid couplings performed in a CEM Liberty Blue microwave-assisted peptide synthesizer (CEM, Matthews, NC, USA). Fmoc groups were cleaved using 20% 4-methylpiperidine and 0.1 M hydroxybenzotriazole (HOBt) in N,N-dimethylformamide (DMF) at 90° ° C. for 30 s. Amino acids were coupled using 4 molar equivalents (equiv) of protected amino acid, 8 equiv ethyl cyanohydroxyiminoacetate (Oxyma) and 4 equiv of N,N'-diisopropylcarbodiimide (DIC) and 10 equiv N,N-diisopropylethylamine (DIEA) for 2-4 min at 90° C. in 50:50 DMF:DCM as solvent. Using this same procedure, palmitic acid ($C_{16}$) was conjugated to the N-terminus of the peptide as the hydrophobic tail.

Completed PA molecules were cleaved off the resin using a solution of 95:2.5:2.5 trifluoroacetic acid (TFA)/triisopropylsilane (TIPS)/water for 2-3 h. Volatile solvents were removed with rotary evaporation, and the PAs were precipitated with cold diethyl ether and dried using a fritted filter. The PAs were then purified by preparative scale reverse phase high performance liquid chromatography (Shimadzu Prominence or Waters Prep 150), using a Phenomenex Gemini column (C-18 stationary phase, 5 μm, 100 Å pore size, either 30×150 mm or 50×250 mm). A mobile phase of acetonitrile and water was used, both containing 0.1% $NH_4OH$. Pure fractions were identified using electrospray ionization mass spectroscopy (ESI-MS) in positive or negative mode on an Agilent model 6520 Quadrupole Time-of-Flight (Q-ToF) using direct injection. MassHunter Workstation Data Acquisition software was used for instrument operation and MassHunter Qualitative Analysis software for data analysis and processing. Excess acetonitrile was removed with rotary evaporation, the samples were freeze-dried, and the powders were stored at −20° ° C. until use.

The purity of PA molecules was confirmed using liquid chromatograph-mass spectroscopy (LC-MS), which was performed using an Agilent 1200 system with a Phenomenex Gemini C-18 column (100×1.00 mm; 5 μm) for basic conditions. The mass detector (MS) was an Agilent 6520 Q-TOF MS. All gradient methods followed: acetonitrile at 5% for 5 min at 50 μL/min, 5-95% over 25 min at 50 μL/min followed by 95% for 5 min at 50 μL/min. Ammonium hydroxide (0.1% v/v) for basic conditions was added to all solvents. Peaks were detected at λ=220 nm.

1.2.2. $E_2$ PA ($E_2$ PA).

The following sequence $C_{16}V_2A_2E_2$ (schematic 3) was synthesized on Rink amide MBHA resin making use of the CEM Liberty microwave-assisted peptide synthesizer and protocols described above in section 1.21.

Schematic 3: Chemical structure of the $E_2$ PA

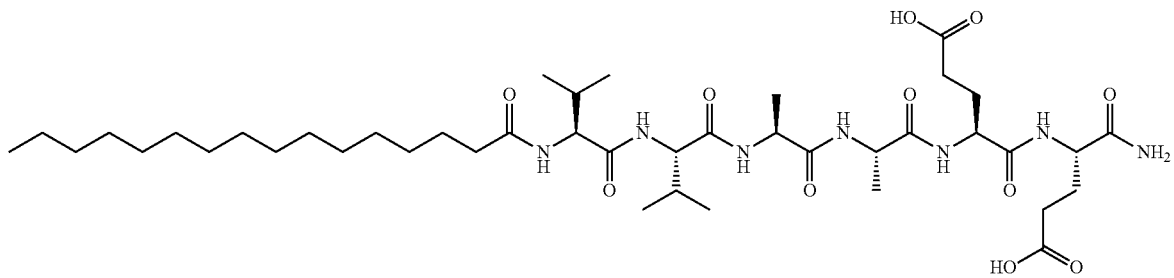

1.2.3. Dylight 405 Labeled $E_2$ PA.

The following sequence $C_{16}V_2A_2E_2C$ was synthesized on Rink amide MBHA resin making use of the CEM Liberty microwave-assisted peptide synthesizer and protocols described above in section 1.2.1. The purified PA was dissolved in tris(2-carboxyethyl)phosphine (TCEP) hydrochloride (5 equiv with respect to the PA) in pH 8 Tris buffer and reacted with maleimide-functionalized Dylight 405. The final product (schematic 4) was purified by HPLC and stored until use as described in section 1.2.1.

Schematic 4: Chemical Structure of the Dylight 405 labeled $E_2$ PA

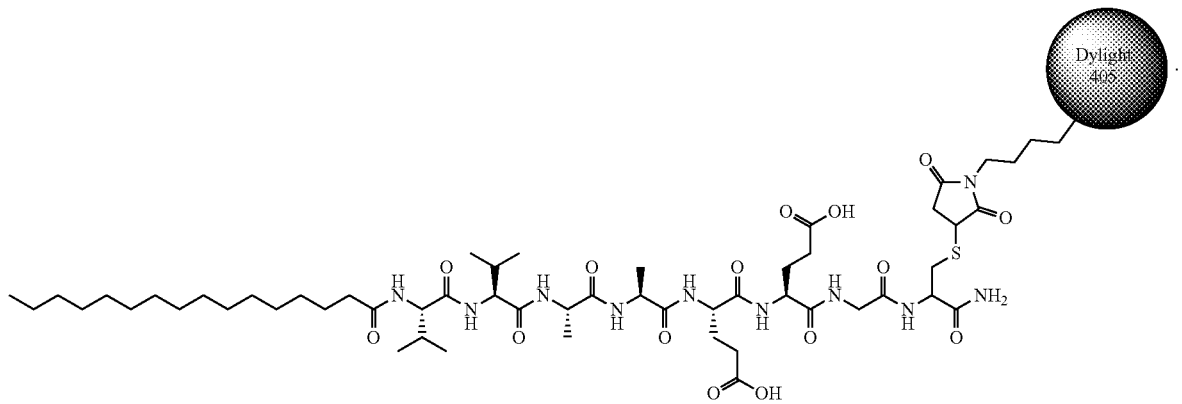

1.2.4. TAMRA Labeled $E_2$ PA.

The following sequence $C_{16}V_2A_2E_2K(Mtt)$ was synthesized on Rink amide MBHA resin making use of the CEM Liberty microwave-assisted peptide synthesizer and protocols described above in section 1.2.1. The terminal lysine ε-amine, protected with 4-methyltrityl (Mtt), was selectively deprotected on resin through the addition of a deprotection cocktail 3:5:92 TFA/TIPS/DCM, for multiple 5 min washes until yellow color was no longer seen in solution. Successful deprotection and subsequent coupling was verified through ninhydrin colorimetric assay (Kaiser test). Carboxytetramethyl rhodamine (TAMRA) (2 equiv) was coupled to the free ε-amine with 2 equiv TAMRA, 2 equiv PyBOP and 6 equiv DIEA in DMF for 16 h on a mechanical peptide shaker. Following successful coupling, the PA was cleaved, purified and stored as described in section 1.2.1. The TAMRA labeled PA is shown in schematic 5.

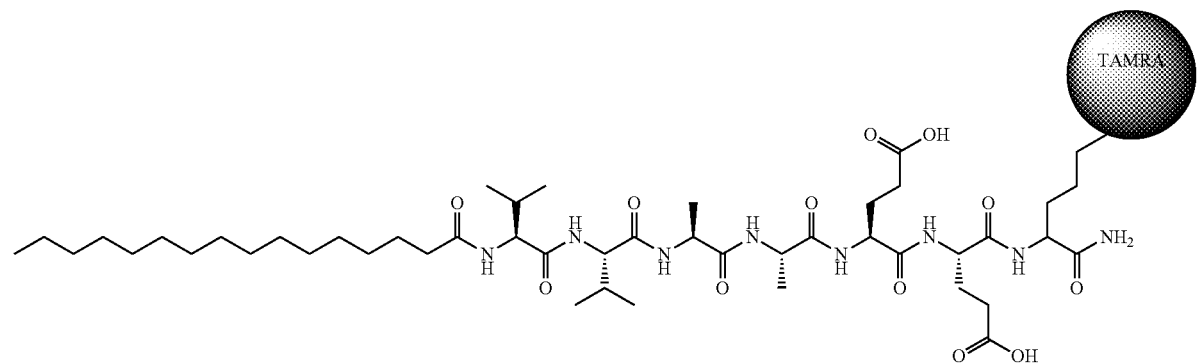

Schematic 5: Chemical structure of the TAMRA labeled $E_2$ PA

1.2.5. Alexa Fluor® 488 Labeled $E_2$ PA.

The following sequence $C_{16}V_2A_2E_2C$ was synthesized on Rink amide MBHA resin using the CEM Liberty microwave-assisted peptide synthesizer and protocols described above in section 1.21. The purified PA was dissolved in tris(2-carboxyethyl)phosphine (TCEP) hydrochloride (5 equiv with respect to the PA) in pH 8 Tris buffer and reacted with maleimide functionalized Alexa Fluor® 488. The final product was purified by HPLC and stored until use as described in section 1.2.1. The Alexa Fluor®488 Labeled PA is shown in schematic 6.

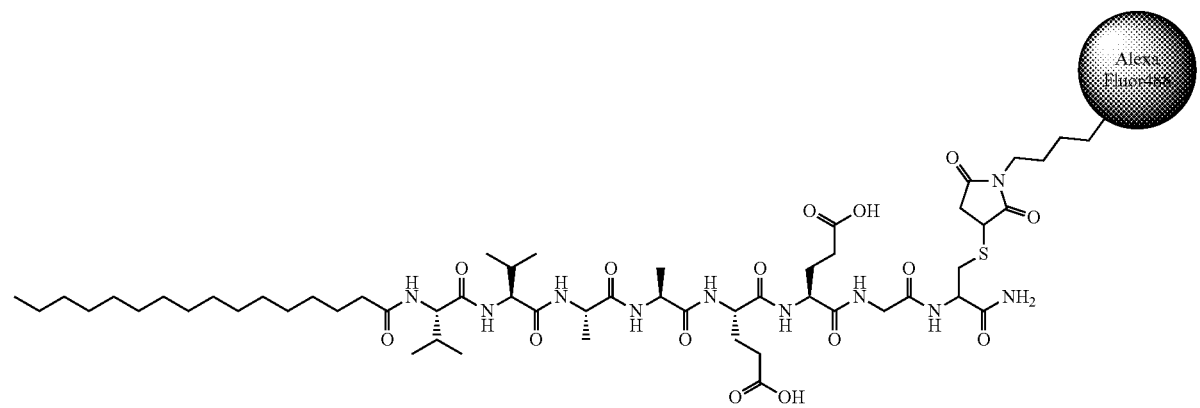

Schematic 6: Chemical structure of the Alexa Fluor® 488 labeled $E_2$ PA

1.2.6. Adamantane PA (Ada PA).

The following sequence $C_{16}V_2A_2E_4G_6K(Mtt)$ was synthesized on Rink amide MBHA resin making use of the CEM Liberty microwave-assisted peptide synthesizer and protocols described above in section 1.2.1. The terminal lysine ε-amine, protected with 4-methyltrityl (Mtt), was selectively deprotected through the addition of a deprotection cocktail 3:5:92 TFA/TIPS/DCM, for multiple 5 min washes until yellow color was no longer seen in solution. Successful deprotection and subsequent coupling was verified through ninhydrin colorimetric assay (Kaiser test). 1-Adamantanecarboxylic acid was coupled to the free ε-amine with 4 equiv 1-adamantanecarboxylic acid, 2 equiv PyBOP and 6 equiv DIEA in DMF for 4 h on a mechanical peptide shaker. Following successful coupling, the PA was cleaved, purified and stored as described in section 1.2.1. The structure of Ada PA is shown in schematic 7.

Schematic 7: Chemical structure of the Adamantane PA (Ada PA)

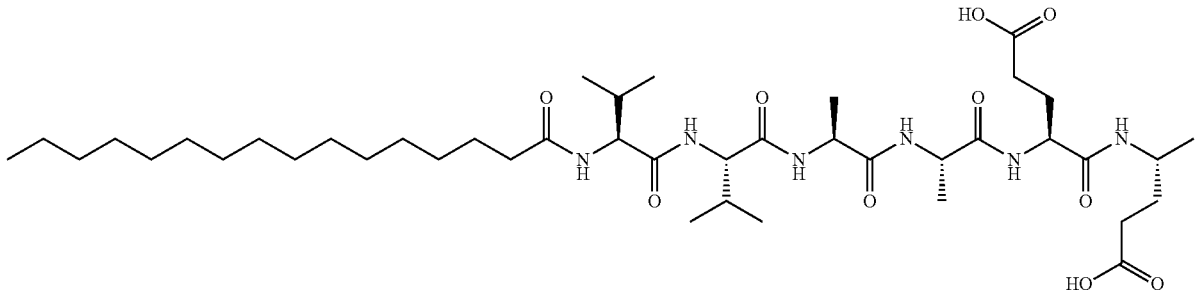

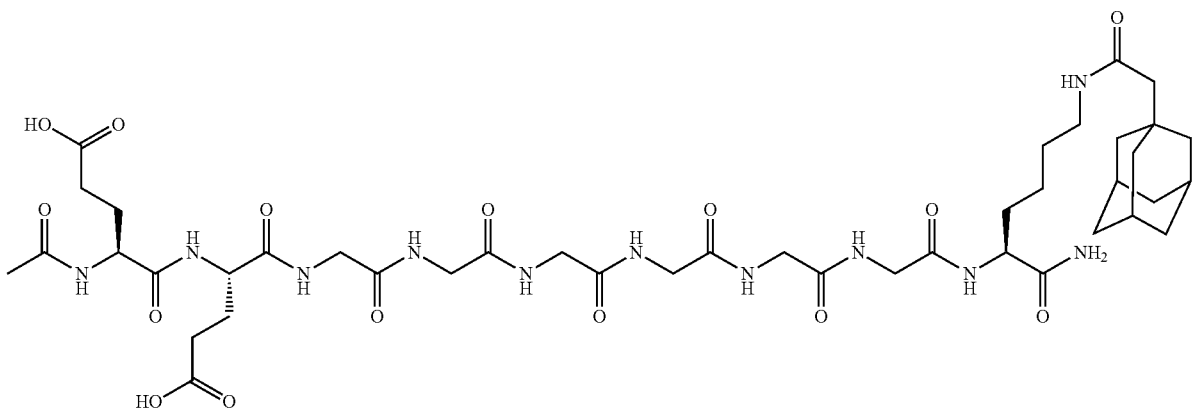

1.2.7. Cy3 Labeled Ada PA.

The following sequence $C_{16}V_2A_2E_4G_6K(Az)K(Mtt)$ (Mtt=4-methyltrityl) was synthesized on Rink amide MBHA resin making use of the CEM Liberty microwave-assisted peptide synthesizer and protocols described above in section 1.2.1. The Mtt group on the terminal lysine ε-amine was selectively cleaved by the addition of a deprotection cocktail of 3:5:92 TFA/TIPS/DCM, for multiple 5 min washes until yellow color was no longer seen in solution. Successful deprotection and subsequent coupling was verified through ninhydrin colorimetric assay (Kaiser test). 1-Adamantanecarboxylic acid (4 equiv) was coupled to the free ε-amine with 2 equiv PyBOP and 6 equiv DIEA in DMF for 4 h on a mechanical peptide shaker. Following successful coupling, the PA was cleaved, purified and stored as described in section 1.2.1. DBCO-Cy3 was coupled to the purified PA through the azido lysine (K(Az)) (1.5 equiv) in DMF, at room temperature, protected from light overnight. Upon completion of the click reaction, the final product (schematic 8) was purified by HPLC and stored until use as described in section 1.2.1.

1.2.8. Cyclodextrin PA (CD PA).

The following sequence $C_{16}V_2A_2E_4PEG_{10}K(Mtt)$ was synthesized on Rink amide MBHA resin making use of the CEM Liberty microwave-assisted peptide synthesizer and protocols described above in section 1.2.1. The Mtt group on the terminal lysine ε-amine was selectively cleaved by the addition of a deprotection cocktail of 3:5:92 TFA: TIPS: DCM, for multiple 5 min washes until yellow color was no longer seen in solution. Successful deprotection and verified through ninhydrin colorimetric assay (Kaiser test). Diglycolic acid was coupled to the free ε-amine with 4 equiv diglycolic acid, 2 equiv PyBOP and 6 equiv DIEA in 50:50 DMF/DCM for 4 h on an automatic peptide shaker. Successful coupling was confirmed via by Kaiser Test. Following successful coupling, the resin was washed three times with DMF and 2 equiv PyBOP and 6 equiv DIEA in DMF was added to the resin for 5 min shaking. CD-HDA (synthesized as per protocol in section 1.1) was dissolved in DMF (2 eq) and added to the activated PA solution and left to react on an automatic peptide shaker overnight. This coupling was repeated a second time to improve yield of the CD PA. Successful coupling was confirmed via ESI-MS before being cleaved, purified and stored as described in section 1.2.1.

Schematic 8: Chemical structure of the Cy3 labeled Ada Pa

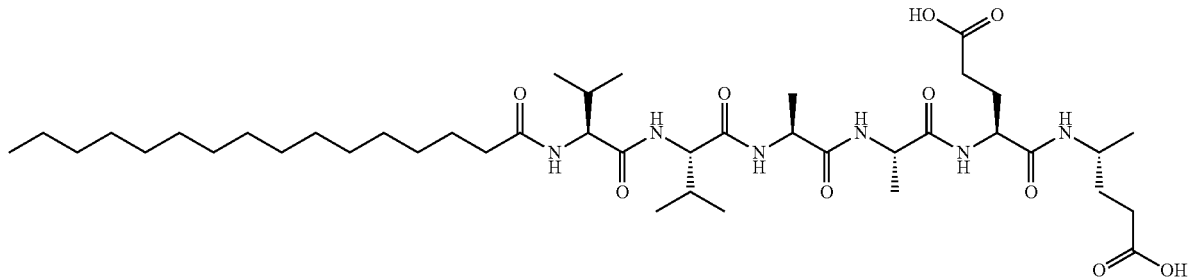

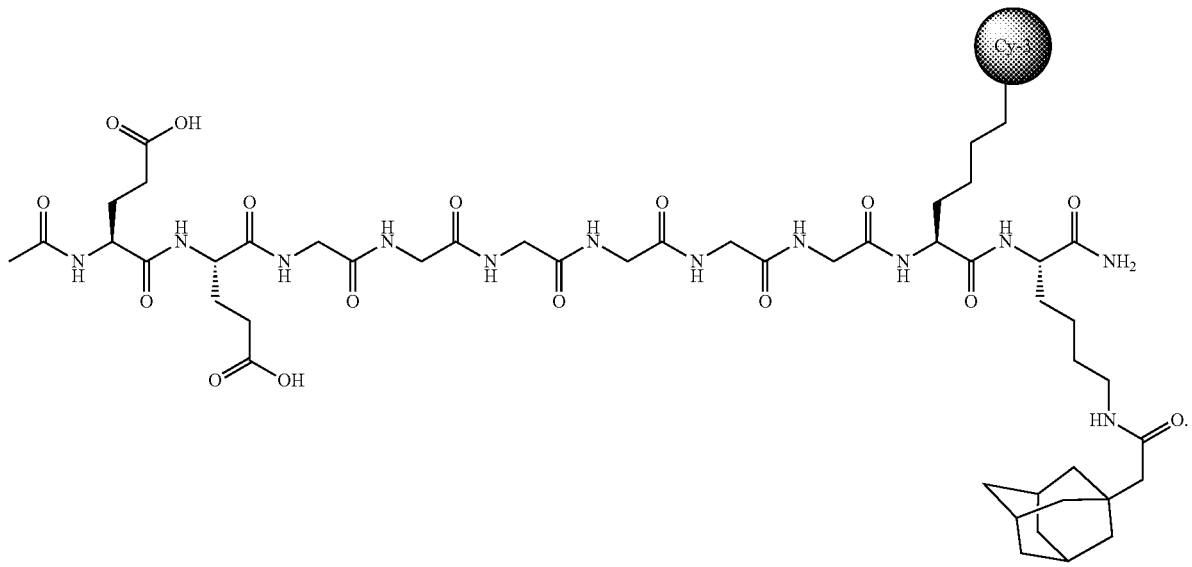

MS (ESI): m/z: calcd. for $[C_{135}H_{235}N_{15}O_{67}]^+$: $[M+NH_4]^+$ = 3156.57; found: 3156.69 $[M+NH_4+]^+$ Schematic 9: Chemical structure of the Cyclodextrin PA (CD PA)

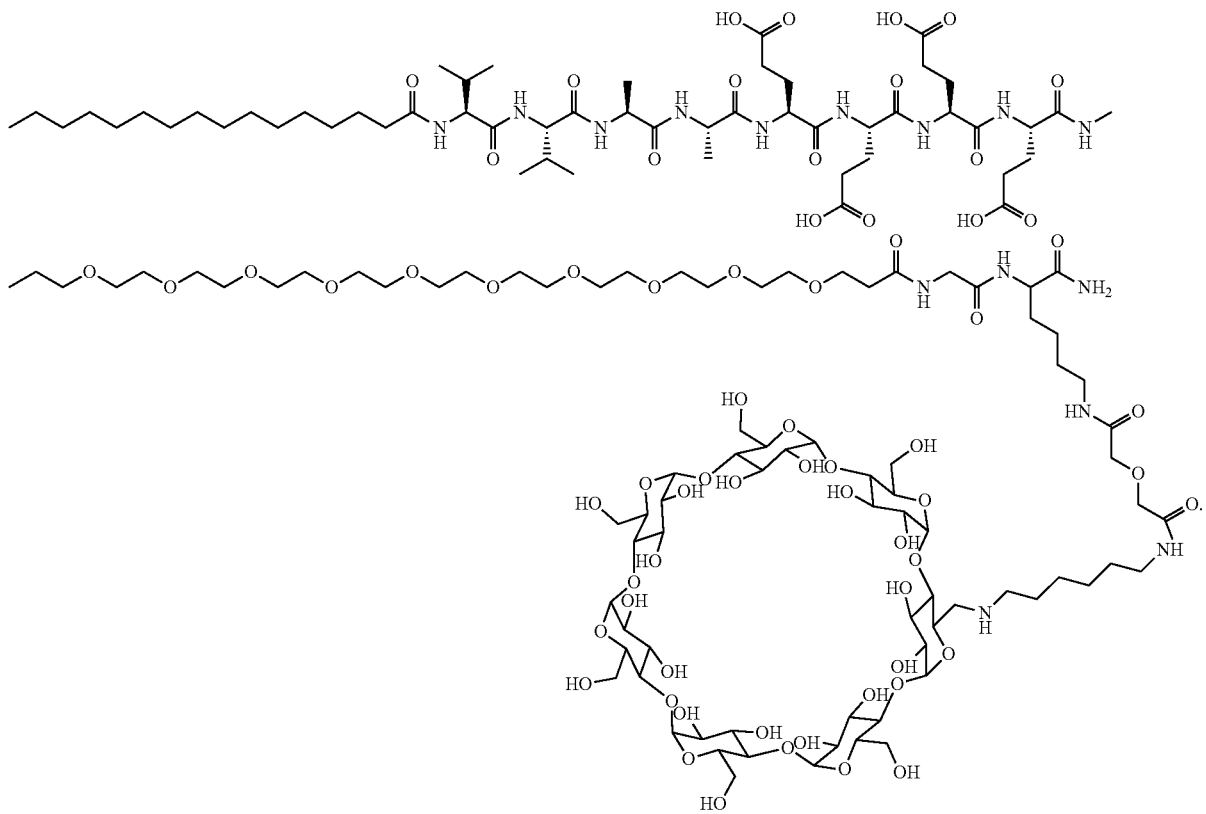

1.2.9. Cy5 Labeled CD PA.

The following sequence $C_{16}V_2A_2E_4PEG_{10}K(Az)K(Mtt)$ was synthesized on Rink amide MBHA resin making use of the CEM Liberty microwave-assisted peptide synthesizer and protocols described above in section 1.2.1. The Mtt group on the terminal lysine ε-amine was selectively cleaved by the addition of a deprotection cocktail of 3:5:92 TFA/TIPS/DCM, for multiple 5 min washes until yellow color was no longer seen in solution. Successful deprotection and subsequent coupling was verified through ninhydrin colorimetric assay (Kaiser test). Diglycolic acid was coupled to the free ε-amine with 4 equiv diglycolic acid, 2 equiv PyBOP and 6 equiv DIEA in 50:50 DMF/DCM for 4 h on an automatic peptide shaker. Following successful coupling, the resin was washed 3× with DMF and 2 equiv PyBOP and 6 equiv DIEA in DMF was added to the resin for 5 min shaking. HDA-CD (synthesized as per protocol in section 1.1) (2 equiv) was dissolved in DMF and added to the activated PA solution and left to react on an automatic peptide shaker overnight. This coupling was repeated a second time to improve yield of the CD PA before being cleaved, purified and stored as described in section 1.2.1. DBCO-Cy5 was coupled to the purified PA through the azido lysine (K(Az)) (1.5 equiv) in DMF, at room temperature, protected from light overnight. Upon completion of the click reaction, the final product was purified by HPLC and stored until use as described in section 1.2.1.

Schematic 10: Chemical structure of the Cy5 labeled CD PA

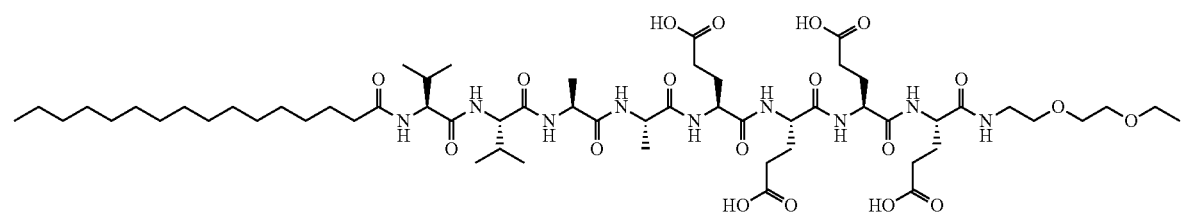

-continued

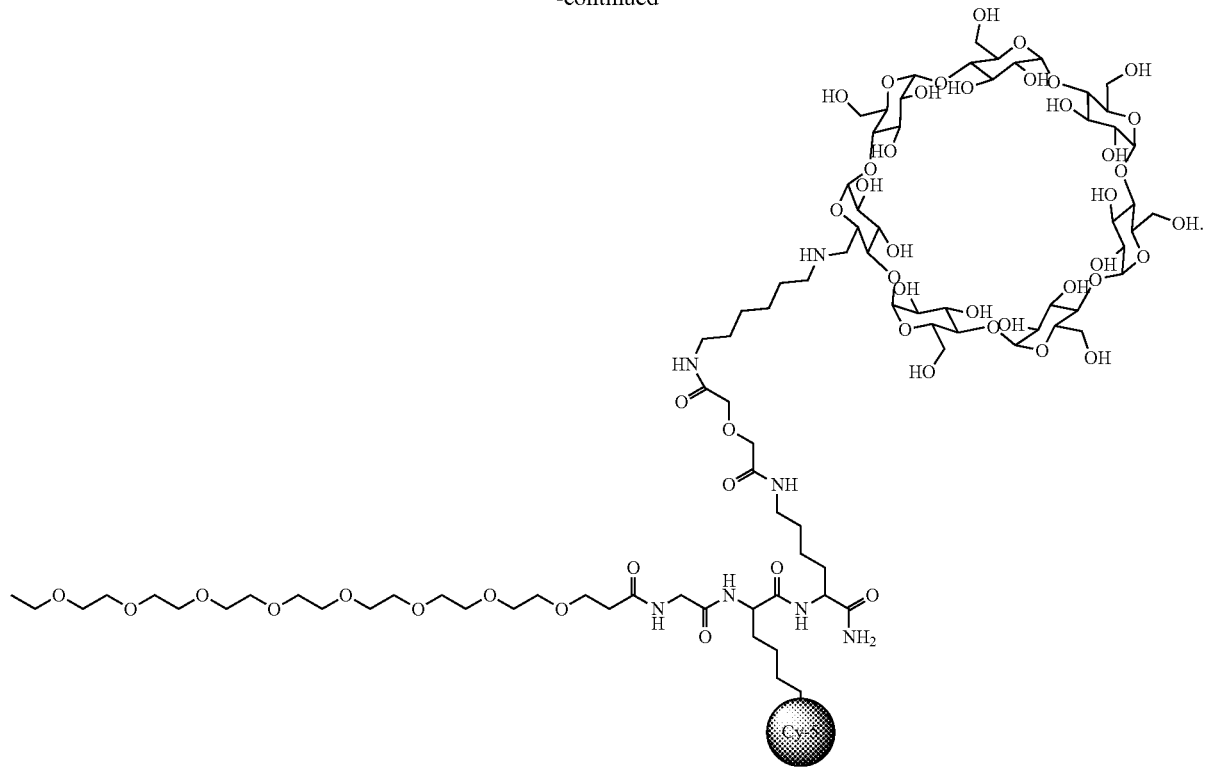

2. Materials and Methods

2.1. Material Preparation.
2.1.1. Peptide Amphiphile Preparation.

All PAs were taken from their powder form after lyophilization and dissolved in 125 mM NaCl and 3 mM KCl solution at a concentration of 1, 2, or 3 mg/100 μL. The resulting PA solution was then adjusted to a pH of 7.4 using 1 μL additions of 1 M NaOH. Once the pH was adjusted, Ada PA, CD PA, and the BDNF PA were co-assembled at 10 mol % concentrations with $C_{16}$-$V_2A_2E_2$ PA ($E_2$). The BDNF superstructure was made by co-assembling the CD PA or Ada PA at 10 mol % with the BDNF PA at 10 mol % and $E_2$ at 80 mol %. The CD-$E_2$ PA+BDNF PA and Ada-$E_2$ PA+BDNF PA were then mixed 1:1 for experiments. Similarly, the dye-labeled PAS were co-assembled with their respective non-labeled counterparts at 2 mol % of dye-labeled PA, 8 mol % CD-$E_2$ PA or Ada-$E_2$ PA, and 90% $E_2$ PA. After mixing, the solutions were heated with a polymerase chain reaction (PCR) thermocycler (Eppendorf) and annealed at 80° C. for 30 min, then slowly cooled at 1° C. per minute back down to 27° C.

2.1.2. Peptide Amphiphile 3D Gel Preparation.

Materials were prepared using annealed PAs previously described in section 2.1.1. To form superstructure gels, solutions of cyclodextrin and adamantane PAs were mixed together in the same Eppendorf using vigorous pipetting. Silicon isolators with adhesive (Invitrogen) were placed on coverslips coated with PDL and 100 μL of PA material was added to the circular well following previously published methods.[2] A porous membrane was placed on top of the well and a solution of 125 mM NaCl, 3 mM KCl and 25 mM $CaCl_2$) was added to each PA condition to ensure even swelling of all gels. Serum-containing media was then added to equilibrate the materials for cell-culture purposes.

2.1.3. Preparation of Free Adamantane Solution.

A 300 mM stock solution of 1-adamantaneacetic acid ("free adamantane") was prepared in dimethyl sulfoxide (DMSO). The stock solution was then diluted in 125 mM NaCl and 3 mM KCl solution to prepare a 1 mM and 2 mM free adamantane working solution used in rheological and confocal measurements. It was added in 0.5, 1, or 2 equivalents relative to the CD PA.

2.1.4. Preparation of 3D Printing Inks.

The $E_2$ PA print (FIG. 4c) consisted of three different inks. The $E_2$ PA was co-assembled at 1 mol % with $E_2$ PA that had been functionalized with either Alexa 488 (Green) or TAMRA dye label (Red). The third ink consisted of $E_2$ mixed with a DAPI stain (Blue, 1:100 by volume dilution of DAPI into the material). For the superstructure layered print (FIG. 4d), superstructure materials were prepared by mixing the CD PA and Ada PA at a 1:1 ratio and the different dye-labeled materials were incorporated at 1 mol % to obtain different layers. The four superstructure inks consisted of 1) the superstructure PA material with a Cy3 labeled Ada PA (Red), 2) a Cy5 labeled CD PA (Green), 3) both the Cy3 and Cy5 labeled materials (Yellow), and 4) a layer with DAPI stain mixed into the (Blue, 1:100 by volume dilution of DAPI into material).

2.2. Material Characterization.
2.2.1. Cryogenic-Transmission Electron Microscopy (Cryo-TEM).

300-mesh copper grids with lacey carbon film (Electron Microscopy Sciences, Hatfield, PA, USA) were glow discharged for 20 seconds in a PELCO easiGlow system (Ted Pella, Inc., Redding, CA, USA) prior to use. Samples at 1 w/v % were tenfold diluted to 0.1 w/v % immediately before blotting. 7 μL of sample solutions were transferred to the plasma-cleaned 300-mesh copper grids with lacey carbon support and plunge-frozen using a Vitrobot Mark IV (FEI) vitrification robot. Samples were blotted at room temperature (RT) with 95-100% humidity and plunge frozen into liquid ethane. Samples were transferred into a liquid nitrogen bath and placed into a Gatan 626 cryo-holder through a cryo-transfer stage. Cryo-TEM was performed using a liquid nitrogen cooled JEOL 1230 TEM working at 100 kV accelerating voltage. Images were acquired using a Gatan 831 CCD camera.

2.2.2. Fiber Width Analysis.

Using micrographs obtained from the Cryo-TEM imaging, the widths of at least 250 random fibers were measured by hand. Representative Cryo-TEM images used for the analyses are shown in FIG. 6. Measurements were taken using the line tool in combination with the measuring feature in FIJI ImageJ analysis software.

2.2.3. Dynamic Light Scattering (DLS).

The Malvern Zetasizer Nano ZSP light scattering spectrometer was used for DLS measurements. Annealed PA samples were prepared as described in section 2.1.1. at 1 wt %. The sample was kept at a temperature of 25° C. and equilibrated for 30 seconds before each measurement which lasted 10 seconds each. The measurement angle was 173° backscatter and the attenuator and accumulation were automatically determined by the instrument for each run. Each measurement was repeated a total of three times.

2.2.4. Circular Dichroism (CD).

Samples were prepared as previously described in section 2.1.1. Each sample was diluted to concentrations between 0.01-0.04 wt % in milli-Q water. CD spectra were recorded on a JASCO model J-815 spectropolarimeter using a quartz cell of 0.5 mm optical path length. Continuous scanning mode was used with a scanning speed of 100 nm per minute with the sensitivity set to standard mode. High Tension (HT) voltage was recorded for each sample to ensure that the measurement was not saturated. An accumulation of three measurements was used and a buffer sample was background-subtracted to obtain final spectra. The final spectra were normalized to final concentration of each sample using a molar averaged molecular weight.

2.2.5 Fourier-transform infrared (FTIR) Spectroscopy

Samples were prepared as previously described in section 2.1.1, lyophilized and re-dissolved in $D_2O$ to a final PA concentration of 10 mM. The liquid samples were sandwiched between two $CaF_2$ windows using a spacer of 50 µm in an FTIR liquid flow cell (Pike Technologies). Infrared (IR) spectra were recorded on a Bruker model Tensor 37 spectrometer.

2.2.6. Determination of Association Constants by NMR Titrations.

The association constant for the binding between 1-adamantaneacetic acid and β-cyclodextrin was measured in 125 mM NaCl and 3 mM KCl buffer at pH 7.2-7.4. In a typical titration experiment, small amounts of a "guest solution" (100 mM 1-adamantaneacetic acid and 3.5 mM β-cyclodextrin in deuterated buffer) were added to approximately 0.8 ml of "host solution" (3.5 mM β-cyclodextrin in deuterated buffer) until at least 5 equiv of "guest" molecules were added. 1H-NMR spectra were obtained at 25° C. upon each addition of the "guest" solution and a binding isotherm was constructed by monitoring the protons on 1-adamantaneacetic acid.

The association constant for the binding between CD-$E_2$ PA and 1-adamantaneacetic acid was measured in 125 mM NaCl and 2 mM KCl buffer at pH 7.2-7.4. The "host solution" containing the CD-$E_2$ PA was prepared by mixing 1 wt % solutions of CD PA and $E_2$ PA in deuterated buffer such that the final solution would contain 80 mol % $E_2$ PA and 20 mol % CD PA (i.e. 1.4 mM CD-$E_2$ PA). The "host solution" was then annealed in a water bath at 80° C. for 30 min, then slowly cooled to RT over 18 h. The "guest solution" was prepared by dissolving 1-adamantaneacetic acid in a portion of the "host solution" to obtain a solution containing 65 mM 1-adamantaneacetic acid and 1.4 mM CD-$E_2$ PA in deuterated buffer. In a typical titration experiment, small amounts of the "guest solution" were added to approximately 0.5 ml of "host solution" until at least 5 equiv of "guest" molecules were added. 1H-NMR spectra were obtained at 25° C. upon each addition of the "guest solution" and a binding isotherm was constructed by monitoring the protons on 1-adamantaneacetic acid.

The association constant for the binding between Ada-$E_2$ PA and β-cyclodextrin was measured in 125 mM NaCl and 2 mM KCl buffer at pH 7.2-7.4. The "host solution" containing the Ada-$E_2$ PA was prepared by mixing 1 wt % solutions of Ada PA and $E_2$ PA in deuterated buffer such that the final solution would contain 80 mol % $E_2$ PA and 20 mol % of Ada PA (i.e. 2 mM Ada-$E_2$ PA). The "host solution" was then annealed in a water bath at 80°C for 30 min, then slowly cooled to RT over 18 h. The "guest solution" was prepared by dissolving 1-adamantaneacetic acid in a portion of the "host solution" to obtain a solution containing 35 mM β-cyclodextrin and 2 mM Ada-$E_2$ PA in deuterated buffer. In a typical titration experiment, small amounts of the "guest solution" were added to approximately 0.5 ml of "host solution" until at least 5 equiv of "guest" molecules were added. $^1$H-NMR spectra were obtained at 25° C. upon each addition of the "guest solution" and a binding isotherm was constructed by monitoring the protons on β-cyclodextrin.

The binding isotherms were fit to a standard 1:1 host-guest binding model (Eq. 1-3) where [HG] is the concentration of host-guest complex, $[H]_0$ is the total concentration of "host" molecules, $[G]_0$ is the total concentration of "guest" molecules, do is the proton peak position at $[HG]/[H]_0=0$, δ is the proton peak position measured at different values of $[HG]/[H]_0$, and $\delta_\infty$ is a fitting parameter. All spectra were obtained with a X500 Bruker Avance III HD system equipped with a TXO Prodigy probe and analyzed with the MestreNova (Mestrelab Research) software.

$$[HG] = \frac{1}{2}\left\{\left([G]_0 + [H]_0 + \frac{1}{K_a}\right) - \sqrt{\left([G]_0 + [H]_0 + \frac{1}{K_a}\right)^2 - 4[H]_0[G]_0}\right\} \quad 1$$

$$\delta = \delta_\infty\left(\frac{[HG]}{[H]_0}\right) + \delta_o \quad 2$$

$$\Delta\delta = \delta - \delta_o \quad 3$$

2.2.7. Small Angle X-Ray Scattering (SAXS)/Multi-Angle X-Ray Scattering (MAXS)/Wide Angle X-Ray Scattering (WAXS).

Experiments were performed at beamline 5-ID-D of the DuPont-Northwestern-Dow Collaborative Access Team (DND-CAT) Synchrotron Research Center at the Advanced Photon Source, Argonne National Laboratory. PA samples were prepared at 2 w/v % irradiated for 2 or 10 seconds. Data was collected with an X-Ray energy at 17 keV (1=0.83 Å). Sample to detector distances were as follows: 201.25 mm for SAXS, 1014.2 mm for MAXS, and 8508.4 mm for WAXS. The scattering intensity was recorded in the interval 0.002390<q<4.4578 Å$^{-1}$. The wave vector q is defined as =(4π/λ) sin(θ/2), where θ is the scattering angle. Azimuthal integration (Fit2D) was used to average 2D scattering images to produce 1D profiles of intensity versus q. Samples were oscillated with a syringe pump during exposure to prevent beam damage. Background scattering patterns were obtained from samples containing 125 mM NaCl and 3 mM KCl. This background data was then subtracted from experimental data. All data was analyzed using the Irena software package running on IgorPro software.

2.2.8. Scanning Electron Microscopy (SEM).

All materials were gelled with 125 mM NaCl, 3 mM KCl and 25 mM $CaCl_2$ to ensure that all materials, even weaker controls, could be processed for SEM. These PA gels were fixed in a 2.5% glutaraldehyde (GTA) 4% paraformaldehyde (PFA) phosphate buffered saline (PBS) solution for 20 minutes. They were dehydrated in a series of ethanol solutions increasing in concentration from 30-100%. Ethanol was then removed with critical point drying using a Tousimis Samdri-795. Dehydrated samples were mounted on stubs using carbon glue and then coated with 16 nm of osmium (Filgen, OPC-60A) to create a conductive surface. Images were taken using a Hitachi SU8030 instrument using an accelerating voltage of 2 kV.

2.2.9. Rheological Measurements.

PA materials were prepared and annealed using methods described in section 2.1.1. An Anton Paar MCR302 Rheometer with a 25 mm cone plate was used for all rheological studies. 150 μL of PA liquid was placed on the sample stage. For experiments using Free Adamantane, 30 μL of either 1 mM or 2 mM adamantane solution (prepared as described in section 2.1.3) was added in droplets to the top plunger. The plunger was then lowered to the measuring position and a humidity collar was added during the "sample trim" phase to prevent sample evaporation during the measurement. The sample was equilibrated for 30 minutes with a constant angular frequency of 10 rad/s and 0.1% strain. The storage and loss modulus were recorded. For thixotropy studies, the sample was applied to the stage as previously mentioned. The first and third interval consisted of 10, 6 second points with an oscillating shear strain of 0.1% and angular frequency of 10 rad/s. The storage and loss modulus were plotted against time. The second interval consisted of 10, 1 second points with a constant shear rate of 100 $s^{-1}$. The viscosity was plotted against time. For recovery experiments, G' and G" were measured during alternating intervals of low and high strain. The low strain interval was 200 seconds at 0.5% strain and the high strain interval was 50 seconds at 50% strain.

2.2.10. Confocal Imaging of Peptide Amphiphile Materials.

Dye-labeled PAs were prepared as previously described in section 2.1.1. 50 μL of CD-$E_2$ PA and Ada-$E_2$ PA labeled with fluorophores were mixed 1:1 directly before imaging. To image, a 10 μL droplet of each PA sample was placed on the bottom of a 35 mm glass petri dish (MatTek). Images were immediately taken using the Nikon A1R confocal microscope. Every ten minutes of imaging, a new droplet was placed to avoid drying effects. Z-stacks were made for each sample and processed using FIJI by ImageJ. For the unbundling experiments, 0.5 or 1 equivalent of free adamantane solution (prepared as described in section 2.1.3.) was added to the superstructure PA material and immediately imaged.

2.2.11. Co-localization Analysis.

Pearson's correlation coefficient analysis was performed on single slices of confocal Z-stacks collected on the dye labeled PAs. Analysis was performed in FiJi making use of the JaCOP plugin.[3] For this analysis, single focal plane slices from the confocal superstructure Z-stacks were isolated and the fluorescent channels from the corresponding PAs separated into individual images for pixel colocalization analysis. 10 separate Z-stack images of the superstructure PA assembly were analyzed, with 3 different focal planes taken from the central region of each stack. Results are displayed as means±SD. Data was analyzed using the GraphPad Prism version 6.0 data management software to conduct ANOVA on groups of data. Statistically significant differences between each comparison were determined using Turkey's post hoc test ($*p<0.05$, $p<0.01$, $*p<0.001$).

2.3. In Vitro Studies.

2.3.1. Dissection of Embryonic Primary Cortical Neurons.

All neurons used were obtained by dissecting embryonic brains following procedures described previously.[4] Timed-pregnant mice were anesthetized using isoflurane and sacrificed by cervical dislocation. The embryos were extracted at embryonic day 16 (E16). The cerebral cortices were extracted from the mouse embryos and the meninges were removed. The tissue was kept in a cold sterile solution of Hank's Balanced Salt Solution (HBSS) with 1% pen-strep (Invitrogen). The tissue was then digested using trypsin (Invitrogen) and DNAse I (Sigma-Aldrich) for 10 min at 37° C. The cortices were broken up by pipetting up and down, centrifuged at 1000 g for 5 min, and resuspended in $CO_2$-equilibrated Neurobasal (NB, Invitrogen) neuronal culture medium with 10% normal horse serum (NHS, Invitrogen), 1% penicillin-streptomycin (pen-strep, Invitrogen), 0.5 mM L-glutamine (Invitrogen), and 5.8 μL/mL $NaHCO_3$(Sigma-Aldrich). After centrifugation, the cells pellet was resuspended and pre-plated at 37° C. for 30 min. The supernatant was collected and passed through a cell strainer with 100 μm pores. The resulting solution was centrifuged at 1000 g for 5 min. This pellet was resuspended in NB culture medium (1% NHS, 1% pen-strep, 0.5 mM L-glutamine, 22 μM glutamic acid (Sigma-Aldrich), 2% B27 (Gibco), and 5.8 μL/mL $NaHCO_3$(Sigma-Aldrich)), and plated at different densities (depending on the type of experiment, see below). Tissue culture plastic or glass coverslips used in experiments with these cells were coated with poly-D-lysine (PDL, Sigma-Aldrich). After 24 h, the medium was replaced with serum-free neuronal culture medium (1% pen-strep, 0.5 mM L-glutamine, 2% B27, 5.8 μL/mL $NaHCO_3$). These conditions promoted a neuron-rich culture containing approximately 10% glial cells.

2.3.2. Dissection of Primary Astrocytes.

Glial cells were dissected from the cerebral cortex of newborn mice (postnatal day 0, P0), as described elsewhere.[5] In dissection buffer of HBSS with 1% pen-strep (Invitrogen), the meninges were removed, and the cortexes were separated out. This tissue was then digested using trypsin and DNAse I for 10 min at 37° C. Dissociation of the tissue was carried out in Dulbecco's Modified Eagle Medium (DMEM, GIBCO), 10% NHS, 1% pen-strep, and 2 mM L-glutamine. Cells were centrifuged at 1000 g for 5 min, supernatant was removed, and cells were resuspended. Cells were then plated and grown to confluence at 37 C, 5% $CO_2$ for approximately 25-30 days in vitro. All experiments were performed using glial cells from the first through third passages (Ps1-Ps3). Cells were cultured at a density of 1 or 2 million cells per 100 μL of PA ink used for 3D printing.

2.3.3. PA Treatments and Cell Culture Procedures.

Treatments were prepared by dissolving PA (BDNF PA, superstructure PA, or BDNF superstructure) in media without serum or B27 supplement. The total concentration of BDNF PA in each condition was 10 μM and the total concentration of PA was 100 μM. Human/Murine/Rat BDNF protein (Peprotech) was resuspended at 0.25 nM in starvation media as a positive control. For Western blot experiments, primary cortical neurons were cultured in 6 well plates at a density of approximately 900,000 cells/well for 7 days in vitro (DIV) before being treated. Treatments were added for 24 h in vitro before protein was harvested. For infiltration and gel viability studies, 300,000 primary neurons per well were seeded on gels in a 24 well plate and cultured for 7 DIV. Samples were fixed in 4% PFA for 20 min at RT for immunofluorescence studies. For 3D printing experiments, primary astrocytes were seeded at 1 or 2 million cells/100 µL of PA. Primary neurons were seeded at 4 million cells/100 µL of PA. Prints were cultured for 7 or 14 DIV. Samples were fixed in 4% PFA for 20 min at RT.

2.4. Biological Assays.

2.4.1. Western Blot.

Halt Protease and Phosphatase Inhibitor Cocktail (Thermo Scientific) was used to extract protein from primary neuronal cultures. Samples were stored at −20° C. and a BCA assay (Thermo Scientific) was performed to determine protein content for each collected sample. Protein was then diluted with $H_2O$ to ensure the same concentration for each condition. Samples were loaded into a 4-20% SDS-PAGE gel (Bio-Rad) and separated for 1.5 h using a power source set to 115 volts. The protein was electro-transferred from the SDS-PAGE gel to a nitrocellulose membrane (Bio-Rad). The membrane was checked for protein content using ponceau stain (Sigma-Aldrich). Once protein content was determined to be present, the membrane was blocked for 30 minutes using a 5% milk solution (Bio-Rad). The membrane was then incubated over night with primary antibodies. The following primary antibodies were used: rabbit anti-pTrkB (1:1000, Cell Signaling), rabbit anti-TrkB (1:1000, Cell Signaling), rabbit anti-Actin (1:2000, Sigma-Aldrich), mouse anti-Actin (1:2000, Sigma-Aldrich). Corresponding secondary HRP-conjugated antibodies (1:1000, ThermoFisher) were incubated at RT for 2 h. Radiance Bioluminescent ECL substrate (Azure Biosystems) was used to detect protein signals. The membranes were imaged using the Azure Biosystems imager on the automatic setting. Densitometry analysis, was performed using ImageJ software and was standardized to total receptor or actin content as a control for protein loading.[6] Triplicate samples were analyzed from at least two separate experiments.

2.4.2. Immunofluorescence.

Fixed samples (4% PFA for 20 min at RT) were incubated with primary antibodies over night at 4° C. Alexa 488 and Alexa 555 antibodies at a dilution of 1:2000 (Invitrogen) were incubated for 2 h at RT. The following primary antibodies were used: rabbit anti-MAP-2 (marker for mature neurons 1:2000, BioLegend). DAPI was used to stain the nuclei (nuclear stain, 1:2000, Invitrogen).

2.4.3. Imaging.

A Nikon AIR confocal laser-scanning microscope with GaAsP detectors was used to visualize and image fluorescent 3D samples. Resulting images were processed and converted to TIF files using a plugin through FIJI an ImageJ software (National Institutes of Health). Confocal z-stack reconstructions were compiled using NIS Elements Advanced Research Microscope Imaging software (version 4.20) or Imaris program (version 9.3.1, Bitplane Scientific software) for 3D interactive data viewing. Large fluorescent images of 3D printed PA gels were taken using a Nikon Ti2 Widefield Microscope. For visualization purposes, benchtop images of experiments visible to the human eye were taken using an Apple iphone 6s. The images were placed in Adobe Photoshop (v.20.0.6) and adjustments for contrast, brightness and color balance were made to obtain optimal and consistent visual reproduction of the data.

2.4.4. Cell Viability.

Cell culture medium was removed, and the gels were rinsed once with HBSS. A calcein-AM/propidium iodide live/dead assay (Invitrogen) was used to check cell viability of cells seeded on top of or within 3D printed PA gel scaffolds. Calcein-AM (16 µM)/propidium iodide (20 µM) solution in HBSS was added to each well. The plate was covered with foil and left at RT for 15 min. The solution was removed, and the samples were rinsed with HBSS and the samples were immediately imaged using confocal microscopy.

2.4.5. Infiltration Study and Analysis of PA Gels.

PA materials were prepared as described in section 2.1.1. 3D Gels were prepared as described in section 2.1.2. to mimic the molded scaffold setup used in vitro. They were rinsed once with media and cells were seeded at 300,000 cells/well. Cells were incubated at 37° C. for one week in vitro. At the end of the study, cells were fixed with 4% PFA and stained with MAP-2 and DAPI using immunocytochemistry methods previously described in section 2.4.2. To image, gels were placed face-down on a glass bottom dish and images were taken using the Nikon AIR confocal microscope. 150 µm thick Z-stack projections of each gel were collected by confocal microscopy. Depth analysis was performed on the confocal Z-stacks using the ImageJ software, and the MultiMeasure function within the ROI manager to measure the depth of pixels. The area under the curve (AUC) was calculated using Graphpad Prism version 6.0 data management software and the standard deviation was reported in A.U.

In order to analyze the fiber architecture of the superstructure, BDNF PA, $E_2$ PA and BDNF superstructure, a 405-labeled $E_2$ PA was incorporated at 1 mol %. Again, materials and gels were prepared as described in sections 2.1.1 and 2.1.2. To image the samples, a Nikon AIR confocal microscope with a 60× objective and a 2× Nyquist zoom was utilized for image capture. Each image was 15 µm in depth with a 0.25 µm step size. Images were then processed using Imaris shadow projection software. Using the statistics tab, the total volume of the field of view and the volume of the 405-labeled material within each z-stack projection was calculated.

2.4.7. Live Cell Dye Incorporation.

CellTrace™ CFSE or CellTrace™ Yellow dye were dissolved in DMSO at a concentration of 5 mM (ThermoFisher). After passaging, astrocytes were spun down and resuspended in PBS. The CellTrace dye was added at a working concentration of 5 µM and incubated at 1 million cells/mL 37 °C for 20 min. Concurrently, neurons were dissected following protocol described in section 2.3.1. and immediately resuspended in PBS at a concentration of 1 million cells/ml. Vybrant™ DiO (ThermoFisher) was used to label neurons and 5 µL of dye was added per mL of cell suspension. Cells were incubated for 20 min at 37° C. After incubation in their respective dyes, both types of cells were washed with PBS and media several times before resuspending them at the desired concentration within the superstructure PA and BDNF superstructure 3D printing inks.

2.4.8. 3D Printing.

The superstructure PA ink or BDNF superstructure ink was prepared by mixing the CD-$E_2$ PA and the Ada-$E_2$ PA solutions. Dyed cells were then mixed into the PA inks at the desired concentration and pipetted into the 3D printing syringes (Nordson EFD). 25 mm plastic coverslips (Thermanox) were placed inside 30 mm plastic petri dishes (Corning). Silicon isolators (Grace BIO-LABS) with a 20 mm diameter hole were used to hold the coverslip in place and guide the alignment of the 3D printer (BioX by CEL-LINK). A black dot was placed in the center of the silicon circle on the underside of the petri dish to help keep a consistent center point while printing. The main print design consisted of concentric circles filling the 20 mm well in the silicon isolator. The PA, or PA-Cell inks were extruded through a 0.41 mm inner diameter nozzle (Nordson EFD). The printer temperature was set to 37° C. A print speed of 3 mm/s and pressure of 10-20 kPa was used. Each ring consisted of 4 stacked layers of approximately 0.5 mm in height to create a total height of 2 mm. Gels containing cells were taken to a tissue culture hood and 4 mL of neuronal culture medium (previously described in section 2.3.4. was added to each dish. Gels were incubated for 7 DIV and then fixed with 4% PFA for 20 min at RT before being imaged on the Nikon Ti2 Widefield microscope or Nikon AIR confocal laser-scanning microscope.

2.4.9. Statistical Analysis.

Error bars shown indicate the standard error of the mean. Graphad Prism v.6 software was used to perform all statistical analysis. Analysis of variance (ANOVA) was used for all multiple group experiments with a Bonferroni post hoc test. P-values <0.05 were used to deem significance.

REFERENCES

1. Loebel, C.; Rodell, C. B.; Chen, M. H.; Burdick, J. A., Shear-thinning and self-healing hydrogels as injectable therapeutics and for 3D-printing. *Nat Protoc* 2017, 12 (8), 1521-1541.
2. Edelbrock, A. N.; Alvarez, Z.; Simkin, D.; Fyrner, T.; Chin, S. M.; Sato, K.; Kiskinis, E.; Stupp, S. I., Supramolecular Nanostructure Activates TrkB Receptor Signaling of Neuronal Cells by Mimicking Brain-Derived Neurotrophic *Factor. Nano Lett* 2018, 18 (10), 6237-6247.
3. Bolte, S.; Cordelieres, F. P., A guided tour into subcellular colocalization analysis in light microscopy. *J Microsc-Oxford* 2006, 224, 213-232.
4. Ortega, J. A.; Alcántara, S., BDNF/MAPK/ERK-induced BMP7 expression in the developing cerebral cortex induces premature radial glia differentiation and impairs neuronal migration. *Cereb Cortex* 2010, 20 (9), 2132-44.
5. Álvarez, Z.; Mateos-Timoneda, M. A.; Hyrošsová, P.; Castaño, O.; Planell, J. A.; Perales, J. C.; Engel, E.; Alcántara, S., The effect of the composition of PLA films and lactate release on glial and neuronal maturation and the maintenance of the neuronal progenitor niche. *Biomaterials* 2013, 34 (9), 2221-33.
6. Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; Tinevez, J. Y.; White, D. J.; Hartenstein, V.; Eliceiri, K.; Tomancak, P.; Cardona, A., Fiji: an open-source platform for biological-image analysis. *Nat Methods* 2012, 9 (7), 676-82.

What is claimed is:

1. A composition comprising:
  a. one or more host peptide amphiphiles comprising a hydrophobic segment comprising an 8-24 carbon alkyl chain ($C_{8-24}$), a structural peptide segment comprising $V_2A_2$, a charged peptide segment comprising $E_4$, and a host moiety comprising β-cyclodextrin; and
  b. one or more guest peptide amphiphiles comprising a hydrophobic segment comprising an 8-24 carbon alkyl chain ($C_{8-24}$), a structural peptide segment comprising $V_2A_2$, a charged peptide segment comprising $E_4$, and a guest moiety comprising adamantane; and
  c. one or more diluent peptide amphiphiles, wherein each of the one or more diluent peptide amphiphiles comprises a hydrophobic segment comprising an 8-24 carbon alkyl chain ($C_{8-24}$), a structural peptide segment, and a charged peptide segment, and does not comprise a host moiety or a guest moiety,
  wherein the host moiety and the guest moiety interact non-covalently to form a host-guest complex within the composition.

2. The composition of claim 1, wherein the β-cyclodextrin is conjugated to the charged peptide segment by a linker comprising 5-15 repeating polyethylene glycol (PEG) units and wherein the adamantane is conjugated to the charged peptide segment by a linker comprising 4-6 glycine residues.

3. The composition of claim 1, wherein the one or more host peptide amphiphiles comprise the sequence $C_{8-24}V_2A_2E_4PEG_{10}$-β-cyclodextrin, the one or more guest peptide amphiphiles comprise the sequence $C_{8-24}V_2A_2E_4G_6$-adamanatane, and/or the one or more diluent peptide amphiphiles comprise the sequence $C_{8-24}V_2A_2E_2$.

4. The composition of claim 1, further comprising one or more bioactive peptide amphiphiles comprising a hydrophobic segment, a structural peptide segment, a charged peptide segment, and a bioactive moiety.

5. The composition of claim 4, wherein the bioactive moiety is a BDNF mimetic peptide.

6. The composition of claim 5, wherein the bioactive peptide amphiphile comprises a $C_{8-24}$ $V_2A_2E_{2-4}$ backbone sequence linked to the BDNF mimetic peptide.

* * * * *